(12) United States Patent
Greiner et al.

(10) Patent No.: US 11,013,921 B2
(45) Date of Patent: *May 25, 2021

(54) METHODS AND SYSTEMS FOR TREATING CARDIOVASCULAR DISEASE USING AN IMPLANTABLE ELECTROACUPUNCTURE DEVICE

(71) Applicant: Valencia Technologies Corporation, Valencia, CA (US)

(72) Inventors: Jeffrey H. Greiner, Valencia, CA (US); David K. L. Peterson, Valencia, CA (US); Chuladatta Thenuwara, Castaic, CA (US)

(73) Assignee: Valencia Bioscience, Inc., Valencia, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 16/394,902

(22) Filed: Apr. 25, 2019

(65) Prior Publication Data

US 2019/0247274 A1 Aug. 15, 2019

Related U.S. Application Data

(60) Continuation of application No. 15/421,267, filed on Jan. 31, 2017, now Pat. No. 10,299,986, which is a
(Continued)

(51) Int. Cl.
*A61N 1/36* (2006.01)
*A61N 1/375* (2006.01)
(Continued)

(52) U.S. Cl.
CPC ......... *A61N 1/36114* (2013.01); *A61H 39/00* (2013.01); *A61H 39/002* (2013.01);
(Continued)

(58) Field of Classification Search
CPC ........................... A61H 139/002; A61H 39/00
(Continued)

(56) References Cited

U.S. PATENT DOCUMENTS 4,031,899 A 6/1977 Renirie
4,157,720 A 6/1979 Greatbatch et al.
(Continued)

FOREIGN PATENT DOCUMENTS

| EP | 1145736 | 10/2001 |
|---|---|---|
| WO | 01/41869 | 6/2001 |
| WO | 02/00294 | 1/2002 |

OTHER PUBLICATIONS

Acupuncture, http://en.wikipedia.org/wiki/Acupuncture.
(Continued)

*Primary Examiner* — Nadia A Mahmood
(74) *Attorney, Agent, or Firm* — ALG Intellectual Property, LLC

(57) ABSTRACT

A method of treating cardiovascular disease in a patient includes generating, by an implantable stimulator configured to be implanted beneath a skin surface of the patient, stimulation sessions at a duty cycle that is less than 0.05 and applying, by the implantable stimulator in accordance with the duty cycle, the stimulation sessions to a tissue location associated with the cardiovascular disease. The duty cycle is a ratio of T3 to T4. Each stimulation session included in the stimulation sessions has a duration of T3 minutes and occurs at a rate of once every T4 minutes. The implantable stimulator is powered by a primary battery located within the implantable stimulator and having an internal impedance greater than 5 ohms.

20 Claims, 31 Drawing Sheets

Related U.S. Application Data continuation of application No. 14/805,346, filed on Jul. 21, 2015, now Pat. No. 9,603,773, which is a continuation of application No. 14/669,155, filed on Mar. 26, 2015, now Pat. No. 9,433,788, which is a division of application No. 13/622,653, filed on Sep. 19, 2012, now Pat. No. 8,996,125.

(60) Provisional application No. 61/626,339, filed on Sep. 23, 2011, provisional application No. 61/606,995, filed on Mar. 6, 2012, provisional application No. 61/609,875, filed on Mar. 12, 2012, provisional application No. 61/672,257, filed on Jul. 16, 2012, provisional application No. 61/672,661, filed on Jul. 17, 2012, provisional application No. 61/673,254, filed on Jul. 19, 2012, provisional application No. 61/674,691, filed on Jul. 23, 2012, provisional application No. 61/676,275, filed on Jul. 26, 2012.

(51) Int. Cl.
*A61N 1/372* (2006.01)
*A61H 39/00* (2006.01)
*A61N 1/378* (2006.01)

(52) U.S. Cl.
CPC ...... *A61N 1/36117* (2013.01); *A61N 1/36125* (2013.01); *A61N 1/36175* (2013.01); *A61N 1/3756* (2013.01); *A61N 1/37205* (2013.01); *A61N 1/37223* (2013.01); *A61H 2201/01* (2013.01); *A61N 1/36153* (2013.01); *A61N 1/36157* (2013.01); *A61N 1/3782* (2013.01); *A61N 1/3787* (2013.01); *Y10T 29/49002* (2015.01)

(58) Field of Classification Search
USPC .......................................................... 607/46
See application file for complete search history.

(56) References Cited

U.S. PATENT DOCUMENTS

| | | | |
|---|---|---|---|
| 4,345,604 A | 8/1982 | Renirie | |
| 4,528,072 A | 7/1985 | Kurosawa et al. | |
| 4,535,784 A | 8/1985 | Rohlicek et al. | |
| 4,566,064 A | 1/1986 | Whitaker | |
| 5,195,517 A | 3/1993 | Chen | |
| 5,199,428 A | 4/1993 | Obel et al. | |
| 5,211,175 A | 5/1993 | Gleason et al. | |
| 5,250,068 A | 10/1993 | Ideguchi et al. | |
| 5,251,637 A | 10/1993 | Shalvi | |
| 5,372,605 A | 12/1994 | Adams et al. | |
| 5,544,656 A | 8/1996 | Pitsillides et al. | |
| 5,609,617 A | 3/1997 | Shealy et al. | |
| 5,707,400 A | 1/1998 | Terry, Jr. et al. | |
| 5,891,181 A | 4/1999 | Zhu | |
| 6,006,134 A | 12/1999 | Hill et al. | |
| 6,178,352 B1 | 1/2001 | Gruzdowich et al. | |
| 6,265,100 B1 | 7/2001 | Saaski et al. | |
| 6,393,324 B2 | 5/2002 | Gruzdowich et al. | |
| 6,522,926 B1 | 2/2003 | Kieval et al. | |
| 6,658,298 B2 | 12/2003 | Gruzdowich et al. | |
| 6,735,475 B1 | 5/2004 | Whitehurst et al. | |
| 6,839,596 B2 | 1/2005 | Nelson et al. | |
| 6,950,707 B2 | 9/2005 | Whitehurst | |
| 6,978,174 B2 | 12/2005 | Gelfand et al. | |
| 7,003,352 B1 | 2/2006 | Whitehurst | |
| 7,013,177 B1 | 3/2006 | Whitehurst et al. | |
| 7,046,499 B1 | 5/2006 | Imani et al. | |
| 7,136,701 B2 | 11/2006 | Greatbatch et al. | |
| 7,155,279 B2 | 12/2006 | Whitehurst et al. | |
| 7,162,303 B2 | 1/2007 | Levin et al. | |
| 7,171,266 B2 | 1/2007 | Gruzdowich et al. | |
| 7,203,548 B2 | 4/2007 | Whitehurst et al. | |
| 7,292,890 B2 | 11/2007 | Whitehurst et al. | |
| 7,321,792 B1 | 1/2008 | Min et al. | |
| 7,373,204 B2 | 5/2008 | Gelfand et al. | |
| 7,440,806 B1 | 10/2008 | Whitehurst et al. | |
| 7,444,180 B2 | 10/2008 | Kuzma et al. | |
| 7,496,408 B2 | 2/2009 | Ghanem et al. | |
| 7,610,100 B2 | 10/2009 | Jaax et al. | |
| 7,620,451 B2 | 11/2009 | Demarais et al. | |
| 7,657,316 B2 | 2/2010 | Jaax et al. | |
| 7,962,219 B2 | 6/2011 | Jaax et al. | |
| 2002/0016568 A1 | 2/2002 | Lebel et al. | |
| 2003/0078642 A1 | 4/2003 | Malaney et al. | |
| 2003/0158588 A1 | 8/2003 | Rizzo et al. | |
| 2003/0171790 A1 | 9/2003 | Nelson et al. | |
| 2003/0187485 A1 | 10/2003 | Sturman et al. | |
| 2003/0195583 A1 | 10/2003 | Gruzdowich et al. | |
| 2003/0195585 A1 | 10/2003 | Gruzdowich et al. | |
| 2003/0220668 A1 | 11/2003 | Shealy | |
| 2003/0236558 A1 | 12/2003 | Whitehurst et al. | |
| 2005/0107832 A1 | 5/2005 | Bernabei | |
| 2005/0228460 A1 | 10/2005 | Levin et al. | |
| 2005/0234533 A1 | 10/2005 | Schulman et al. | |
| 2006/0041283 A1 | 2/2006 | Gelfand et al. | |
| 2006/0184209 A1 | 8/2006 | John et al. | |
| 2007/0005119 A1 | 1/2007 | Crohn | |
| 2007/0219595 A1 | 9/2007 | He | |
| 2007/0255319 A1 | 11/2007 | Greenberg et al. | |
| 2007/0265680 A1 | 11/2007 | Liu | |
| 2007/0299482 A1 | 12/2007 | Littlewood et al. | |
| 2008/0015572 A1 | 1/2008 | Johnson et al. | |
| 2008/0091255 A1 | 4/2008 | Caparso et al. | |
| 2008/0097529 A1 | 4/2008 | Parramon et al. | |
| 2009/0192555 A1 | 7/2009 | Schleicher et al. | |
| 2009/0210026 A1 | 8/2009 | Solberg et al. | |
| 2009/0292341 A1 | 11/2009 | Parramon et al. | |
| 2010/0042137 A1 | 2/2010 | Oronsky et al. | |
| 2010/0069992 A1 | 3/2010 | Aghassian et al. | |
| 2010/0211132 A1 | 8/2010 | Nimmagadda et al. | |
| 2010/0324624 A1 | 12/2010 | Chang | |
| 2010/0327887 A1 | 12/2010 | Denison et al. | |
| 2011/0106219 A1 | 5/2011 | Cauller et al. | |
| 2011/0106220 A1 | 5/2011 | Degiorgio et al. | |
| 2011/0112603 A1 | 5/2011 | Degiorgio et al. | |
| 2011/0172739 A1 | 7/2011 | Mann et al. | |
| 2011/0218589 A1 | 9/2011 | Degiorgio et al. | |
| 2011/0218590 A1 | 9/2011 | Degiorgio et al. | |
| 2012/0022612 A1 | 1/2012 | Littlewood et al. | |
| 2012/0259390 A1 | 10/2012 | Canion | |
| 2013/0041396 A1 | 2/2013 | Ryotokuji | |

OTHER PUBLICATIONS

Acupuncture Today: Electroacupuncture, Feb. 1, 2004. Retrieved on-line Aug. 9, 2006 at http://www.acupuncturetoday.com/abc/electroacupuncture.php.
Electroacupuncture, http://en.wikipedia.org/wiki/Electroacupuncture.
Final Office Action received in U.S. Appl. No. 15/421,267 dated Oct. 30, 2018.
Non-Final Office Action received in U.S. Appl. No. 14/669,155 dated Mar. 2, 2016.
Non-Final Office Action received in U.S. Appl. No. 14/805,346 dated Jul. 7, 2016.
Non-Final Office Action received in U.S. Appl. No. 15/421,267 dated May 25, 2018.
Who Standard Acupuncture Point Locations in the Western Pacific Region, published by the World Health Organization (WHO), Western Pacific Region, 2008, ISBN 978 92 9061 248 7. The Table of Contents, Forward (p. v-vi), General Guidelines for Acupuncture Point Locations (pp. 1-21), as well as pp. 45, 64, 151, and 154.
Ballegaard, S. et al., Acupuncture in severe, stable angina pectoris: a randomized trial, Acta Med Scand 220: 307-13 (1986).
Cal, RL et al., Effects of electroacupuncture of "Shenmen" (HT 7) and "Zhizheng" (SI 7) on cardiac function and electrical activities of cardiac sympathetic nerve in acute myocardial ischemia rabbits, Zhen Ci Yan Jiu. 2007; 32(4): 243-6. Abstract (2007).

(56) References Cited

OTHER PUBLICATIONS

Cheung, et al., The Mechanism of Acupuncture Therapy and Clinical Case Studies, Taylor and Francis, published in London. 2001. ISBN 0-415-27254-8. The Forward, Chapters 1-3, and 5.

Chiu, YJ et al.,Cardiovascular and endocrine effects of acupuncture in hypotensive patients, Clin. Exp. Hyperten 19 (7), 1047-1063 (1997).

Gao, J. et al., Acupuncture pretreatment protects heart from injury in rats with myocardial ischemia and reperfusion via inhibition of the B1-adrenoceptor signaling pathway, Life Sciences 80 (2007) 1484-1489.

Han, Y. et al., Influence of needling with the combination of back-shu and front-mu points in the heart and pericardium meridian on the electrocardiography of patients with coronary heart disease, Chinese Acupuncture and Moxibustion Jun. 1994. Abstract. (1994).

Hongxing, Z et al., Control observation on acupuncture of Quchi (LI 11) and medication in transient action of decreasing blood pressure, Chinese Acupuncture and Moxibustion. 2001: 11. Abstract (2011).

Jacobsson, F. et al., The effect of transcutaneous electric nerve stimulation in patients with therapy resistant hypertension, J. Hum. Hypertens. 14(12), 795-798 (2000).

Kurono, Y. et al., The effect of acupuncture on the coronary arteries as evaluated by coronary angiography: a preliminary report, Am J Chin Med 30: 387-396 (2002).

Li, et al. Neural Mechanism of Electroacupuncture's Hypotensive Effects, Autonomic Neuroscience: Basic and Clinical 157 (2010) 24-30.

Li, P. et al., Reversal of Reflex-Induced Myocardial Ischemia by Median Nerve Stimulation: A Feline Model of Electroacupuncture, American Heart Association Circulation 1998, 97: 1186-1194.

Lin, D. et al., Effect of electroacupuncture on Neiguan and Shenmen Points on heart function after coronary artery bypass grafting in coronary heart disease, Modern Journal of Integrated Traditional Chinese and Western Medicine: 18:2241-41. Abstract. (2009).

Liu, XQ et al., Influence of acupuncture on epicardial monophasic action potential in vivo in dog with myocardial infarction, Tianjin Journal of Traditional Chinese Medicine 22: 480-481 (2005).

Longhurst, J.C. et al., Central & Peripheral Neural Mechanisms of Acupuncture in Myocardial Ischemia, International Congress Series 1238 (2002) 79-87.

Mannheimer, C. et al., The Problem of Chronic Refractory Angina, European Heart Journal (2002) 23, 355-370.

Middlekauff, HR et al., Acupuncture inhibits sympathetic activation during mental stress in advanced heart failure patients, J Cardiac Failure: 8:399-406 (2002).

Oka, T. et al., Treatment of angina pectoris with acupuncture —role of "Neiguan", Jpn J. Oriental Med. 38: 85-88.

Quirico, PE et al., Teaching Atlas of Acupuncture, vol. 1: Channels and Points. pp. 180-196.

Richter, A. et al., Effect of acupuncture in patients with angina pectoris, Eur Heart J: 12:175-8 (1991).

Sanderson, J. E. et al., Electrical neurostimulators for pain relief in angina, British Heart Journal (1990) 63:141-143.

Shi, X et al., Effect of acupuncture on heart rate variability in coronary heart disease patients, Zhongguo Zhong Xi Yi Jie He Za Zhi 15(9): 536-8. Abstract (1995).

Song, Kiseok et al., The Compact Electro-Acupuncture System for Multi-Modal Feedback Electro-Acupuncture Treatment, 34th Annual International Conference of the IEEE EMBS, San Diego, CA, USA, Aug. 28-Sep. 1, 2012.

Tjen-A-Looi, SC et al., Medullary substrate and differential cardiovascular responses during stimulation of specific acupoints, Am J Physiol Regullnteg Camp Physiol 2004, 287:R852-R862.

Wang, JD et al., An alternative method to enhance vagal activities and suppress sympathetic activities in humans, Autonomic Neuroscience: Basic and clinical100: 90-95. (2002).

Xiao-Min, T et al., Experimental study on electroacupuncture in "Neiguan" (PC6) on congestive heart failure rats model and its effect of Angll, ET, CGRP, Journal of Chengdu University of Traditional Chinese Medicine. Jan. 2007. Abstract. (2007).

Xie, L. et al., 124 cases of dyssomnia treated with acupuncture at sishencong points, J. Tradil. Chin. Med. 14, 171-173 (1994).

Xufh et al., Clinical observation on acupuncture combined with medication for intractable angina pectoris, Zhongguo Zhen Jiu. 25(2): 89-91, Abstract (2005).

Yang, et al., Cardioprotective effects of electroacupuncture pretreatment on patients undergoing heart valve replacement surgery: a randomized controlled trial, Ann Thorac Surg 89:781-6 (2010).

Yang, YF et al., Different effects of acupuncture at shenmen (HT7)-Tongli(HT5) and Shenmen-Neiguan (PC6) points on heart rate variability in healthy subjects, J Chin Med. 2009; 20 (3,4): 97-106 (2009).

Yuanhua, W et al., Effect of acupuncture at quchi and taichong on ET and ACE in the blood of patients with hypertension and exploration of its efficacy, Chinese Journal of Integrated Chinese and Western Medicine 24: 1080-83 (2004).

Zhou, W. et al., Afferent mechanisms underlying stimulation of modality-related modulation of acupuncture-related cardiovascular responses, J Appl Physiol 2005, 98:872-880.

Zhou, WY et al., Brain stem mechanisms underlying acupuncture modality-related modulation of cardiovascular responses rats, J Appl Physiol 2005, 99:851-860.

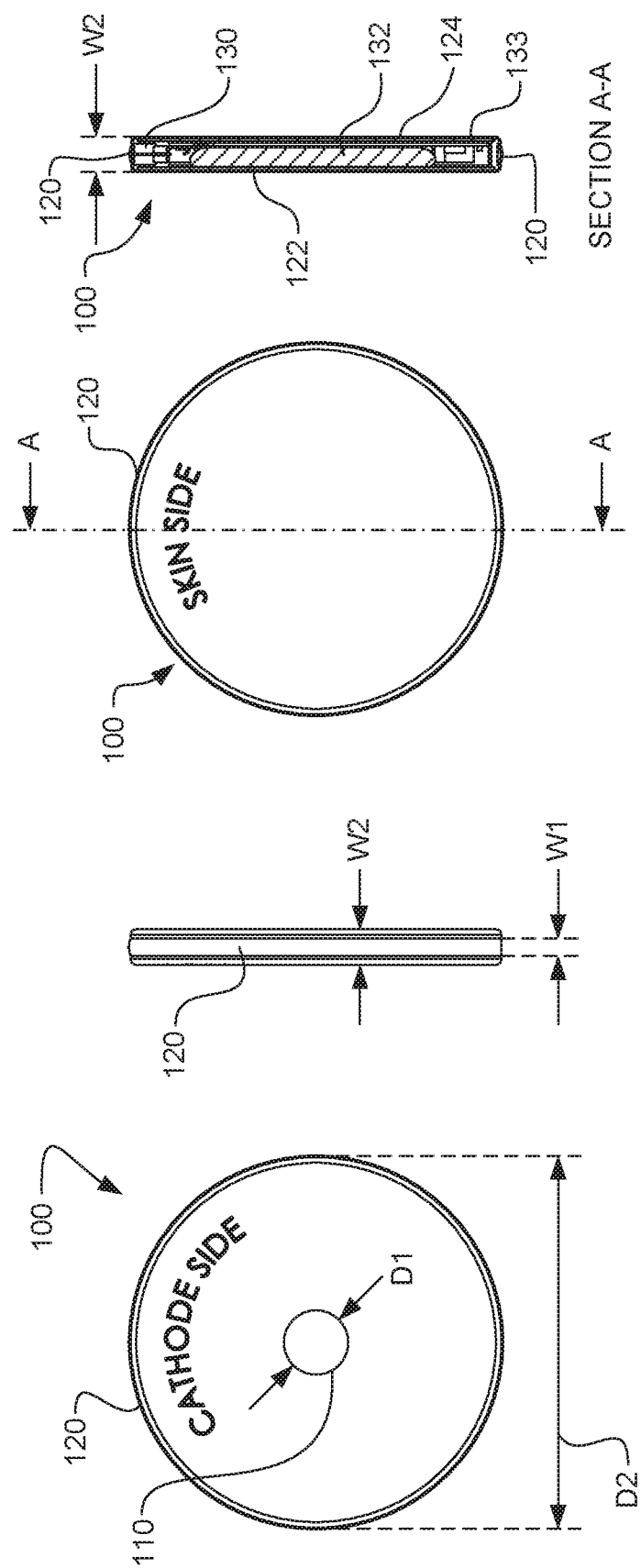

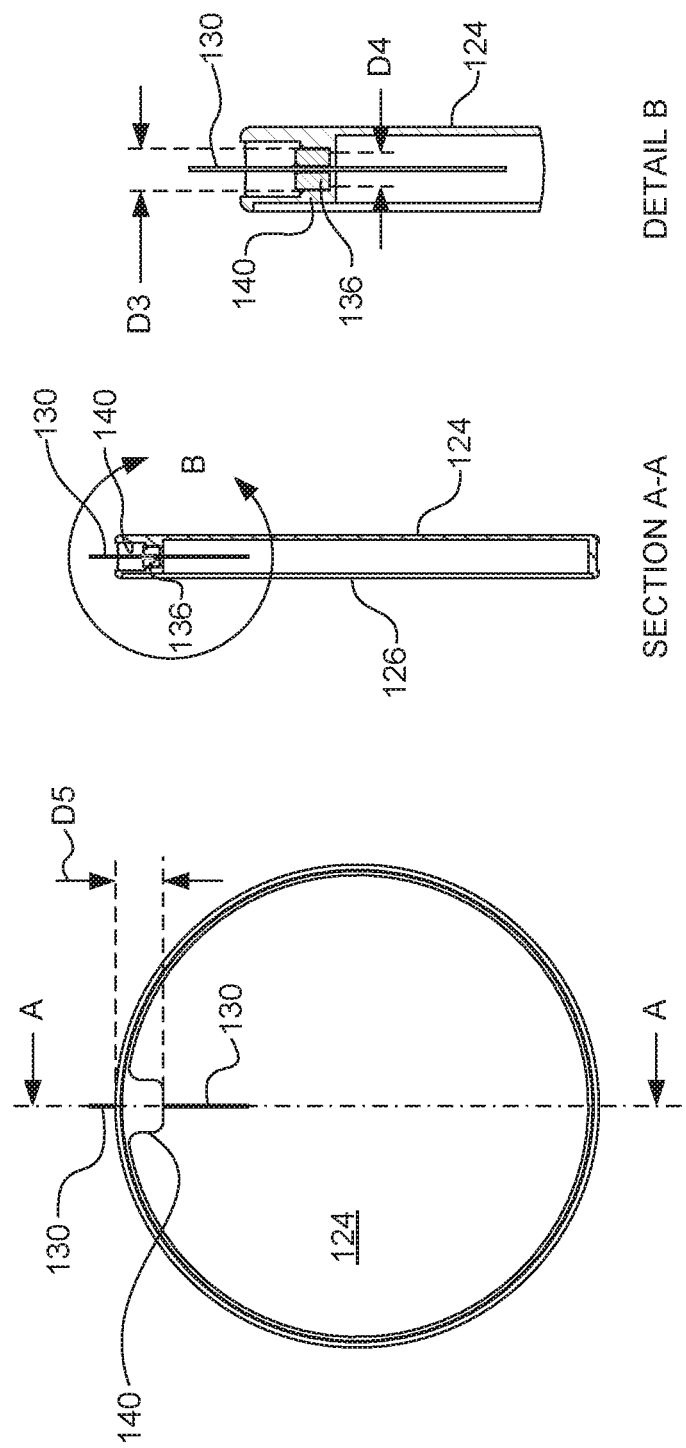

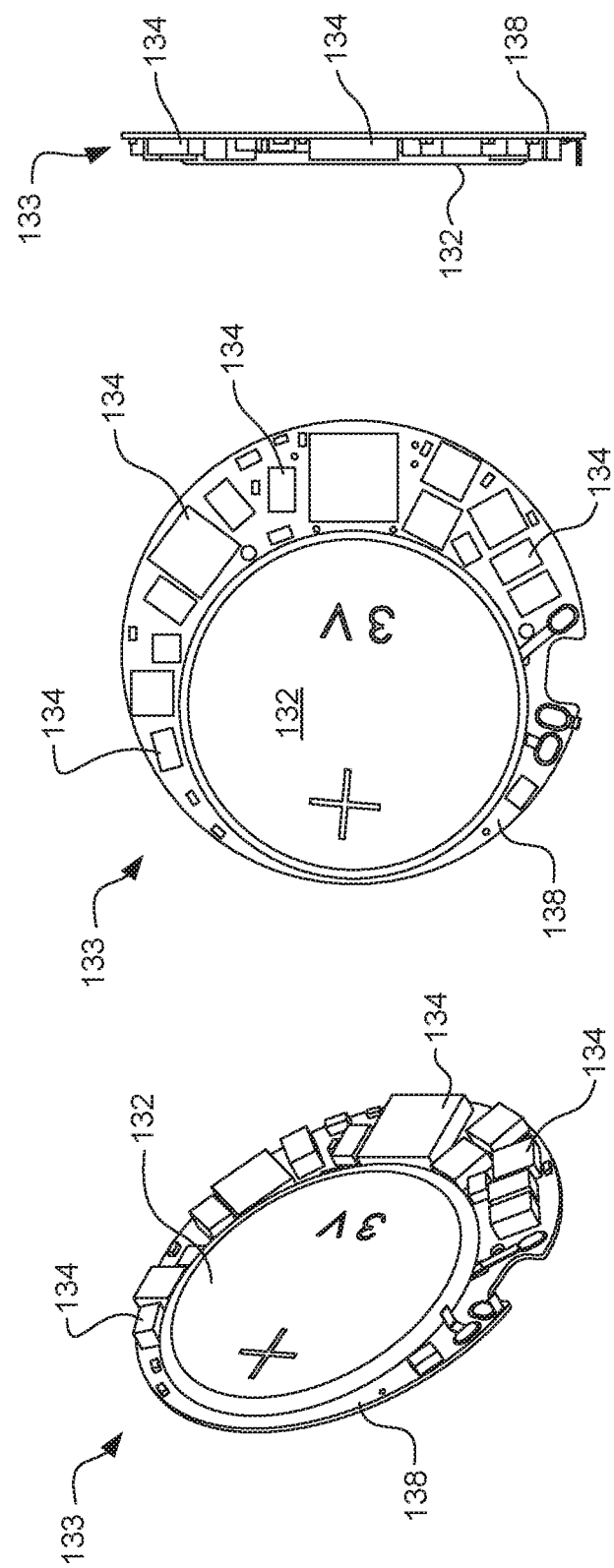

| Embodiment | Function of ECD | Function of IEAD |
|---|---|---|
| I | Program | Stimulate as Programmed |
| II | Program and Replenish; Interface with PC | Stimulate as Programmed |
| III | Program & Generate STIM Pulses; Interface with PC | Receives STIM Pulses and Directs Them to Electrodes |
| IV | ON/OFF – Simple Commands* (E.g., Magnet) | Stimulate per Pre-defined Stimulation Regimen |

*A few basic stimulation regimen parameters adjustable with simple encoding of externally-generated commands.

FIG. 18

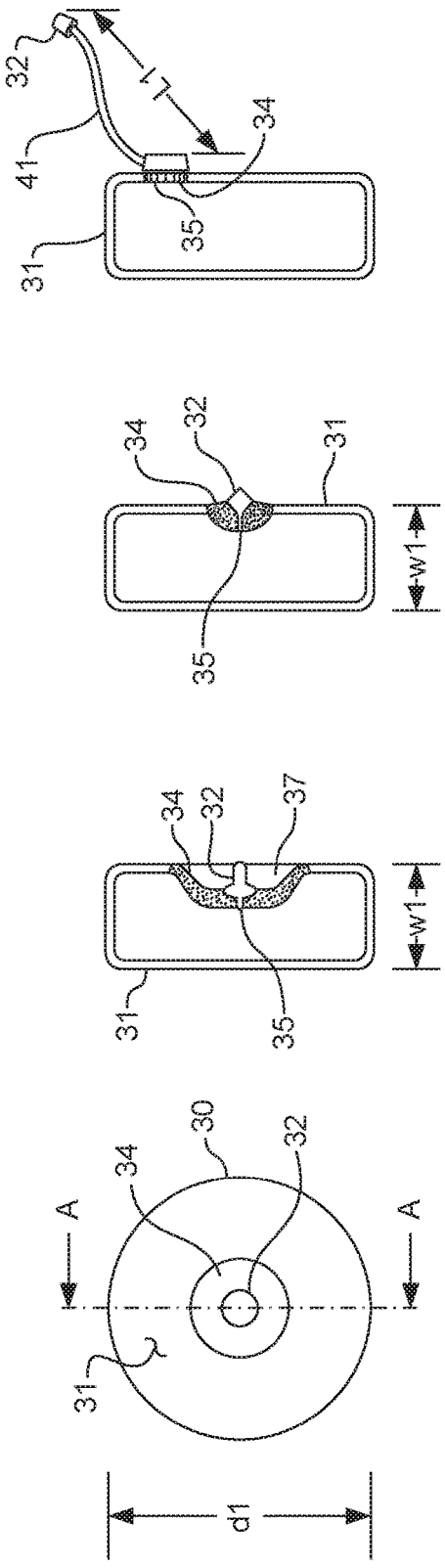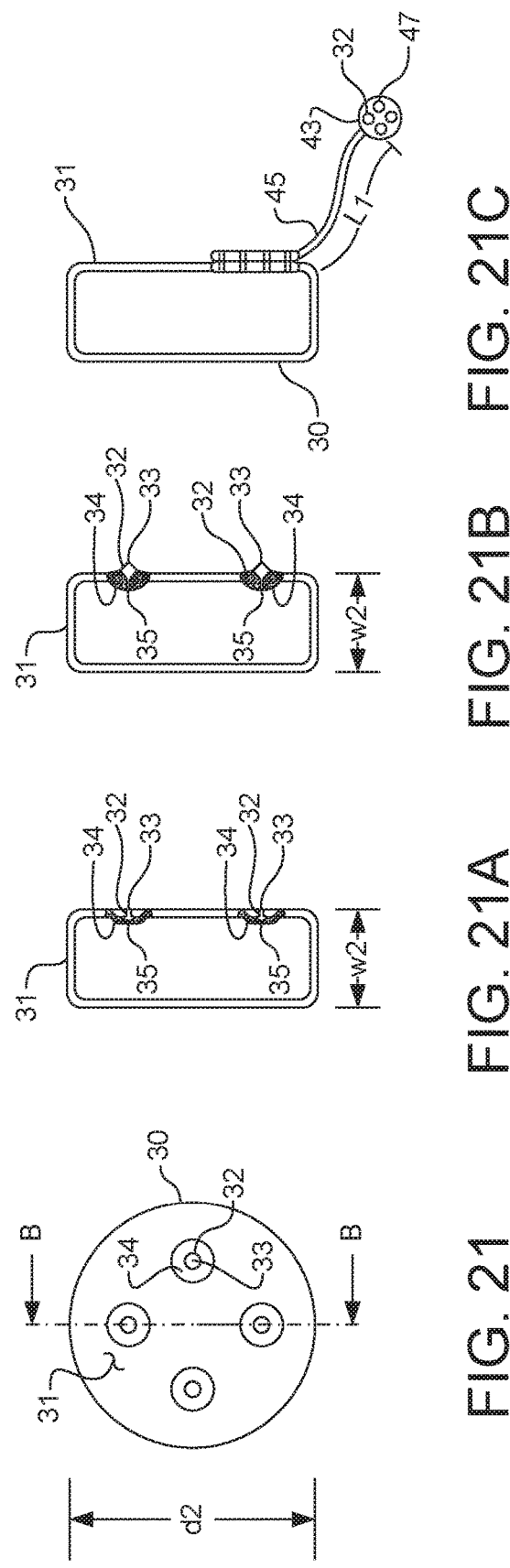

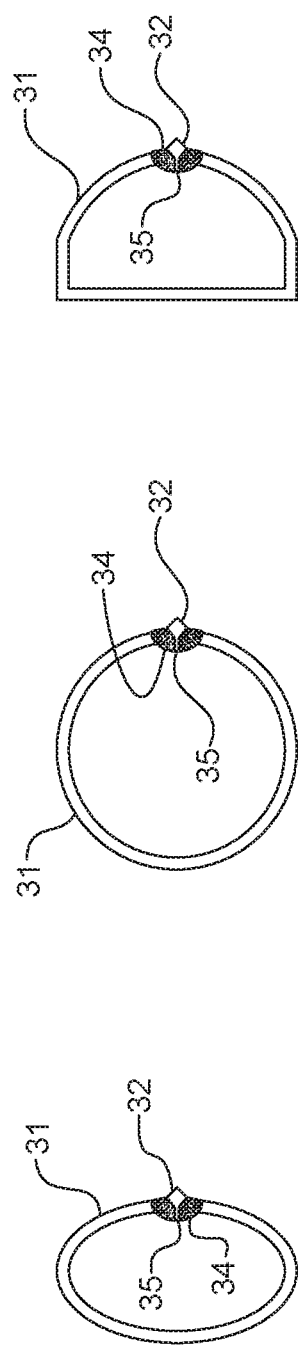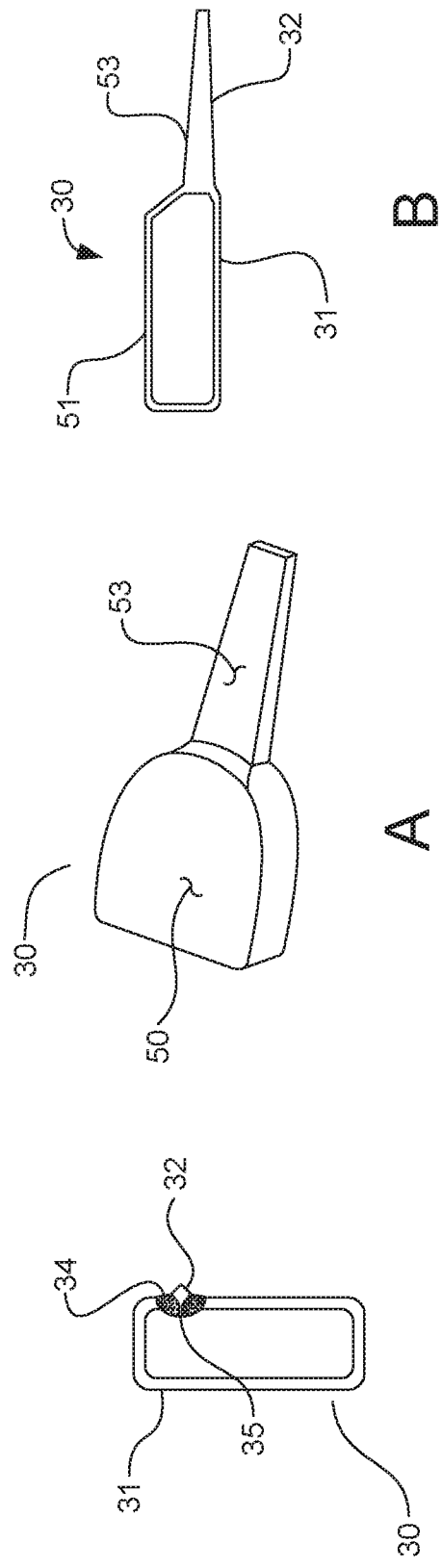
FIG. 22A  FIG. 22B  FIG. 22C  FIG. 22D  FIG. 22E

METHODS AND SYSTEMS FOR TREATING CARDIOVASCULAR DISEASE USING AN IMPLANTABLE ELECTROACUPUNCTURE DEVICE

RELATED APPLICATIONS

The present application is a continuation application of U.S. patent application Ser. No. 15/421,267, filed Jan. 31, 2017, which application is a continuation application of U.S. patent application Ser. No. 14/805,346, filed Jul. 21, 2015 and issued as U.S. Pat. No. 9,603,773, which application is a continuation application of U.S. patent application Ser. No. 14/669,155, filed Mar. 26, 2015 and issued as U.S. Pat. No. 9,433,788, which application is a divisional application of U.S. patent application Ser. No. 13/622,653, filed Sep. 19, 2012 and issued as U.S. Pat. No. 8,996,125. U.S. patent application Ser. No. 13/622,653 also claims priority under 35 U.S.C. § 119(e) to U.S. Provisional Patent Application No. 61/626,339, filed Sep. 23, 2011; U.S. Provisional Patent Application No. 61/606,995, filed Mar. 6, 2012; U.S. Provisional Patent Application No. 61/609,875, filed Mar. 12, 2012; U.S. Provisional Patent Application No. 61/672,257, filed Jul. 16, 2012; U.S. Provisional Patent Application No. 61/672,661, filed Jul. 17, 2012; U.S. Provisional Patent Application No. 61/673,254, filed Jul. 19, 2012; U.S. Provisional Patent Application No. 61/674,691, filed Jul. 23, 2012; and U.S. Provisional Patent Application No. 61/676,275, filed Jul. 26, 2012. All of these applications are incorporated herein by reference in their respective entireties.

BACKGROUND INFORMATION

Cardiovascular disease, also sometimes referred to as heart disease, cardiac disease or cardiopathy, is an umbrella term for a variety of diseases affecting the heart. Cardiovascular disease includes any of a number of specific diseases that affect the heart itself and/or the blood vessel system, especially the veins and arteries leading to and from the heart. Cardiovascular disease represents one of the more prevalent diseases affecting middle-aged and older-aged individuals in both Western and Eastern societies. As of 2007, cardiovascular disease was the leading cause of death in the United States, England, Canada and Wales, accounting for 25.4% of the total deaths in the United States.

In the United States, the most common type of cardiovascular disease is coronary artery disease (CAD). Coronary artery disease is a disease of the artery caused by the accumulation of atheromatous plaques within the walls of the arteries that supply the myocardium (the heart muscle). Angina pectoris (chest pain) and myocardial infarction (heart attack) are symptoms of and conditions caused by coronary artery disease.

Another type of cardiovascular disease is ischemic heart disease. Ischemia is defined as the inadequate flow of blood to a part of the body caused by constriction or blockage of the blood vessels supplying it. Ischemia of the heart muscle produces angina pectoris. Angina pectoris may be classified as either stable angina pectoris or unstable angina pectoris. Stable angina pectoris is angina pectoris induced by exercise and relieved by rest. Stable angina pectoris occurs when the demand for blood by the heart exceeds the supply of the blood provided by the coronary arteries.

Unstable angina pectoris, also known as "crescendo angina," is a form of acute coronary syndrome. It is defined as angina pectoris that changes or worsens. It occurs unpredictably at rest and may be a serious indicator of an impending heart attack. What differentiates stable angina from unstable angina (other than symptoms) is the pathophysiology of the atherosclerosis. The pathophysiology of unstable angina is the reduction of coronary flow due to transient platelet aggregation. In stable angina, the developing atheroma is protected with a fibrous cap. This cap (atherosclerotic plaque) may rupture in unstable angina, allowing blood clots to precipitate and further decrease the lumen of the coronary vessel. This explains why an unstable angina appears to be independent of activity.

There are currently a wide variety of methods that can be used to treat patients with cardiovascular diseases. These include risk factor reduction (e.g., diet, exercise, stress reduction), pharmacologic therapy (drugs), and invasive and interventional therapies as practiced by cardiologists and surgeons (e.g., bypass surgery).

Despite all the therapeutic measures available and practiced today, many patients remain severely incapacitated by their cardiovascular disease. Thus, in recent years there has been both a profound interest and acceptance of a number of alternative therapies. These therapies have emerged because none of the more usual therapies have been completely effective in eliminating either the symptoms or the adverse outcomes resulting from these diseases. Further, many mainstay therapies are associated with side effects that surprising numbers of patients find unacceptable. Therefore, there has been a surge of interest in alternative therapies. See, e.g., J. C. Longhurst "Central and Peripheral Neural Mechanisms of Acupuncture in Myocardial Ischemia", *International Congress Series* 1238 (2002) 79-87 (hereafter "Longhurst (2002)"); C. Mannheimer et al., "The Problem of Chronic Refractory Angina," *European Heart Journal* (2002) 23, 355-370 (hereafter "Mannheimer (2002)"); J. E. Sanderson, "Electrical Neurostimulators for Pain Relief in Angina," *British Heart Journal* (1990) 63:141-143 (hereafter "Sanderson (1990)").

The alternative approaches that have emerged in the medical management of cardiovascular disease include neuromodulation techniques; e.g., transcutaneous electric nerve stimulation (TENS) and spinal cord stimulation (SCS). Mannheimer (2002) at 360-362.

Neuromodulation techniques, including both TENS and SCS, appear to be safe and generally effective methods of treating angina pectoris. Transcutaneous electric nerve stimulation (TENS) is a neuromodulation technique that is comparable to needle acupuncture. However, instead of needles, standard electrodes are applied over the painful area of the chest wall. The device can usually be used by the patient at home after instruction. When an angina attack occurs or is anticipated, the patient applies stimulation for one to three minutes. It is essential to place the electrodes so that the stimulation paresthesia cover the area of angina pain, as this is the only way to ensure that the proper spinal segment is activated; i.e., the segment that supplies the heart with nerves. Id at 361.

Disadvantageously, skin irritation develops in a large number of patients, making it difficult to continue with this form of TENS therapy. Thus, if long term neuromodulation treatment is needed, as in angina, spinal cord stimulation (SCS) is typically used as a preferable treatment modality. Clinical observations also suggest that spinal cord stimulation may be more effective than TENS. Thus, TENS has recently been used more as a test method for planned implantation, to determine whether myocardial ischemia is really the cause of the patient's pain and to evaluate whether the patient shows good enough compliance to handle a spinal cord stimulator. Id.

Spinal cord stimulation requires implantation surgery. Implantation of the spinal cord system is performed under local anesthesia. The electrode is positioned epidurally so that paresthesia is produced in the region of angina pain radiation. The patient carries an implantable pulse generator in a subcutaneous pouch, typically below the left costal arch (rib cage). The electrode is then connected to the pulse generator by tunneling a subcutaneous lead from the epidural space (adjacent the spine on the back side of the patient) to the subcutaneous pouch below the patient's rib cage (on the front side of the patient). The system is similar to a pacemaker with the electrode placed in the epidural space instead of the heart. Id.

The TENS and SCS methods described above are potent and are capable of, at least temporarily (in the case of TENS), treating myocardial ischemia, such as angina pectoris. However, the use of TENS provides only temporary relief, and use of an SCS system is highly invasive and has potentially debilitating side effects. To use an SCS device to treat angina pectoris requires that a lead must be tunneled all the way from the back side of the patient to the front side of the patient. Such a method is as invasive as, and suffers from most of the same problems as, any major surgery. In addition, the complications associated with tunneling and removal of leads, which include infection, breakage, as well as the need to perform additional surgery, are not trivial.

Another alternative approach for treating cardiovascular disease, and a host of other physiological conditions, illnesses and deficiencies, is acupuncture, which includes traditional acupuncture, acupressure. Acupuncture has been practiced in Eastern civilizations (principally China, but also other Asian countries) for at least 2500 years. It is still practiced today throughout many parts of the world, including the United States and Europe. A good summary of the history of acupuncture, and its potential applications may be found in Cheung, et al., "*The Mechanism of Acupuncture Therapy and Clinical Case Studies*", (Taylor & Francis, publisher) (2001) ISBN 0-415-27254-8, hereafter referred to as "Cheung, *Mechanism of Acupuncture,* 2001." The Forward, as well as Chapters 1-3, 5, 7, 8, 12 and 13 of Cheung, *Mechanism of Acupuncture,* 2001, are incorporated herein by reference.

Despite the practice in Eastern countries for over 2500 years, it was not until President Richard Nixon visited China (in 1972) that acupuncture began to be accepted in Western countries, such as the United States and Europe. One of the reporters who accompanied Nixon during his visit to China, James Reston, from the *New York Times*, received acupuncture in China for post-operative pain after undergoing an emergency appendectomy under standard anesthesia. Reston experienced pain relief from the acupuncture and wrote about it in *The New York Times*. In 1973 the American Internal Revenue Service allowed acupuncture to be deducted as a medical expense. Following Nixon's visit to China, and as immigrants began flowing from China to Western countries, the demand for acupuncture increased steadily. Today, acupuncture therapy is viewed by many as a viable alternative form of medical treatment, alongside Western therapies. Moreover, acupuncture treatment is now covered, at least in part, by most insurance carriers. Further, payment for acupuncture services consumes a not insignificant portion of healthcare expenditures in the U.S. and Europe. See, generally, Cheung, *Mechanism of Acupuncture,* 2001, vii.

Acupuncture is an alternative medicine that treats patients by insertion and manipulation of needles in the body at selected points. Novak, Patricia D. et al (1995). Dorland's Pocket Medical Dictionary (25th ed.), Philadelphia: (W. B. Saunders Publisher), ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongi. The same acupoint may be identified by others by the name followed with a letter/number combination placed in parenthesis, e.g., Tongi (HT5). Alternatively, the acupoint may be identified by its letter/number combination followed by its name, e.g., HT5 (Tongi). The first letter typically refers to a body organ, or other tissue location associated with, or affected by, that acupoint. However, usually only the letter is used in referring to the acupoint, but not always. Thus, for example, the acupoint P-6 is the same as acupoint Pericardium 6 which is the same as PC-6 which is the same as Pe 6 which is the same as Neiguan. For purposes of this patent application, unless specifically stated otherwise, all references to acupoints that use the same name, or the same first letter and the same number, and regardless of slight differences in second letters and formatting, are intended to refer to the same acupoint. Thus, for example, the acupoint Neiguan is the same acupoint as Neiguan (P6), which is the same acupoint as Neiguan (PC6), which is the same acupoint as PC6 (Neiguan), which is the same acupoint as Neiguan (PC-6), which is the same acupoint as Neiguan (Pe-6), which is the same acupoint as P6, P 6, PC6 or PC-6 or Pe 6.

An excellent reference book that identifies all of the traditional acupoints within the human body is WHO STANDARD ACUPUNCTURE POINT LOCATIONS IN THE WESTERN PACIFIC REGION, published by the World Health Organization (WHO), Western Pacific Region, 2008 (updated and reprinted 2009), ISBN 978 92 9061 248 7 (hereafter "WHO Standard Acupuncture Point Locations 2008"). The Table of Contents, Forward (page v-vi) and General Guidelines for Acupuncture Point Locations (pages 1-21), as well as pages 151 and 154 (which pages illustrate with particularity the location of acupoint PC6) of the *WHO Standard Acupuncture Point Locations* 2008 are referred to herein as Appendix D.

While many in the scientific and medical community are highly critical of the historical roots upon which acupuncture has developed, (e.g., claiming that the existence of meridians, qi, yin and yang, and the like have no scientific basis), see, e.g., http://en.wikipedia.org/wiki/Acupuncture, few can refute the vast amount of successful clinical and other data, accumulated over centuries of acupuncture practice, that shows needle manipulation applied at certain acupoints is quite effective.

The World Health Organization and the United States' National Institutes of Health (NIH) have stated that acupuncture can be effective in the treatment of neurological conditions and pain. Reports from the USA's National Center for Complementary and Alternative Medicine (NCCAM), the American Medical Association (AMA) and various USA government reports have studied and commented on the efficacy of acupuncture. There is general agreement that acupuncture is safe when administered by well-trained practitioners using sterile needles, but not on its efficacy as a medical procedure.

An early critic of acupuncture, Felix Mann, who was the author of the first comprehensive English language acupuncture textbook *Acupuncture: The Ancient Chinese Art of Healing*, stated that "The traditional acupuncture points are no more real than the black spots a drunkard sees in front of his eyes." Mann compared the meridians to the meridians of longitude used in geography—an imaginary human construct. Mann, Felix (2000). *Reinventing acupuncture: a new concept of ancient medicine*. Oxford: Butterworth-Heinemann. pp. 14; 31. ISBN 0-7506-4857-0. Mann attempted to combine his medical knowledge with that of Chinese theory. In spite of his protestations about the theory, however, he apparently believed there must be something to it, because he was fascinated by it and trained many people in the West with the parts of it he borrowed. He also wrote many books on this subject. His legacy is that there is now a college in London and a system of needling that is known as "Medical Acupuncture". Today this college trains doctors and Western medical professionals only.

For purposes of this patent application, the arguments for and against acupuncture are interesting, but not that relevant. What is important is that a body of literature exists that identifies several acupoints within the human body that, rightly or wrongly, have been identified as having an influence on, or are otherwise somehow related to, the treatment of various physiological conditions, deficiencies or illnesses, including pain and other conditions associated with myocardial ischemia, such as angina pectoris. With respect to these acupoints, the facts speak for themselves. Either these points do or do not affect the conditions, deficiencies or illnesses with which they have been linked. The problem lies in trying to ascertain what is fact from what is fiction. This problem is made more difficult when conducting research on this topic because the insertion of needles, and the manipulation of the needles once inserted, is more of an art than a science, and results from such research become highly subjective. What is needed is a much more regimented approach for doing acupuncture research.

It should also be noted that other medical research, not associated with acupuncture research, has over the years identified nerves and other locations throughout a patient's body where the application of electrical stimulation produces a beneficial effect for the patient. Indeed, the entire field of neurostimulation deals with identifying locations in the body where electrical stimulation can be applied in order to provide a therapeutic effect for a patient. For purposes of this patent application, such known locations within the body are treated essentially the same as acupoints—they provide a "target" location where electrical stimulation may be applied to achieve a beneficial result, whether that beneficial result is to reduce pain, to treat myocardial ischemia, to treat hypertension, to mitigate some other form of cardiovascular disease or to address some other issue associated with a disease or condition of the patient.

Returning to the discussion regarding acupuncture, some have proposed applying moderate electrical stimulation at selected acupuncture points through needles that have been inserted at those points. Such electrical stimulation is known as electroacupuncture (EA). According to *Acupuncture Today*, a trade journal for acupuncturists: "Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004-02-01.

Recent research has reported the use of electroacupuncture (EA) for the treatment of myocardial ischemia and pain relief in angina. See, e.g., J. Gao, et al., "Acupuncture pretreatment protects heart from injury in rats with myocardial ischemia and reperfusion via inhibition of the $\square_1$-adrenoceptor signaling pathway," Life Sciences 80 (2007) 1484-1489 (hereafter "Gao (2007)"); Longhurst (2002); P. Li et al., "Reversal of Reflex-Induced Myocardial Ischemia by Median Nerve Stimulation: A Feline Model of Electroacupuncture," American Heart Association Circulation 1998, 97:1186-1194 (hereafter "Li (1998)"); Sanderson (1990).

The reason why acupuncture, including EA, can be used to treat angina is discussed at length in Cheung, *Mechanism of Acupuncture*, 2001, chapter 8, previously incorporated herein by reference.

Similar techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize either large implantable stimulators having long leads that must be tunneled through tissue to reach the desired stimulation site, or use external devices that must interface with implanted electrodes via percutaneous leads or wires passing through the skin. Such devices and methods are still far too invasive, or are ineffective, and thus are subject to the same limitations and concerns, as are the previously described electrical stimulation devices.

From the above, it is seen that there is a need in the art for a less invasive device and technique for electroacupuncture stimulation of acupoints that does not require the continual use of needles inserted through the skin, or long insulated wires implanted or inserted into blood vessels, for the purposes of treating cardiovascular diseases.

SUMMARY

One characterization of the invention described herein is an Implantable ElectroAcupuncture System (IEAS) that treats cardiovascular disease through application of electroacupuncture (EA) stimulation pulses applied at a specified tissue location(s) of a patient. A key component of such IEAS is an implantable electroacupuncture (EA) device. The EA device has a small, hermetically-sealed housing containing a primary power source, pulse generation circuitry powered by the primary power source, and a sensor that wirelessly senses operating commands generated external to the housing. The pulse generation circuitry generates stimulation pulses in accordance with a specified stimulation regimen as controlled, at least in part, by the operating commands sensed through the sensor. The EA device further includes a plurality of electrode arrays (where an electrode array comprises an array of n conductive contacts electrically joined together to function jointly as one electrode, where n is an integer less than 300) on the outside of the EA device housing that are electrically coupled to the pulse generation circuitry on the inside of the EA device housing. Such electrical coupling occurs through at least one feed-through terminal passing through a wall of the hermetically-sealed housing. Stimulation pulses generated by the pulse generation circuitry inside of the EA device housing are directed to the electrode arrays on the outside of the EA housing. The stimulation pulses are thus applied at the specified tissue location through the plurality of electrode arrays in accordance with the specified stimulation regimen. The specified stimulation regimen defines how often a stimulation session (a stimulation session comprises a stream of stimulation pulses) is applied to the patient, and the duration of each stimulation session. Moreover, the stimulation regimen requires that the stimulation session be applied at a very low duty cycle. More particularly, if the stimulation session has a duration of T3 minutes and occurs at a rate of once every T4 minutes, then the duty cycle, or the ratio of T3/T4, cannot be greater than 0.05.

Another characterization of the invention described herein is an Implantable ElectroAcupuncture System (IEAS) for treating heart failure, coronary artery disease, myocardial ischemia or angina of a patient. Such IEAS includes (a) an implantable electroacupuncture (EA) device housing having a maximum linear dimension of no more than 25 mm in a first plane, and a maximum height of no more 2.5 mm in a second plane orthogonal to the first plane; (b) a primary battery within the EA device housing having an internal impedance of no less than about 5 ohms; (c) pulse generation circuitry within the EA device housing and powered by the primary battery that generates stimulation pulses during a stimulation session; (d) control circuitry within the EA device housing and powered by the primary battery that controls the frequency of the stimulation sessions to occur no more than once every T4 minutes, and that further controls the duration of each stimulation session to last no longer than T3 minutes, where the ratio of T3/T4 is no greater than 0.05; (e) sensor circuitry within the EA device housing and coupled to the control circuitry that is responsive to the presence of a control command generated external to the EA device housing, which control command when received by the control circuitry sets the times T3 and T4 to appropriate values; and (f) a plurality of electrodes located outside of the EA device housing that are electrically coupled to the pulse generation circuitry within the EA device housing.

Use of the IEAS described herein advantageously allows stimulation pulses of the stimulation sessions to be applied to body tissue of the patient located in the vicinity of the plurality of electrodes. By strategically positioning the plurality of electrodes near at least one selected acupoint of the patient known to moderate or positively affect heart failure, coronary artery disease, myocardial ischemia or angina of the patient, such condition can be effectively treated over time.

A preferred acupoint to use with the IEAS for the purposes described herein is at least one of the following acupoints: PC6 in the right or left forearm; ST36 on the anterior aspect of the left or right leg, on the tibialis anterior muscle; BL14 (also referred to as UB14), in the upper back region; EX-HN1 (located approximately one centimeter from GV20, on the top of the head); HT7 on the anteromedial aspect of the right or left wrist, radial to the flexor carpi ulnaris tendon, on the palmar wrist crease; HT5 on the anteromedial aspect of the forearm, radial to the flexor carpi ulnaris tendon; LI11 on the lateral aspect of the elbow; LU2 on the anterior thoracic region, in the depression of the infraclavicular fossa; and LU7 on the radial aspect of the forearm, between the tendons of the abductor pollicis longus and the extensor pollicis brevis muscles.

Yet another characterization of the invention described herein is a method for treating cardiovascular disease in a patient. The method includes: (a) implanting an electroacupuncture (EA) device in the patient below the patient's skin at or near at least one specified acupoint; (b) enabling the EA device to generate stimulation sessions at a duty cycle that is less than 0.05, wherein each stimulation session comprises a series of stimulation pulses, and wherein the duty cycle is the ratio of T3/T4, where T3 is the duration of each stimulation session, and T4 is the time or duration between stimulation sessions; and (c) delivering the stimulation pulses of each stimulation session to the specified acupoint through a plurality of electrode arrays electrically connected to the EA device. Here, an electrode array comprises an array of n conductive contacts electrically joined together to function jointly as one electrode, where n is an integer from 1 to 30. The specified acupoint to use for this method is preferably one of the nine acupoints identified above in the previous paragraph.

A further characterization of the invention described herein is a method of treating heart failure, coronary artery disease, myocardial ischemia or angina in a patient using a small implantable electroacupuncture device (IEAD). Such IEAD is powered by a small disc primary battery having a specified nominal output voltage of about 3 volts and having an internal impedance of at least 5 ohms. The IEAD is configured, using electronic circuitry within the IEAD, to generate stimulation pulses in accordance with a specified stimulation regimen. These stimulation pulses are applied at a selected tissue location of the patient through at least two electrodes located outside of the housing of the IEAD. The method comprises: (a) implanting the IEAD below the skin surface of the patient at or near at least one acupoint selected from the group of acupoints that includes: PC6, ST36, BL14 (also referred to as UB14), EX-HN1 (located approximately one centimeter from GV20), HT7, HT5, LI11, LU2 and LU7; and (b) enabling the IEAD to provide stimulation pulses in accordance with a stimulation regimen that provides a stimulation session of duration T3 minutes at a rate of once every T4 minutes, where the ratio of T3/T4 is no greater than 0.05, and wherein T3 is at least 10 minutes and no greater than 60 minutes.

The invention described herein may additionally be characterized as a method of assembling an implantable electroacupuncture device (IEAS) in a small, thin, hermetically-sealed, housing having a maximum linear dimension in a first plane of no more than 25 mm and a maximum linear dimension in a second plane orthogonal to the first plane of no more than 2.5 mm. Such housing has at least one feed-through pin assembly radially passing through a wall of the thin housing that isolates the feed-through pin assembly from high temperatures and residual weld stresses that occur when the thin housing is welded shut to hermetically-seal its contents. The method comprises the steps of:

(a) forming a thin housing having a bottom case and a top cover plate, the top cover plate being adapted to fit over the bottom case, the bottom case having a maximum linear dimension of no more than 25 mm;
  (b) forming a recess in a wall of the housing;
  (c) placing a feed-through assembly within the recess so that a feed-through pin of the feed-through assembly electrically passes through a wall of the recess at a location that is separated from where the wall of the housing is designed to contact the top cover plate; and (d) welding the top cover plate to the bottom case around a perimeter of the bottom case, thereby hermetically sealing the bottom case and top case together.

Yet another characterization of the invention described herein is an Implantable ElectroAcupuncture System (IEAS) for treating heart failure, coronary artery disease, myocardial ischemia or angina. Such IEAS includes (a) at least one external component, and (b) a small, thin implantable component having a maximum linear dimension in a first plane of less than 25 mm, and a maximum linear dimension in a second plane orthogonal to the first plan of no more than 2.5 mm.

In one preferred embodiment, the external component comprises an electromagnetic field generator. As used herein, the term "electromagnetic field" encompasses radio frequency fields, magnetic fields, light emissions, or combinations thereof.

The implantable component includes a housing made of a bottom part and a top part that are welded together to create an hermetically-sealed, closed container. At least one feed-through terminal passes through a portion of a wall of the top part or bottom part. This terminal allows electrical connection to be made between the inside of the closed container and a location on the outside of the closed container. Electronic circuitry, including a power source, is included on the inside of the closed container that, when enabled, generates stimulation pulses during a stimulation session that has a duration of T3 minutes. The electronic circuitry also generates a new stimulation session at a rate of once every T4 minutes. The ratio of T3/T4, or the duty cycle of the stimulation sessions, is maintained at a very low value of no greater than 0.05. The stimulation pulses are coupled to the at least one feed-through terminal, where they are connected to a plurality of electrodes/arrays located on an outside surface of the closed housing. The stimulation pulses contained in the stimulation sessions are thus made available to stimulate body tissue in contact with or near the plurality of electrodes/arrays on the outside of the closed housing.

Further included on the inside of the closed container is a sensor adapted to sense the presence or absence of an electromagnetic field. Also included on the inside of the closed container is a power source that provides operating power for the electronic circuitry.

In operation, the external component modulates an electromagnetic field which, when sensed by the sensor inside of the closed container, conveys information to the electronic circuitry inside of the closed housing that controls when and how long the stimulation sessions are applied through the plurality of electrodes/arrays. Once this information is received by the electronic circuitry, the external component can be removed and the implantable component of the IEAS will carry out the stimulation regimen until the power source is depleted or new information is received by the electronic circuitry, whichever occurs first.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIGS. 1-16 relate to one preferred embodiment of the invention. FIGS. 17-31 relate to general principles and concepts associated with the invention.

FIG. 1 is a perspective view of an Implantable Electroacupuncture Device (IEAD) made in accordance with the teachings presented herein.

FIG. 2 shows a plan view of the bottom surface of the IEAD housing illustrated in FIG. 1.

FIG. 2A shows a side view of the IEAD housing illustrated in FIG. 1.

FIG. 3 shows a plan view of one side, indicated as the "skin" side, of the IEAD housing or case illustrated in FIG. 1.

FIG. 3A is a sectional view of the IEAD of FIG. 3 taken along the line A-A of FIG. 3.

FIG. 4 is a perspective view of the IEAD housing, including a feed-through pin, before the electronic components are placed therein, and before being sealed with a "skin side" cover plate.

FIG. 5 is a plan view of the empty IEAD housing shown in FIG. 4.

FIG. 5A depicts a sectional view of the IEAD housing of FIG. 5 taken along the section line A-A of FIG. 5.

FIG. 5B shows an enlarged view or detail of the portion of FIG. 5A that is encircled with the line B.

FIG. 6 is a perspective view of an electronic assembly, including a battery, that is adapted to fit inside of the empty housing of FIG. 4 and FIG. 5.

FIGS. 6A and 6B show a plan view and side view, respectively, of the electronic assembly shown in FIG. 6.

FIG. 7 is an exploded view of the IEAD assembly, illustrating its constituent parts.

FIG. 10 shows one preferred boost converter circuit and a functional pulse generation circuit configuration for use within the IEAD.

FIG. 11 shows an alternate boost converter circuit configuration and a functional pulse generation circuit for use within the IEAD.

FIG. 12 shows a refinement of the circuit configuration of FIG. 11.

FIG. 14 shows another preferred schematic configuration for an IEAD similar to that shown in FIG. 13A, but which uses an alternate output circuitry configuration for generating the stimulus pulses.

FIG. 16 shows a state diagram that shows the various states in which the IEAD may be placed through the use of an external magnet.

FIG. 17 is a block diagram that illustrates the two main components of an Electroacupuncture (EA) Stimulation System made as taught herein. Such EA Stimulation System (also referred to herein as an "EA System") includes: (1) an External Control Device (ECD); and (2) an Implantable Stimulator (also referred to herein as an "Implantable Electroacupuncture Device" or IEAD). Two variations of the IEAD are depicted, either one of which could be used as part of the EA System, one having electrodes formed as an integral part of the IEAD housing, and another having the electrodes at or near the distal end of a very short lead that is attached to the IEAD.

FIG. 18 is a Table that summarizes the functions performed by the two main components of the EA System of FIG. 1A in accordance with various configurations of the invention.

FIG. 19 is an illustration of the human body, and shows the location of some effective and ineffective acupoints used in electroacupuncture for the treatment of cardiovascular disease, hypertension and other maladies. This figure is taken from Li et al., "Neural Mechanism of Electroacupuncture's Hypotensive Effects", *Autonomic Neuroscience: Basic and Clinical* 157 (2010) 24-30. A much more detailed representation of these and other acupoints may be found in *WHO Standard Acupuncture Point Locations* 2008, selected portions of which may be found in Appendix D.

FIG. 20 shows the use of one type of electrode integrated within the underneath side (the side farthest away from the skin) of a housing structure of an implantable electroacupuncture device, or IEAD. This electrode is insulated from the other portions of the IEAD housing, which other portions of the housing structure may function as a return electrode for electroacupuncture stimulation.

FIG. 20A is a sectional view, taken along the line A-A of FIG. 20, that shows one embodiment or variation of the IEAD housing wherein the electrode of FIG. 20 resides in a cavity formed within the underneath side of the IEAD.

FIG. 20B is a sectional view, taken along the line A-A of FIG. 20, and shows an alternative embodiment or variation of the underneath side of the IEAD housing wherein the electrode comprises a smooth bump that protrudes out from the underneath surface of the IEAD a short distance.

FIG. 20C is a sectional view, taken along the line A-A of FIG. 20, and shows yet an additional alternative embodiment or variation of the underneath side of the IEAD housing wherein the electrode is at or near the distal end of a short lead that extends out a short distance from the underneath side of, or an edge of, the IEAD housing.

FIG. 21 is similar to FIG. 20, but shows the use of an electrode array having four individual electrodes integrated within the housing structure of an IEAD.

FIG. 21A is a sectional view, taken along the line B-B of FIG. 21, that shows an embodiment where the electrodes comprise rounded bumps that protrude out from the underneath surface of the IEAD a very short distance.

FIG. 21B is likewise a sectional view, taken along the line B-B of FIG. 21, that shows an alternative embodiment or variation where the electrodes comprise tapering cones or inverted-pyramid shaped electrodes that protrude out from the underneath surface of the IEAD a short distance and end in a sharp tip, much like a needle.

FIG. 21C is a also a sectional view, taken along the line B-B of FIG. 21, that shows yet another embodiment or variation of the underneath surface of the IEAD housing where the electrodes comprise small conductive pads formed at or near the distal end of a flex circuit cable (shown twisted 90 degrees in FIG. 21C) that extends out from the underneath surface of the IEAD housing a short distance.

FIGS. 22A through 22E show various alternate shapes of the housing of the IEAD that may be used with an EA System. Each respective figure, FIG. 22A, FIG. 22B, FIG. 22C, and FIG. 22D show side sectional views of the housing shape, and FIG. 22E shows both a perspective view (labeled as "A") and a side view (labeled as "B") of the housing shape.

FIG. 23 is an electrical functional block diagram of the circuitry and electrical components housed within an EA System which includes an IEAD and External Controller in accordance with the various embodiments of the invention. The functional circuitry shown to the right of FIG. 23 is what is typically housed within the IEAD. The functional circuitry shown to the left of FIG. 23 is what is typically housed within the External Controller. How much circuitry is housed within the IEAD and how much is housed within the External Controller is a function of which embodiment of the EA System is being used.

FIG. 24 is an electrical functional block diagram of a passive IEAD (where "passive", as used herein, means a circuit that generally employs only wires or conductors, capacitors, or resistors, and requires no internal power source). This passive IEAD is intended for use with Embodiment III (FIG. 18).

FIG. 26 illustrates one embodiment of a power source that may be used within the IEAD which utilizes both a super-capacitor and a rechargeable battery.

FIG. 27 is a timing diagram that illustrates a typical stimulation pattern of biphasic stimulation pulses used by the EA System, and defines some of the operating parameters that may be programmed as part of the programmed stimulation regime.

FIG. 28 is likewise a timing diagram that illustrates, on a larger time scale than FIG. 27, various stimulation patterns and operating parameters that may be programmed for use by the EA System.

FIG. 29 is a flowchart that illustrates a typical EA stimulation process or method for use with the EA stimulation system described herein.

FIG. 30 is a flowchart that illustrates a manually triggered EA stimulation process or method for use with the EA stimulation system described herein.

FIG. 31 is an alternate flowchart that illustrates another representative EA stimulation process or method that may be used with some embodiments of the IEAD described herein.

Figure 1:
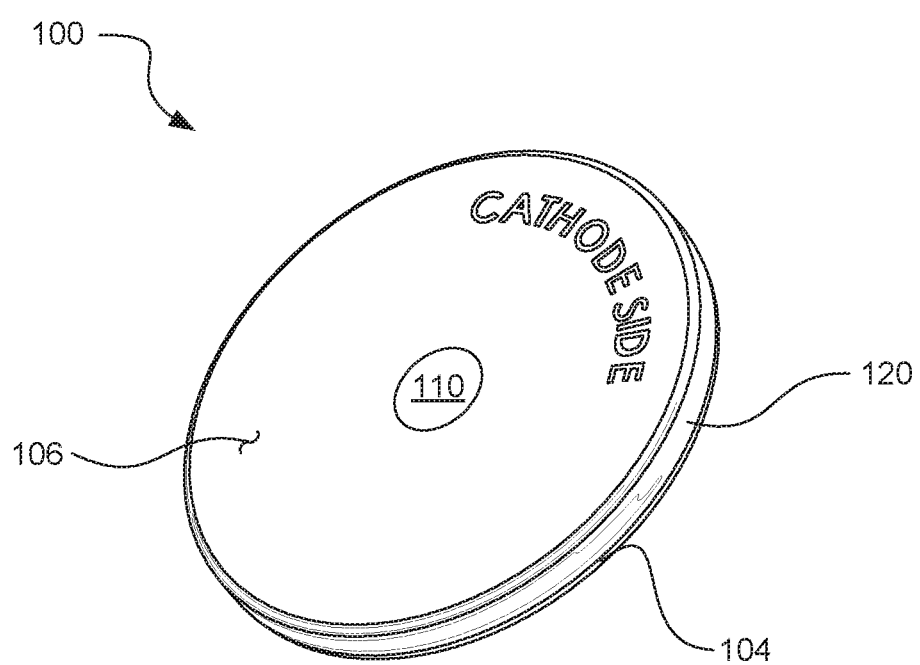

Appendix A illustrates some examples of alternate symmetrical electrode configurations that may be used with an IEAD of the type described herein.

Appendix B illustrates a few examples of non-symmetrical electrode configurations that may be used with an IEAD made in accordance with the teachings herein.

Appendix C shows an example of the code used in the micro-controller IC (e.g., U2 in FIG. 14) to control the basic operation and programming of the IEAD, e.g., to Turn the IEAD ON/OFF, adjust the amplitude of the stimulus pulse, and the like, using only an external magnet as an external communication element.

Appendix D contains selected pages from the WHO Standard Acupuncture Point Locations 2008 reference book, referred to previously, as well as selected pages from other references.

Appendix E shows alternate case shapes and electrode placements for an implantable EA device of the type disclosed herein.

Appendix F illustrates alternate approaches for use with a short pigtail lead attached to the housing of the EA stimulation device.

Appendices A, B, C, D, E and F were submitted one or more of Applicant's parent applications and are incorporated by reference herein.

Throughout the drawings and appendices, identical reference numbers designate similar, but not necessarily identical, elements.

DETAILED DESCRIPTION

Overview

Disclosed and claimed herein is a small electroacupuncture (EA) device, having one or more electrodes formed within and as an integral part of, or anchored to, its housing. The EA device is adapted to be implanted through a very small incision, e.g., less than 2-3 cm in length, directly adjacent to a selected acupuncture site known to moderate or affect a patient's physiological or health condition that needs treatment. In accordance with the teachings herein, the small EA device is implanted so that its electrodes are located and anchored precisely at a target acupuncture site. (An acupuncture site may also be referred to herein as an "acupoint.") When a precise physical location of the electrode(s) is not achieved through implantation, electrical fields emanating from two or more electrodes of the EA device may be combined or superimposed so as to create a virtual electrode whose virtual position may be finely adjusted to be precisely at the desired acupoint.

Once the electrode(s) are anchored at the selected acupuncture site, electrical stimulation is applied using a low intensity, low frequency and low duty cycle stimulation regime that is designed to achieve the same or similar beneficial therapeutic effects as have previously been obtained through conventional acupuncture treatments or nerve stimulations. One of the primary advantages and benefits provided by the EA device disclosed herein (used to electrically stimulate acupoints) is that an entire body of medicine (acupuncture, as developed and matured over thousands of years) may be brought to the general populace with a much more uniform approach than has heretofore been achievable.

As used herein, note that "EA device" may refer to either a small Implantable NeuroStimulator (INS) designed for stimulating nerves and/or other body tissue at a precisely-defined location; or a small implantable electroacupuncture (EA) device, or "IEAD", designed to stimulate an acupuncture site, or acupoint, where an "acupoint" is inherently defined as a precise tissue location. Thus, as used herein, IEAD=EA device=implanted neurostimulator=INS. And, as used herein, acupoint=an acupuncture stimulation point=a target tissue/nerve stimulation location where electrical pulses generated by a neurostimulator device, i.e., an EA device, are applied.

Also, as used herein, "electrode" and 'electrode contact" or "electrodes" and "electrode contacts" or electrode array, are often used interchangeably to refer to that part of the EA device housing, or that part of a lead connected to an EA or INS device, from which electrical stimulation pulses, currents and/or voltages are applied to body tissue.

Applying the EA stimulation according to a prescribed stimulation regime is an important key of the invention because it allows a more uniform health care approach to be followed for treatment of a particular disorder or illness. Conventional acupuncture treatment, on the other hand, relies heavily on the skill and experience of the acupuncturist, which may vary a great deal from acupuncturist to acupuncturist. In contrast, electroacupuncture treatment as taught herein may be uniformly applied for a specific disorder or illness once the electrodes are positioned at or near the correct acupoint, or other tissue location known to affect a condition being treated, and once the prescribed stimulation regime is shown to be effective.

Applying the EA stimulation at low intensities, low frequencies and low duty cycles is also a key feature of the invention because it allows the power source of the EA device to be small, yet still with sufficient capacity to uniformly carry out the stimulation procedure (or stimulation regime) for several years, thereby reducing the amount of time a patient has to spend at the office of medical personnel who are monitoring or otherwise overseeing the patient's treatment.

Further, having the EA device be small, with the electrodes an integral part of the housing of the device, or in very close proximity of the device at the distal end of a very short lead, overcomes the limitations of having to use a large pulse generator implanted in the trunk of the patient's body and thereafter having an insulated lead wire tunneled through the limbs to an acupuncture point. (It is noted that the use of a large pulse generator in the body's trunk, with long leads tunneled through tissue or blood vessels to the needed acupoint is the current state of the art in implanted electroacupuncture art, as evidenced, e.g., in U.S. Pat. No. 7,373, 204).

A preferred EA device made in accordance with the teachings of the invention is thus small, and has a mechanical shape or envelope that makes it easy to implant through a small incision made near or at the acupuncture site. The EA device may be configured in various shapes. One shape that may be used is configured in disk form, with a diameter of 2 to 3 cm, and a thickness of 2-4 mm. Other shapes that could be used include egg-shaped, spherical or semi-spherical, rectangular with rounded corners, key-shaped, and the like. Whatever the shape, once the EA device is implanted, the housing of the EA device, with its particular shape, helps anchor the device, and more importantly helps anchor its electrodes, in their desired position at or near the target acupoint that is to be stimulated.

A preferred application for an EA device made in accordance with the teachings presented herein is to treat cardiovascular disease, and more particularly heart failure, coronary artery disease (CAD), myocardial ischemia, and angina. Thus, the description that follows describes in much more detail an EA device that is especially suited to be used to treat cardiovascular disease. However, it is to be understood that the invention is not limited to treating cardiovascular disease. As explained in more detail below, the essence of the invention recognizes that an electroacupuncture modulation scheme need not be continuous, thereby allowing the implanted EA device to use a small, high density, power source to provide such non-continuous EA modulation. (Here, it should be noted that "EA modulation," as that phrase is used herein, is the application of electrical stimulation pulses, at low intensities, low frequencies and low duty cycles, to at least one of the acupuncture sites that has been identified as affecting a particular illness, deficiency or condition.) As a result, the EA device can be very small. And, because the electrodes form an integral part of the housing of the EA device, or are connected thereto through a very short lead, the EA device may thus be implanted directly at (or very near to) the desired acupoint. Hence, any condition of a patient that has heretofore been successfully treated through conventional acupuncture treatments is a potential candidate for treatment with the EA device described herein.

Modulation (i.e., EA stimulation) regimes, of course, may need to be tailored to the specific illness, condition or deficiency being treated, but the same basic approach may be followed as is taught herein for whatever acupoint is to be modulated. In summary, and as explained more fully below in conjunction with the description of the treating heart failure, CAD, myocardial ischemia, and/or angina, the basic approach of EA stimulation includes: (1) identify an acupoint(s) that may be used to treat or mediate the particular illness, condition or deficiency that has manifest itself in the patient; (2) implant an EA device, made as described herein, so that its electrodes are firmly anchored and located so as to be near or on the identified acupoint(s); (3) apply EA modulation, having a low intensity, low frequency, and low duty cycle through the electrode(s) of the EA device so that electrical stimulation pulses flow through the tissue at the acupoint(s) following a prescribed stimulation regimen over several weeks or months or years. At any time during this EA stimulation regimen, the patient's illness, condition or deficiency may be evaluated and, as necessary, the parameters of the EA modulation applied during the EA stimulation regimen may be adjusted or tweaked in order to improve the results obtained from the EA modulation.

Conditions Treated

As indicated previously, cardiovascular disease is an umbrella term for a variety of diseases affecting the heart. Cardiovascular disease includes any of a number of specific diseases that affect the heart itself and/or the blood vessel system, especially the veins and arteries leading to and from the heart. For purposes of this patent application, the cardiovascular diseases best treated by the EA device described herein, and the methods of using such EA device, are focused on the following conditions:

(1) heart failure;
(2) coronary artery disease (also sometimes referred to as coronary heart disease, and abbreviated as "CAD" or "CHD");
(3) myocardial ischemia; and
(4) angina.

Each of these four conditions is described in more detail in the paragraphs that follow.

The first of the cardiovascular conditions treated by the device and methods described herein is heart failure. Heart failure develops in response to an insult resulting in a decline in the pumping capacity of the heart. (Note, an "insult" in medical terms is a bodily injury, irritation, or other trauma.) In response to the decline in pumping capacity, compensatory neurohumoral mechanisms are activated. Among others, the Sympathetic Nervous System (SNS), the Renin Angiotensin Aldosterone System (RAAS), and the Cytokine System, are activated. Sympathetic nervous system activation has been associated with progression of heart failure, increased sudden death risk, and increased mortality. Initially, these neurohumoral mechanisms are able to compensate for the depressed heart function and maintain hemodynamic stability. However, long-term activation of these neurohumoral mechanisms has deleterious effects on cardiac structure and performance, leading to cardiac decompensation and heart failure progression. Heart failure patients with the greatest sympathetic activation have the worst prognosis. Pharmacologic treatment of heart failure is focused on interruption of this sympathetic activation with stability or improvement in cardiac function and decreased mortality.

The role of increased sympathetic activity in the progression of heart failure is well understood. The most heightened sympathetic activity is positively associated with the worst prognosis in heart failure. Thus, the normalization of sympathetic activity is a target in the treatment of heart failure. International guidelines for the treatment of heart failure and myocardial infarction focus on reducing the severity of the neurohumoral activation. The benefits of beta-blocker therapy, for example, as a pharmaceutical targeting inhibition of the SNS, is considered a worthwhile treatment to attenuate the progression of heart failure.

Heart failure means that the heart is unable to pump enough blood to meet the needs of the body. In addition to hypertension, coronary artery disease (CAD)—the narrowing of the arteries in the heart—may lead to heart failure. The narrowed arteries may limit the heart's supply of oxygen rich blood resulting in weakened heart muscles. Most commonly the narrowing is caused by plaque buildup on (or, atherosclerosis of) the coronary arteries. As a result of the narrowing and limited blood supply to the heart (characterized as myocardial ischemia), chest pain called angina often results. A complete blockage can cause a myocardial infarction (a heart attack).

In a small study of 20 patients with advanced heart failure who underwent acute mental stress testing to examine changes in sympathetic activity associated with that stress, those patients who underwent active acupuncture treatment did not have increased sympathetic activity after acupuncture and mental stress testing, unlike the control group who experienced a 25% increase. Middlekauff H R, Yu J L, Hui K, et al.: "Acupuncture inhibits sympathetic activation during mental stress in advanced heart failure patients," *J Cardiac Failure:* 8:399-406 (2002).

Additionally, acupuncture in hypertensive patients and its effect on sympathetic activity is also suggestive of utility in heart failure. See, e.g., Longhurst J C: "Acupuncture's beneficial effects on the cardiovascular system," *Prev Cardiol:* 1:21-33 (1998).

The second of the cardiovascular conditions treated by the device and methods described herein is coronary artery disease (also sometimes referred to as coronary heart disease, and abbreviated as "CAD" or "CHD", respectively). The current science in acupuncture suggests that the mechanism of acupuncture therapy for CAD involves improvement in the neurohumoral regulation, the increase of coronary blood flow and myocardial oxygen supply, and the reduction of myocardial oxygen consumption, thereby improving myocardial ischemia.

In a Japanese study, three patients with coronary artery disease who were treated by acupuncture at PC6 had a decrease in angina episodes during workload and an improvement in clinical symptoms. Oka, T., Y. Tsuda, S. Suzuki, R. Aji, S. Kaneya and T. Fujino: "Treatment of angina pectoris with acupuncture—role of 'Neiguan,'" *Jpn. J. Oriental Med.* 38: 85-88 (1987, in Japanese).

In another Japanese study, the measured effect of acupuncture on coronary artery dilatation during coronary angiography was 68% of that produced by isosorbide dinitrate. Kurono Y, Egawa M, Yano T, Shimoo K: "The effect of acupuncture on the coronary arteries as evaluated by coronary angiography: a preliminary report," *Am J Chin Med* 30: 387-396 (2002).

In patients who underwent coronary artery bypass grafting in coronary artery disease, acupuncture applied at HT7 and PC6 increased cardiac output and improved heart function better than in the control group, which used drugs only. Lin D, Lin Y, Hu J, Ruan X: "Effect of Electroacupuncture on Neiguan and Shenmen Points on heart function after coronary artery bypass grafting in coronary heart disease." *Modern Journal of Integrated Traditional Chinese and Western Medicine:* 18:2241-41. Abstract. (2009).

The third of the cardiovascular conditions treated by the device and methods described herein is myocardial ischemia. In animals, acupuncture has been shown to reduce electrocardiogram (ECG) evidence of myocardial ischemia while improving regional wall motion. See, Li P, Pitsillides K F, Rendig S V et al: "Reversal of reflex-induced myocardial ischemia by median nerve stimulation: a feline model of electroacupuncture," *Circulation* 97: 1186-94 (1998); Longhurst J C: "Central and peripheral neural mechanisms of acupuncture in myocardial ischemia," *Intl Congress Series* 1238:79-87(9) (2002). Various animal studies have shown improvement of experimental myocardial ischemia by the acupuncture or electroacupuncture of PC6 (sometimes alone but more often alongside other acupoints) Liu X Q, Lu S Q, Luo L: "Influence of acupuncture on epicardial monophasic action potential in vivo in dog with myocardial infarction," *Tianjin Journal of Traditional Chinese Medicine* 22: 480-481(2005).

Additionally, in a randomized controlled trial, electroacupuncture has been shown to alleviate cardiac ischemia-repurfusion injury in adult patients undergoing heart valve replacement surgery. Yang L, Yang J, Wang Q, et al.: "Cardioprotective effects of electroacupuncture pretreatment on patients undergoing heart valve replacement surgery: a randomized controlled trial," *Ann Thorac Surg* 89:781-6 (2010). Electroacupuncture was performed bilaterally at acupoints PC6, LU7, and LU2 once a day for 30 minutes over the five days preceding valve surgery. It is unclear what mechanism underlies these positive results; however, it may corroborate other research suggesting reduced oxygen demand.

The fourth of the cardiovascular conditions treated by the device and methods described herein is angina. In one of the first randomized trials to compare the effectiveness of acupuncture and sham acupuncture in patients with severe, stable angina pectoris resistant to medical treatment, Ballegaard et. al showed that the active treatment group had significantly higher dPRP and higher maximal PRP (note: "dPRP" is the difference in pressure rate-product between rest and maximum exercise; "PRP" is the pressure-rate product), which was interpreted as an increase in cardiac functional capacity. Ballegaard S, Jensen G, Pedersen F et al: "Acupuncture in severe, stable angina pectoris: a randomized trial," Acta Med Scand 220: 307-13 (1986). The investigators suggested that the change was caused by a decreased workload secondary to systemic vasodilation specific to the acupoints and not at the spinal cord level. The acupuncture was bilateral and manual applied at PC6, ST36, and UB14 (aka BL14).

In another study by Richter et al, individualized acupuncture was done on patients with stable angina with success. Richter A, Herlitz J, Hjalmarson A: "Effect of acupuncture in patients with angina pectoris," *Eur Heart J:* 12:175-8 (1991). The maximum workload until onset of chest pain was significantly increased. However, not much difference was observed in exercise capacity in comparison to the placebo therapy at the end of the acupuncture period. Investigators concluded some relief of myocardial ischemia, possibly by influencing coronary perfusion. While the acupuncture was individualized, five main points were used: PC6, HT5, UB15, UB20 and ST36; and, some additional points include HT7, LI4, LI11, and LV3.

Locations Stimulated

For treating any of the four cardiovascular disease conditions previously identified—heart failure, coronary artery disease (CAD) (which may also be referred to as coronary heart disease, or CHD), myocardial ischemia, and angina—the preferred acupoints that need to be stimulated by the EA device, i.e., the preferred target tissue locations at which electrical stimulation should be applied in accordance with a specified stimulation regimen, include at least one acupoint selected from the following group of nine acupoints, (or their underlying nerves, shown in brackets):

1. PC6 (Neiguan) [median nerve];
2. ST36 (Zusanli) [deep peroneal nerve];
3. BL14 (Jueyinshu), also referred to as UB14 (Jueyinshu) [4th and 5th thoracic nerve];
4. EX-HN1 (Sishencong) (one cm from GV20 (Baihui)) [near occipital nerve]
5. HT7 (Shenmen) [ulnar nerve];
6. HT5 (Tongli) [ulnar nerve];
7. LI11 (Quchi) [radial nerve];
8. LU2 (Yunmen) [anterior thoracic nerve]; and
9. LU7 (Lieque) [radial nerve].

The location of the above acupoints may be briefly summarized as: PC6 in the right or left wrist; ST36 on the anterior aspect of the left or right leg; on the tibialis anterior muscle; BL14 (also known as UB14, Jueyinshu) in the upper back region; EX-HN1 (one cm from Baihui GV20, on the top of the head); HT7 on the anteromedial aspect of the right or left wrist, radial to the flexor carpi ulnaris tendon, on the palmar wrist crease; HT5 on the anteromedial aspect of the forearm, radial to the flexor carpi ulnaris tendon; LI11 on the lateral aspect of the elbow; LU2 on the anterior thoracic region, in the depression of the infraclavicular fossa; and LU7 on the radial aspect of the forearm, between the tendons of the abductor pollicis longus and the extensor pollicis brevis muscles. All of these acupoints are illustrated and described on pages 25, 26, 29, 33, 39, 45, 64, 81, 84, 85, 99, 106, 154, 203 and 213 of *WHO Standard Acupuncture Point Locations* 2008, previously incorporated herein by reference. Selected portions of *WHO Standard Acupuncture Point Locations* 2008, including pages 25, 26, 29, 33, 39, 45, 64, 81, 84, 85, 99, 106, 154, 203 and 213 are included in Appendix D, as are three pages from another reference, Quirico P E, Pedrali T. *Teaching Atlas of Acupuncture*, Volume 1: *Channels and Points*. Georg Thieme Verlag. 2007; pages 184, 186 and 190 that further illustrate the location of acupoint GV20. Pages 180 through 196 of this *Teaching Atlas of Acupuncture* book by Quirico and Pedrali are incorporated herein by reference.

In some instances, it will be advantageous to stimulate a plurality (two or more) of acupoints together, i.e., implant a plurality of EA devices. For example, the acupoints PC6, LU7 and LU2 may be a good candidate for treating myocardial ischemia with a plurality of EA devices. Also, stimulation can be done bilaterally, i.e., two EA devices may be implanted, one at, e.g., acupoint PC6 in the right wrist, and one at acupoint PC6 in the left wrist.

Advantageously, the electrode(s) used with the EA device may be either integrated into the housing of the EA device, or located at the distal end of a very short lead (often referred to as a "pigtail" lead) or short boom that is attached to the housing of the EA device. Electrodes thus fashioned allow the form and shape of the EA housing itself to help anchor the electrodes in their desired position over, around, near or on the selected acupoint(s).

Operation of the EA device is simple and straightforward. Once implanted and activated, electrical stimulation pulses are applied to the desired acupoint at a low intensity, low frequency and low duty cycle in accordance with a pre-programmed stimulation regimen. Because the stimulation is done at low intensities (amplitudes), low frequencies, and low duty cycles, the power source employed in the implantable EA device can also be very small, and can operate for long periods without needing to be replaced, recharged or replenished.

Advantageously, when the power source carried in the EA device has run down, the entire EA device may be easily replaced through a simple surgical procedure that is typically no more invasive than removing a wart. Alternatively, in some embodiments of the invention, the power source carried in the EA device may be recharged or replenished in 20 to 30 minutes or less, thus providing operating power for the EA device for several additional weeks or months before needing to be recharged or replenished again.

Support for Selected Acupoints

Various studies and research have provided support for using one or more of these particular nine acupoints for treating heart failure, CAD, myocardial ischemia or angina. A summary of some of these studies and research is presented in the paragraphs that follow.

Sishencong (EX-HN).

Sishencong (EX-HN) is not a single point, but is a set or array of four acupoints, all located about one centimeter away from acupoint GV20 on the top of the head. For the acupoint(s) Sishencong (EX-HN), a study of nine healthy people showed that manual acupuncture applied 2 mm deep at the Sishencong acupoints located on the vertex of the head resulted in an increased high frequency percentage and decreased low frequency percentage of cardiac vagal and suppressed sympathetic activity, respectively. Wang J D, Kuo T, Yang C: "An alternative method to enhance vagal activities and suppress sympathetic activities in humans," *Autonomic Neuroscience: Basic and Clinical* 100: 90-95. (2002). In another study in 20 normal male volunteers, manual acupuncture at Sishencong was performed with similar success. Also, baroreceptor reflex was improved, which also suggests increased vagal and decreased sympathetic activity. Wang J D, "Manual Acupuncture of Sishencong Points Enhances Cardiac Vagal but Suppresses Cardiovascular Sympathetic Activities in Humans." URN etd-0729105-182922-61 (1998). [See www.etd.library.tcu.edu. Abstract Accessed Aug. 16, 2012.] The Sishencong points in acupuncture have historically been used to treat insomnia. Xie, L., Xie, L., Dong, X.: "124 cases of dyssomnia treated with acupuncture at sishencong points," *J. Tradit. Chin. Med.* 14, 171-173 (1994). Since people with high vagal and low sympathetic activity have a tendency to sleep, and since the Sishencong acupoints may be effective in treating insomnia, it was hypothesized that the mechanism of action relates to increased vagal and reduced sympathetic activity, which may be applied to other states of increased sympathetic activity and improvement of cardiovascular health.

Jueyinshu (BL14).

In a study published in Chinese, two groups of patients with coronary artery disease were needled at either BL14 and CV14 or BL15 and CV17. In both groups the patients' condition of myocardial ischemia improved, but in the former group it was more pronounced. Han Y, Zhang P, Ning M, et al.: "Influence of needling with the combination of back-shu and front-mu points in the heart and pericardium meridian on the electrocardiography of patients with coronary heart disease," *Chinese Acupuncture and Moxibustion* 1994-06. Abstract. (1994).

Shenmen (HT7).

In a study published in Chinese, electroacupuncture was performed on either HT7 or SI7 in two different groups of rabbits with experimental acute myocardial ischemia. Cai R L, Hu L, Zhou Y P, Wu Z J, Wang K M, Tang X M, Li M, Lu Z H: "Effects of electroacupuncture of "Shenmen" (HT 7) and "Zhizheng" (SI 7) on cardiac function and electrical activities of cardiac sympathetic nerve in acute myocardial ischemia rabbits," Zhen Ci Yan Jiu. 2007; 32(4): 243-6. Abstract (2007). Changes of heart rate, maximum rising rate and maximum descending rate of the left ventricular systolic pressure, and discharged of the cardiac sympathetic nerve were recorded. It was found that electroacupuncture of both HT7 and S17 can improve cardiac function and electrical activity of the cardiac sympathetic nerve in this acute myocardial ischemia model, and that the effects of HT7 are markedly better than S17. Additionally, in a rat model of gastric distension for which cardiovascular responses were examined, electroacupuncture at HT6 and HT7 significantly decreased the pressor response by 44%. Zhou W, Fu L W, Tjen-A-Looi S C, et al.: "Afferent mechanisms underlying stimulation modality-related modulation of acupuncture-related cardiovascular responses," *J Appl Physiol* 2005; 98:872-880 (2005).

Tongli (HT5).

In a study examining heart rate variability in healthy subjects, acupuncture at HT7 or HT7 and HT5 produced improvement in heart rate variability suggestive of improved sympathetic tone. Yang Y F, Chou C Y, Li T C, Jan Y M, Tang N Y, Hsieh C L.: "Different effects of acupuncture at shenmen (HT7)-Tongli (HT5) and Shenmen-Neiguan (PC6) points on heart rate variability in healthy subjects." *J Chin Med.* 2009; 20(3,4): 97-106 (2009).

Neiguan (PC6).

A body of evidence exists that shows the depressor effect on sympathetic activity of needling or electroacupuncture at PC6 (Neiguan). See, e.g., Li P and Longhurst J C, "Neural Mechanism of Electroacupuncture's Hypotensive Effects," Autonomic Neuroscience: Basic & Clinical 157:24-30 (2010). Since pharmacologic treatment of heart failure is focused on the normalization of sympathetic activity, such evidence for the treatment of hypertension also underlies EA stimulation for the treatment of cardiovascular diseases. In addition, there are some, mostly Chinese, studies wherein acupuncture or electroacupuncture is performed at PC6 (Neiguan) in coronary artery disease and angina. Xiao-min T, Ling Hu, Ke-ming L.: "Experimental study on electroacupuncture in "Neiguan" (PC6) on congestive heart failure rats model and its effect of AngII, ET, CGRP," *Journal of Chengdu University of Traditional Chinese Medicine.* 2007-01. Abstract (2007); Xu F H, Wang J M: "Clinical observation on acupuncture combined with medication for intractable angina pectoris," *Zhongguo Zhen Jiu.* 25(2): 89-91, Abstract (2005). Further, in a study published in Chinese, acupuncture at Neiguan was shown to regulate and improve heart rate variability in 20 coronary heart disease patients; this was evidenced by the LF/HF ratio. Shi X, Wang Z P, Liu K X. "Effect of acupuncture on heart rate variability in coronary heart disease patients," *Zhongguo Zhong Xi Yi Jie He Za Zhi* 15(9): 536-8. Abstract (1995).

Zusanli (ST36).

Similar to PC6 (Neiguan), ST36 (Zusanli) is a common point, often used amongst six or so other points, to affect the cardiovascular system. While it is frequently used alongside many points, its unique association with positive results for regulation of sympathetic activity suggests it is a key point. A small study which examines the use of ST36 for reduction of blood pressure with success is published by Chiu et al. (1997). Chiu Y J, Chi A, Reid I A et al.: "Cardiovascular and endocrine effects of acupuncture in hypertensive patients," *Clin. Exp. Hypertens* 19(7), 1047-1063 (1997). It is expected that the same method of stimulating ST36 manually or electrically and the resulting reductions in sympathetic activity are applicable to the disease states of coronary artery disease, angina, heart failure, and myocardial ischemia. Reduction in sympathetic activity will likely benefit these disease states outside of the benefit to blood pressure modulation.

Quchi (LI11).

A study was conducted wherein manual acupuncture and transcutaneous electrical nerve stimulation were applied at LI11 to a hypertension model in patients with some success in reducing blood pressure. Yuanhua W, Guangqu Z, Xingyou L, Lengxing O, Hongmei S, Bangqi W: "Effect of acupuncture at quchi and taichong on ET and ACE in the blood of the patient with hypertension and exploration of its efficacy," *Chinese Journal of Integrated Chinese and Western Medicine* 24:1080-83 (2004); Wen-jun W, Chao-yang M.: "Clinical Observation on therapeutic effect of electroacupuncture at Quchi (LI11) for treatment of essential hypertension. Chinese Acupuncture and Moxibustion." 2009: 29. Abstract (2009); Hongxing Z, Tangfa Z, Yueping L: "Control observation on acupuncture of Quchi (LI 11) and Medication in Transient Action of Decreasing Blood Pressure," *Chinese Acupuncture and Moxibustion.* 2011: 11. Abstract (2011); Jacobsson F, Himmelmann A, Bergbrant A et al.: "The effect of transcutaneous electric nerve stimulation in patients with therapy resistant hypertension," *J. Hum. Hypertens.* 14(12), 795-798 (2000).

Lieuque (LU7).

In a study examining the effect of electroacupuncture at PC6, LU7 and LU2, patients undergoing heart valve surgery had less cardiac ischemia-repurfusion injury. Yang L, Yang J, Wang Q, et al.: "Cardioprotective effects of electroacupuncture pretreatment on patients undergoing heart valve replacement surgery: a randomized controlled trial," *Ann Thorac Surg* 89:781-6 (2010). Like LI11 (Quchi), LU7 (Lieuque) overlies the radial nerve. While the evidence supporting stimulation of LU7 alone for cardiovascular benefit is limited, its position over the radial nerve and its use in insomnia are factors indicating it should be included in the group of acupoints where electroacupuncture stimulation may be applied to treat cardiovascular disease, primarily by successfully reducing sympathetic activity.

Yunmen (LU2).

Yunmen (LU2), like its meridian point Lieuque, (LU7), is also used to treat insomnia. Because it is suggested that the mechanism by which Lieuque (LU7) positively effects insomnia is through reduction in sympathetic activity, it is believed that Yunmen (LU2) may also have an application in cardiovascular health.

To facilitate an understanding of the methods and systems described herein, an exemplary EA System will next be described in two sections, Section I and Section II. Section I will describe the invention in connection with the detailed description of FIGS. 17-31, which relate to general principles and concepts associated with the invention. Section II will then provide, in detail, a specific example of the invention in connection with the description of FIGS. 1-16.

I. General Principles and Concepts

An exemplary EA System 10 will next be described in connection with FIGS. 17-31. First, with respect to FIG. 17, and subsequently with respect to other figures which show, and the accompanying description describes, more details and features associated with the EA System 10 are illustrated and described. As has already been indicated, a preferred application of the EA System is to treat cardiovascular disease. But, as has also previously been indicated, the EA System has applicability to treating other conditions, illnesses and deficiencies other than just cardiovascular disease. The scope of the invention should be ascertained from the claims.

Figure 17:
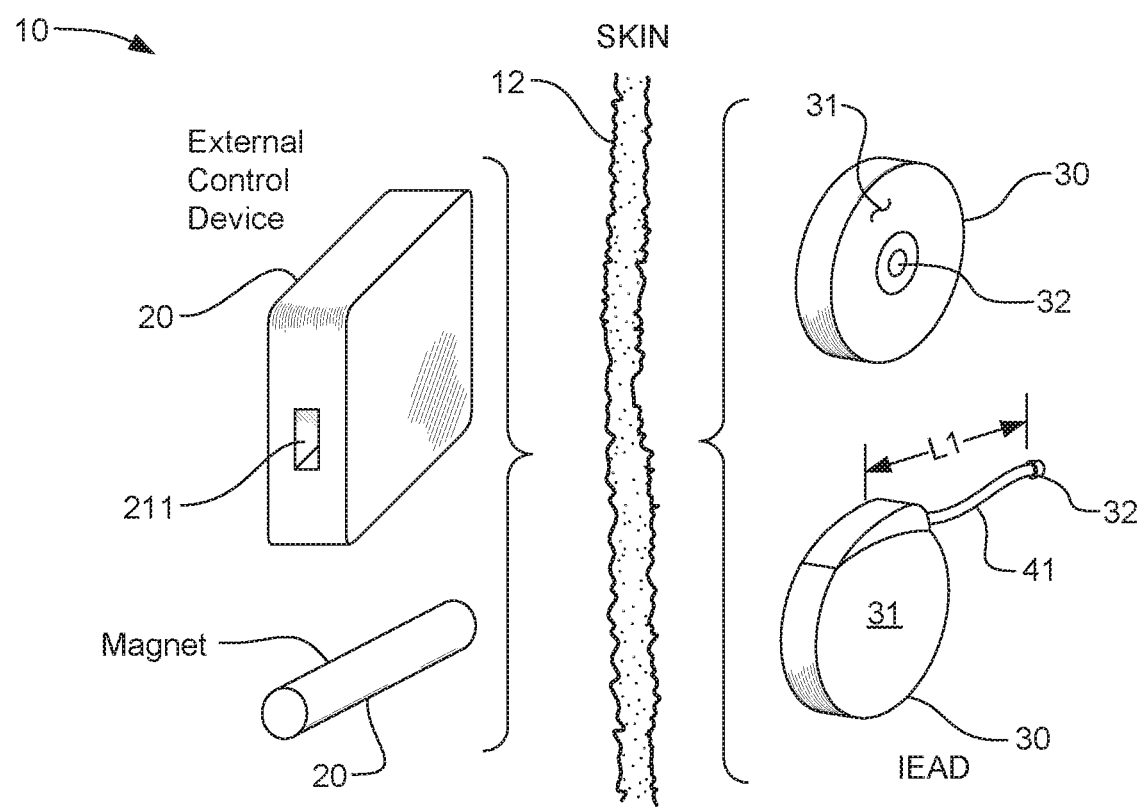

As seen in FIG. 17, the EA System 10 includes two main components: (1) an External Control Device (ECD) 20 and (2) an Implantable ElectroAcupuncture Device 30, or IEAD 30. (It is noted that in Section II below, the IEAD is also referred to using the reference numeral 100. Thus, whether it is referred to as the IEAD 30 or the IEAD 100, it is essentially the same or a similar element.) Two versions of the ECD 20 are included in FIG. 17. A first is a handheld electronic device that includes a port 211 enabling it to be coupled to a computer, or similar processor. A second is a magnet, typically a cylindrical magnet. Two versions of an IEAD are also included in FIG. 17, either one of which may be used. One embodiment (top right of FIG. 17) has an electrode 32 that forms an integral part of the case 31 of the IEAD 30; and the other embodiment (lower right of FIG. 1A) has an electrode 32 that is located at the end of a short lead 41 attached to the IEAD 30.

The IEAD 30, in one embodiment, is disc shaped, having a diameter of about 2 to 3 cm, and a thickness of about 2 to 4 mm. It is implanted just under the skin 12 of a patient near a desired acupuncture site. Other shapes and sizes for the IEAD 30 may also be used, as described in more detail below. The desired acupuncture site is also referred to herein as a desired or target "acupoint." For reducing heart failure, coronary artery disease (CAD), myocardial ischemia or angina, the target acupoints of interest include acupoints PC6, ST36, BL14 (also referred to as UB14), EX-HN1 (located approximately one centimeter from GV20), HT7, HT5, LI11, LU2 and LU7.

The IEAD 30 includes an electrode 32 which may take various forms. At least a portion of the electrode, in some embodiments, may include a rod-like body and a pointed or tapered tip, thereby resembling a needle. Because of this needle-like shape, and because the electrode 32 replaces the needle used during conventional acupuncture therapy, the electrode 32 may also be referred to herein as a "needle electrode". However, an alternate and preferred electrode form to replace a "needle electrode" is a smooth surface electrode, without any sharp or pointed edges.

For the embodiment shown in top right portion of FIG. 17, and for the IEAD 30, the electrode 32 forms an integral part of the housing 31 of the IEAD 30, and is located on an underneath side of the IEAD housing approximately in the center of the housing. As used here, "underneath" means the housing side farthest from the skin layer 12, or deepest in the body tissue. Other embodiments may incorporate an electrode that is not centered in the housing 31, and that is not even on the underneath side of the housing, but is rather on an edge of the housing 31. Alternatively, as shown in the bottom right of FIG. 17, the electrode 32 may be located at the distal end of a short lead 41, e.g., nominally 10-20 mm long, but in some instances it may be up to 50 mm long, implanted with a strain relief loop to isolate movement of the case from the electrode. The proximal end of the lead is attached to the IEAD 30 along an edge of the IEAD housing 31 or at a suitable connection point located on the underneath side of the IEAD 30. Alternate configurations for attaching the proximal end of the lead 41 to the IEAD housing 31 are illustrated in Appendix F.

When implanted, the IEAD 30 is positioned such that the electrode 32 resides near, directly over, or on, the desired acupoint. For those embodiments where the electrode 32 forms an integral part of the housing 31 of the IEAD 30, there is thus no need for a long lead that must be tunneled through body tissue or blood vessels in order to place the electrode at the desired acupoint. Moreover, even for those embodiments where a very short lead may be employed between the IEAD 30 and the electrode 32, the tunneling required, if any, is orders of magnitude less than the present state of the art. In fact, with an electrode lead of between 20 mm and 50 mm in length, it is probable that no tunneling will be required. Further, because the electrode either forms an integral part of the IEAD housing 31, or is attached to the IEAD housing using a very short pigtail lead, the entire IEAD housing 31 serves as an anchor to hold or secure the electrode 32 in its desired location.

For the embodiment depicted in the top right of FIG. 17 and as mentioned above, the electrode 32 is located in the center of the underneath side of the IEAD 30. As explained in more detail below, this positioning of the electrode 32 is only exemplary, as various types of electrodes may be employed, as well as various numbers of electrodes and relative positioning. See, e.g., FIGS. 20 through 21C, and accompanying text, presented below. See also Appendix A and Appendix B.

Still referring to FIG. 17, the EA System 10 also includes an external control unit, or ECD, 20. The role that the ECD 20 plays in the operation of the EA system varies as a function of which embodiment of the EA System is being used. A USB port 211, located on one side of the ECD, allows it to be connected to a PC or notebook computer for diagnostic, testing, or programming purposes. Other ports or connectors may also be used on the ECD 20, as needed by the various embodiments employed. In its simplest form, however, the ECD 20 may take the form of a handheld magnet, described in more detail below in conjunction with a specific example of the invention.

FIG. 18 is a Table that highlights the main embodiments of the EA System 10, and provides a summary description of the functions performed by the External Controller 20 and IEAD 30 in each embodiment. It is important to note that the list of embodiments identified in FIG. 18 is not a complete list, but is only representative of four of the many embodiments that could be employed. Thus, the embodiments highlighted in FIG. 18 include, but are not limited to:

Embodiment I

Embodiment I comprises a fully implantable EA System wherein the IEAD 30 provides the desired stimulation as controlled by an internal program, or stimulation regime, programmed into its circuits. When thus configured, the External Controller 20 is used in Embodiment I only as a programmer to program the operating parameters of the IEAD 30. When the IEAD 30 is operating, all of its operating power is obtained from a power source carried within the IEAD 30.

Embodiment II

Embodiment II is essentially the same as Embodiment I except that the External Controller 20 is used, when needed, to both program the IEAD 30 and to recharge or replenish a rechargeable and/or replenishable power source carried within the IEAD 30.

Embodiment III

In Embodiment III, all or most all of the functions of the EA System are performed within the External Controller 20 except for delivery of the desired stimuli to the desired acupoint through the electrode 32. Hence, when the EA System operates using Embodiment III, the External Controller 20 must always be present and RF-coupled or magnetically-coupled to the IEAD 20. That is, in Embodiment III, the External Controller 20 generates the stimulation energy at the desired time, duration and intensity. Then, it sends, i.e., transmits, this energy through the skin 12 to the implantable electroacupuncture stimulator 30. Such transmission of energy through the skin is typically done through electromagnetic coupling, e.g., inductive coupling, much like a transformer couples energy from its primary coil to its secondary coil. For coupling through the skin, the primary coil is located in the External Controller 20 and the secondary coil is located in the IEAD 30. The IEAD 30 receives this energy and simply passes it on to the electrode 32 via interconnecting conductive traces or wires. Embodiment III is particularly useful for diagnostic and data-gathering purposes, but can also be used by a patient who does not mind occasionally wearing an external device positioned on his or her skin over the location where the IEAD is implanted whenever the EA System is operational.

Embodiment IV

In Embodiment IV, the EA system is a fully, self-contained, implantable IEAD except for the use of an external "passive" control element, such as a magnet. The external control element is used to perform very basic functions associated with the IEAD, such as turning the IEAD OFF or ON, changing the intensity of stimulus pulses by a small amount, slightly modifying the timing of stimulation sessions, resetting the parameters of the stimulation regimen back to default values, and the like.

Figure 19:
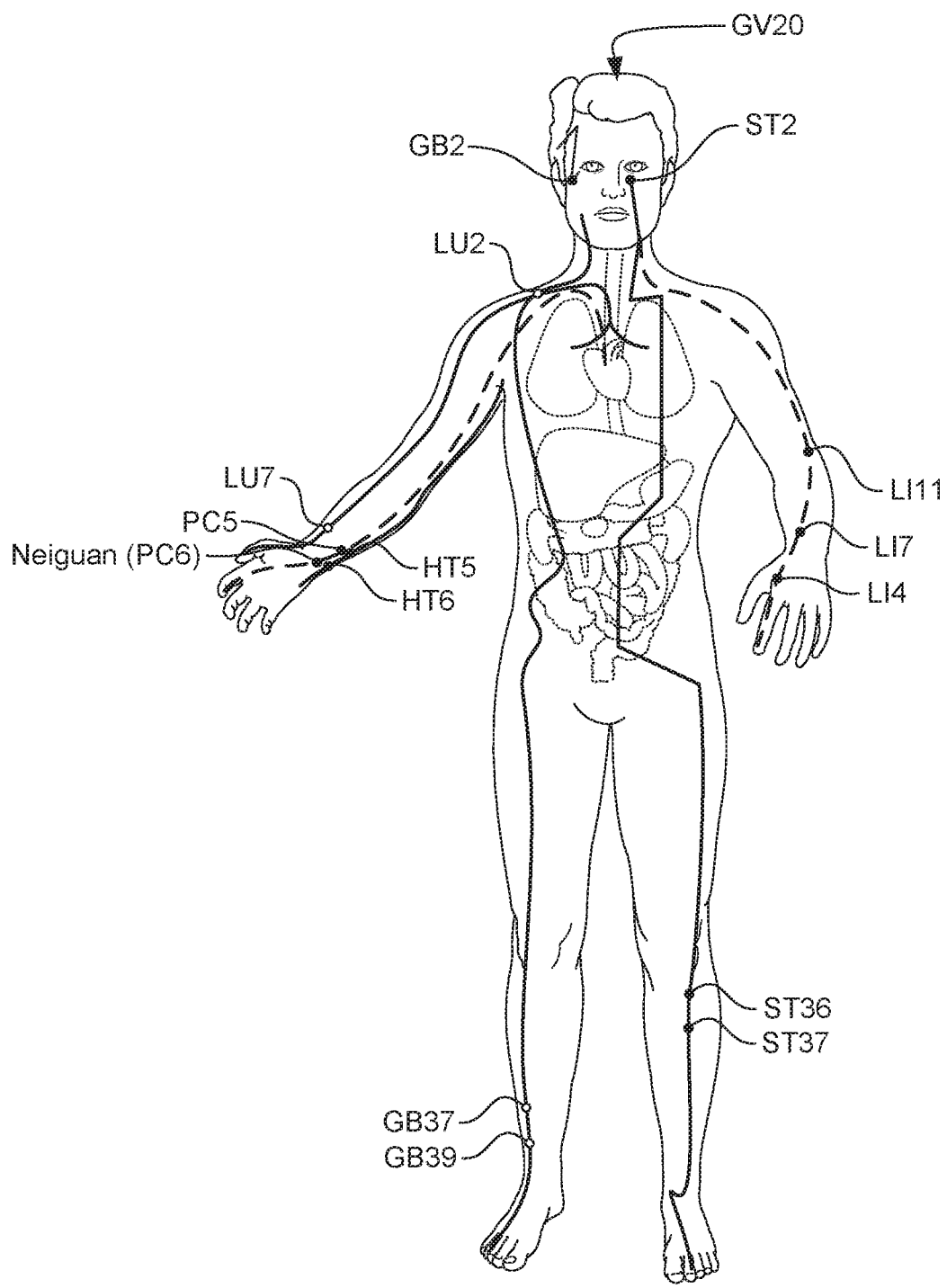

Next, with reference to FIG. 19, there is shown an illustration or representation of the human body. This illustration shows the location of effective and ineffective acupoints used in electroacupuncture (EA) for the treatment of various diseases and conditions of a patient, including hypertension, heart failure, CAD, myocardial ischemia or angina. These acupoints have been identified based on research performed by Peng Li and John C. Longhurst, as documented in Li et al., "Neural Mechanism of Electroacupuncture's Hypotensive Effects", *Autonomic Neuroscience: Basic and Clinical* 157 (2010) 24-30, which article is incorporated herein by reference. The EA System described herein utilizes some of the acupoints identified by Li and Longhurst, inter alia, as well as other acupoints identified through independent research, as being effective for the treatment of heart failure, CAD, myocardial ischemia or angina. According to the Applicants' research, nine such acupoints exist: PC6, ST36, BL14 (also referred to as UB14), EX-HN1 (located approximately one centimeter from GV20), HT7, HT5, LI11, LU2 and LU7.

One stimulation regime stimulates the selected target acupoint over several weeks or months, e.g., over a four to eight week stimulation interval. This four to eight week stimulation interval may then be followed by, e.g., a two to four week interval of no stimulation. Then the cycle begins again: four to eight weeks of stimulation, followed by two to four weeks of no stimulation.

Another stimulation regime stimulates the selected target acupoint over several months or years, but at a very low duty cycle, e.g., applying a stimulation session have a duration of 30 minutes only once or twice a week. For purposes of the present invention, Applicants have determined that if a stimulation session has a duration of T3 minutes, and if the time between stimulation sessions is T4 minutes, the duty cycle, or ratio of T3/T4, should be no greater than 0.05.

One advantage of providing stimulation pulses using a low duty cycle, as described above, is that the power source of the IEAD 30 is able to power operation of the IEAS over long periods of time. Through careful power management, detailed more fully below in conjunction with the description of a specific example, the IEAD 30 may operate for several years.

Turning next to FIGS. 20, 20A and 20B, a mechanical drawing of one embodiment of the housing 31 of the implantable electroacupuncture stimulator 30 is illustrated, along with various types of electrodes that may be used therewith. In a first embodiment, as seen in FIG. 20, the housing 31 of the IEAD 30 is preferably disc-shaped, having a diameter "d1" and width "w1". The housing 31 is made from a suitable body-tissue-compatible (biocompatible) metal, such as Titanium or stainless steel, having a thickness of 0.2 to 1.0 mm. An electrode 32 resides at the center of the underneath side of the housing 31. The underneath side of the housing 31 is the side facing out of the paper in FIG. 20, and is the side that is farthest away from the surface of the skin when the stimulator device is implanted in a patient.

The electrode 32 is surrounded by a ceramic or glass section 34 that electrically insulates the electrode 32 from the rest of the housing 31. This ceramic or glass 34 is firmly bonded (brazed) to the metal of the housing 31 to form an hermetic seal. Similarly, a proximal end 35 of the electrode 34, best seen in the sectional views of FIG. 20A or 20B, passes through the ceramic or glass 34, also forming an hermetic seal. The resultant structure resembles a typical feed-through pin commonly used in many implantable medical devices, and allows electrical connection to occur between electrical circuitry housed within the hermetically-sealed housing and body tissue located outside of the hermetically-sealed housing.

In the embodiment of the housing 31 shown in FIGS. 20, 20A and 20B, the electrode 32 is shown formed to have a narrow tip, much like a needle. Hence, the electrode 32 is sometimes referred to as a needle electrode. It is commonly taught that a needle electrode of this type generally allows the electric fields associated with having a current flowing out of or into the needle tip to be more sharply focused, and thereby allows the resultant current flow through the body tissue to also be more sharply focused. This helps the electrical stimulation to be applied more precisely at the desired acupuncture point. Further, because most acupoints tend to exhibit a lower resistance than do non-acupoints, the amount of power required to direct a stimulation current through the acupoint is lower, thereby helping to conserve power.

However, as will be explained in more detail below in conjunction with Applicant's specific example (Section II), Applicant's preferred electrode shape is smooth, and symmetrical, which shape and configuration allow the resultant electric fields to deeply penetrate into the desired target tissue.

As is known in the art, all electrical stimulation requires at least two electrodes, one for directing, or sourcing, the stimulating current into body tissue, and one for receiving the current back into the electronic circuitry. The electrode that receives the current back into the electronic circuit is often referred to as a "return" or "ground" electrode. The metal housing 31 of the IEAD 30 may function as a return electrode during operation of the IEAD 30.

FIG. 20A is a sectional view, taken along the line A-A of FIG. 20, that shows one embodiment of the IEAD housing wherein the needle electrode 32 resides in a cavity 37 formed within the underneath side of the IEAD housing 31.

FIG. 20B is a sectional view, taken along the line A-A of FIG. 20, and shows an alternative embodiment of the underneath side of the IEAD wherein the needle or other electrode 32 forms a bump that protrudes out from the underneath surface of the IEAD a short distance.

FIG. 20C is a sectional view, taken along the line A-A of FIG. 20, and shows yet another alternative embodiment where a short lead 41, having a length L1, extends out from the housing 31. The electrode 32, which may be formed in many shapes, is located at a distal end of the lead 41. The shapes of the electrode, for example, may be a ball, cone or tapered cylindrical, ring, bullet shaped or full or half cuffed, with electrode anchoring features. See, e.g., Appendix F, where various shaped electrodes at the end of a short pigtail lead are illustrated. The length L1 of this short electrode is nominally 10-20 cm, but may extend as long as 50 mm. A proximal end of the lead 41 attaches to the housing 31 of the IEAD 30 through a feed-through type structure made of metal 35 and glass (or ceramic) 34, as is known in the art.

Next, with reference to FIGS. 21, 21A, 21B, and 21C, there is shown an embodiment of the IEAD 30 that shows the use of four needle electrodes integrated within the housing 31 of an IEAD 30. The needle electrodes 32 have a tip 33 that protrudes away from the surface of the housing 31 a short distance. A base, or proximal, portion of the needle electrodes 32 is embedded in surrounding glass or ceramic 34 so as to form an hermetic bond between the metal and ceramic. A proximal end 35 of the needle electrode 32 extends into the housing 31 so that electrical contact may be made therewith. The ceramic or glass 34 likewise forms a metallic bond with the edge of the housing 31, again forming an hermetic bond. Thus, the needle electrodes 32 and ceramic 34 and metal housing 31 function much the same as a feed-through pin in a conventional implantable medical device housing, as is known in the art. Such feed-through pin allows an electrical connection to be established between electrical circuitry housed within the hermetically-sealed housing 31 and body tissue on the outside of the hermetically sealed housing 31.

Having four needle electrodes arranged in a pattern as shown in FIG. 21 allows a wide variation of electric fields to be created emanating from the tip 33 of each needle electrode 32 based on the magnitude of the current or voltage applied to each electrode. That is, by controlling the magnitude of the current or voltage at each tip 32 of the four electrodes, the resulting electric field can be steered to a desired stimulation point, i.e., to the desired electroacupuncture (EA) point.

FIG. 21C is a also a sectional view, taken along the line B-B of FIG. 21, that shows yet another embodiment of the EA device where the electrodes comprise small conductive pads 47 at or near the distal end of a flex circuit cable 45 that extends out from the underneath surface of the IEAD a very short distance. To facilitate a view of the distal end of the flex circuit cable 45, the cable is shown twisted 90 degrees as it leaves the underneath surface of the IEAD 30. When implanted, the flex circuit cable 45 may or may not be twisted or have a strain relief loop, depending upon the relative positions of the IEAD 30 and the target acupoint to be stimulated. As can be seen in FIG. 21C, at the distal end of the flex circuit cable 45 the four electrodes 32 are arranged in a square pattern array. Other arrangements of the electrodes 32 may also be employed, a linear array, a "T" array, and the like. Many other alternate electrode configurations are illustrated, e.g., in Appendix A and Appendix B.

While only one or four electrodes 32 is/are shown as being part of the housing 31 or at the end of a short lead or cable in FIGS. 20 and 21, respectively, these numbers of electrodes are only exemplary. Any number of electrodes, e.g., from one to eight electrodes, that conveniently fit on the underneath side or edges of an IEAD housing 31, or on a paddle array (or other type of array) at the distal end of a short lead, may be used. The goal is to get at least one electrode (whether an actual electrode or a virtual electrode—created by combining the electric fields emanating from the tips of two or more physical electrodes) as close as possible to the target EA point, or acupoint. When this is done, the EA stimulation should be more effective.

Next, with reference to FIGS. 22A through 22E, various alternate shapes of the housing 31 of the IEAD 30 that may be used with an EA System 10 are illustrated. The view provided in these figures is a side sectional view, with at least one electrode 32 also being shown in a side sectional view. In FIGS. 22A through 22D, the electrode 32 is electrically insulated from the housing 31 by a glass or ceramic insulator 34. A portion of the electrode 32 passes through the insulator 34 so that a proximal end 35 of the electrode 32 is available inside of the housing 31 for electrical contact with electronic circuitry that is housed within the housing 31.

In FIG. 22A, the housing 31 is egg shaped (or oval shaped). A bump or needle type electrode 32 protrudes a small distance out from the surface of the housing 31. While FIG. 22A shows this electrode located more or less in the middle of the surface of the egg-shaped housing, this positioning is only exemplary. The electrode may be located anywhere on the surface of the housing, including at the ends or tips of the housing (those locations having the smallest radius of curvature).

In FIG. 22B, the housing 31 of the IEAD 30 is spherical. Again, a bump or needle-type electrode 32 protrudes out a small distance from the surface of the housing 31 at a desired location on the surface of the spherical housing. The spherical housing is typically made by first making two semi-spherical housings, or shells, and then bonding the two semi-spherical housings together along a seam at the base of each semi-spherical shell. The electrode 32 may be located at some point along or near this seam.

In FIG. 22C, the housing 31 is semi-spherical, or dome shaped. A bump or needle electrode 32 protrudes out from the housing at a desired location, typically near an edge of the base of the semi-spherical or dome-shaped housing 31.

In FIG. 22D, the housing is rectangular in shape and has rounded edges and corners. A bump or needle electrode 32 protrudes out from the housing at a desired location on the underneath side of the housing, or along an edge of the housing. As shown in FIG. 22D, one location for positioning the electrode 32 is on the underneath side near the edge of the housing.

In FIG. 22E, the housing 31 is key shaped, having a base portion 51 and an arm portion 53. FIG. 22E includes a perspective view "A" and a side sectional view "B" of the key-shaped housing 31. As shown, the electrode 32 may be positioned near the distal end of the arm portion 53 of the housing 31. The width of the arm portion 53 may be tapered, and all the corners of the housing 31 are rounded or slanted so as to avoid any sharp corners. The key-shaped housing shown in FIG. 22E, or variations thereof, is provided so as to facilitate implantation of the IEAD 30 through a small incision, starting by inserting the narrow tip of the arm portion 53, and then sliding the housing under the skin as required so that the electrode 32 ends up being positioned over, adjacent or on the desired acupoint.

In lieu of the bump or needle-type electrodes 32 illustrated in FIGS. 22A through 22C, a smooth, flat or other non-protruding electrode 32 may also be used.

It is to be noted that while the various housing shapes depicted in FIGS. 22A through 22E have a bump or needle-type electrode (and which could also be a flat or smooth electrode as noted in the previous paragraph) that form an integral part of the IEAD housing 31, electrodes at the distal end of a short lead connected to the IEAS housing may also be employed with any of these housing shapes.

It is also to be emphasized that other housing shapes could be employed for the IEAD 30 other than those described. For example, reference is made to the alternate case shapes shown in Appendix E. The invention described and claimed herein is not directed so much to a particular shape of the housing 31 of the IEAD 30, but rather to the fact that the IEAD 30 need not provide EA stimulation on a continuous basis, but may operate using a very low duty cycle, and therefore the power source carried in the IEAD need not be very large, which in turn allows the IEAS housing 31 to be very small. The resulting small IEAD 30 may then advantageously be implanted directly at or near the desired acupoint, without the need for tunneling a lead and an electrode(s) over a long distance, as is required using prior art implantable electroacupuncture devices. Instead, the small IEAD 30 used with the present invention applies its low duty cycle, non-continuous EA stimulation regime at the desired acupoint without the use of long leads and extensive tunneling, which stimulation regime applies low intensity, low frequency and low duty cycle stimulation at the designated acupoint over a period of several years in order to slowly but surely modulate and reduce cardiovascular disease (or whatever other condition, illness or deficiency is being treated).

Figure 4:
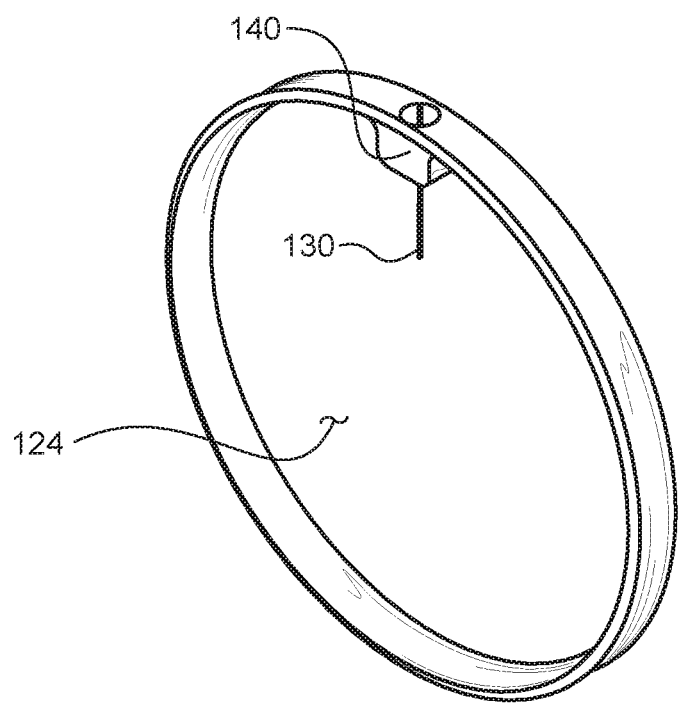
Figure 23:
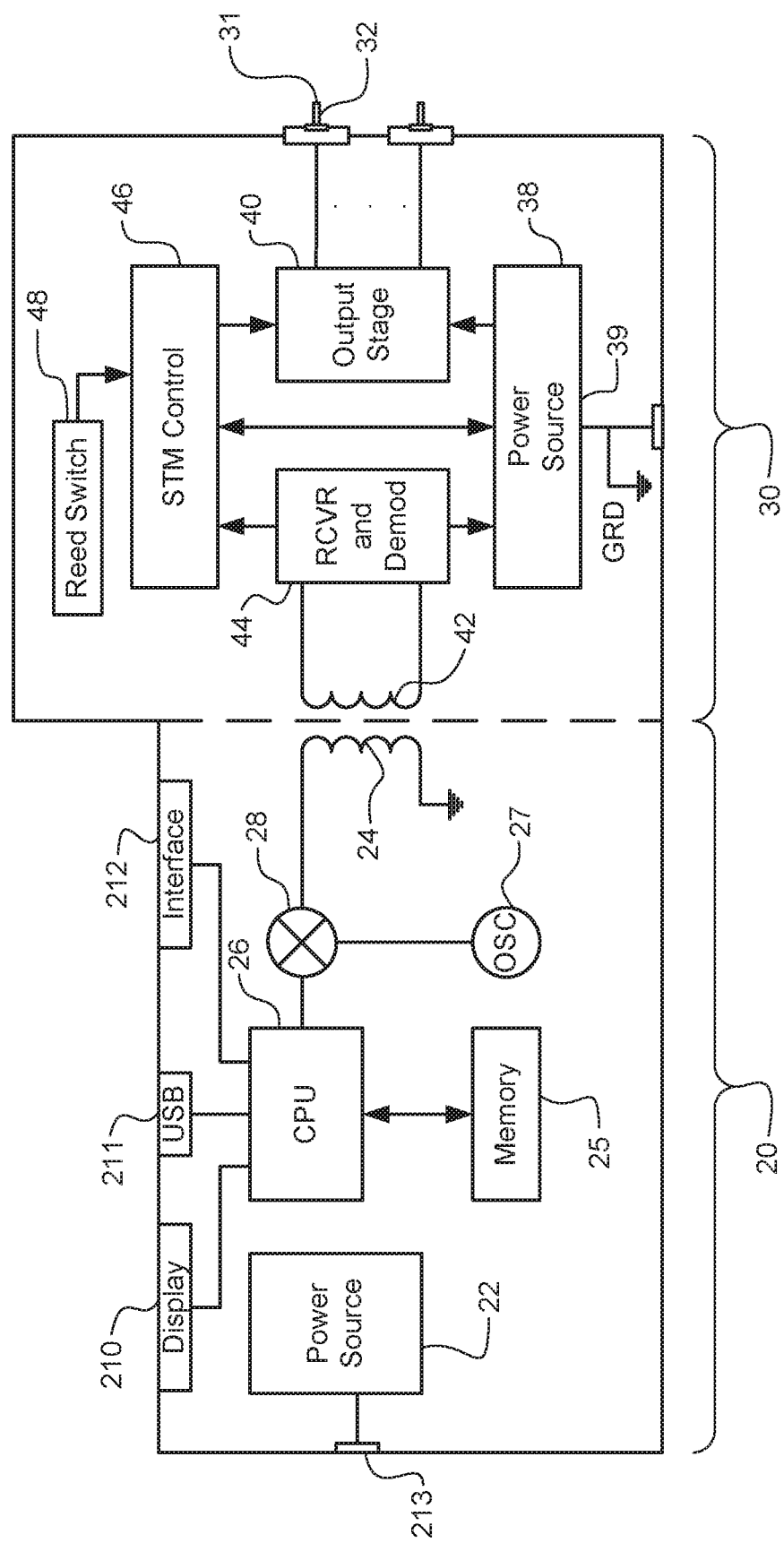

Turning next to FIG. 23, an electrical functional block diagram of the electrical circuitry and electrical components housed within the IEAD 30 and the External Controller 20 is depicted. The functional circuitry shown to the right of FIG. 4 is what is typically housed within the IEAD 30. The functional circuitry shown to the left of FIG. 4 is what is typically housed within the External Control Device 20, also referred to as an External Controller 20. How much circuitry is housed within the IEAD 30 and how much is housed within the External Controller 20 is a function of which embodiment of the EA System 10 is being used.

It is to be noted and emphasized that the circuitry shown in FIG. 23, and in the other figures which show such circuitry, is intended to be functional in nature. In practice, a person of skill in the electrical, bioelectrical and electronic arts can readily fashion actual circuits that will perform the intended functions. Such circuitry may be realized, e.g., using discrete components, application specific integrated circuits (ASIC), microprocessor chips, gate arrays, or the like.

As seen in FIG. 23, the components used and electrical functions performed within the IEAD 30 include, e.g., a power source 38, an output stage 40, an antenna coil 42, a receiver/demodulator circuit 44, a stimulation control circuit 46, and a reed switch 48. The components used and electrical functions performed with the External Controller 20 include, e.g., a power source 22, a transmission coil 24, a central processing unit (CPU) 26, a memory circuit 25, a modulator circuit 28 and an oscillator circuit 27. The External Controller 20 also typically employs some type of display device 210 to display to a user the status or state of the External Controller 20. Further, an interface element 212 may be provided that allows, e.g., a means for manual interface with the Controller 210 to allow a user to program parameters, perform diagnostic tests, and the like. Typically, the user interface 212 may include keys, buttons, switches or other means for allowing the user to make and select operating parameters associated with use of the EA System 10. Additionally, a USB port 211 is provided so that the External Controller 20 may interface with another computer, e.g., a laptop or notebook computer. Also, a charging port 213 (which may also be in the form of a USB port) allows the power source 22 within the External Controller 20 to be recharged or replenished, as needed.

In operation, the Stimulation Control Circuit 46 within the IEAD 30 has operating parameters stored therein that, in combination with appropriate logic and processing circuits, cause stimulation pulses to be generated by the Output Stage 40 that are applied to at least one of the electrodes 32, in accordance with a programmed or selected stimulation regime. The operating parameters associated with such stimulation regime include, e.g., stimulation pulse amplitude, width, and frequency. Additionally, stimulation parameters may be programmed or selected that define the duration of a stimulation session (e.g. 15, 30, 45 or 60 minutes), the frequency of the stimulation sessions (e.g., daily, twice a day, three times a day, once every other day, etc.) and the number of continuous weeks a stimulation session is applied, followed by the number of continuous weeks a stimulation session is not applied.

The Power Source 38 within the IEAD 30 may comprise a primary battery, a rechargeable battery, a supercapacitor, or combinations or equivalents thereof. For example, one embodiment of the power source 38, as discussed below in connection with FIG. 7, may comprise a combination of a rechargeable battery and a supercapacitor.

When describing the power source 38, the terms "recharge", "replenish", "refill", "reenergize", and similar terms (or variations thereof), may be used interchangeably to mean to put energy into a depleted reservoir of energy. Thus, e.g., a rechargeable battery when it is run down is recharged. A supercapacitor designed to hold a large volume of electrical charge has its store of electrical charge replenished. A power source that comprises a combination of a rechargeable battery and a supercapacitor, or similar devices, is reenergized. In other words, as the stored energy within an EA device is consumed, or depleted, the store of energy within the EA device, in some embodiments, may be replenished, or the energy reservoir within the EA device is refilled. In other embodiments, the EA device may simply and easily be replaced.

The antenna coil 42 within the IEAD 30, when used (i.e., when the IEAD 30 is coupled to the External Controller 20), receives an ac power signal (or carrier signal) from the External Controller 20 that may be modulated with control data. The modulated power signal is received and demodulated by the receiver/demodulator circuit 44. (The receiver/demodulator circuit 44 in combination with the antenna coil 42 may collectively be referred to as a receiver, or "RCVR".) Typically the receiver/demodulator circuit 44 includes simple diode rectification and envelope detection, as is known in the art. The control data, obtained by demodulating the incoming modulated power signal, is sent to the Stimulation Control circuit 46 where it is used to define the operating parameters and generate the control signals needed to allow the Output Stage 40 to generate the desired stimulation pulses.

It should be noted that the use of coils 24 and 42 to couple the external controller 20 to the IEAD 30 through, e.g., inductive or RF coupling, of a carrier signal is not the only way the external controller and IEAS may be coupled together, when coupling is needed (e.g., during programming and/or recharging). Optical or magnetic coupling, for example, may also be employed.

The control data, when present, may be formatted in any suitable manner known in the art. Typically, the data is formatted in one or more control words, where each control word includes a prescribed number of bits of information, e.g., 4 bits, 8 bits, or 16 bits. Some of these bits comprise start bits, other bits comprise error correction bits, other bits comprise data bits, and still other bits comprise stop bits.

Power contained within the modulated power signal is used to recharge or replenish the Power Source 38 within the IEAD 30. A return electrode 39 is connected to a ground (GRD), or reference, potential within the IEAD 30. This reference potential may also be connected to the housing 31 (which housing is sometimes referred to herein as the "case") of the IEAD 30.

A reed switch 48 may be employed within the IEAD 30 in some embodiments to provide a means for the patient, or other medical personnel, to use a magnet placed on the surface of the skin 12 of the patient above the area where the IEAD 30 is implanted in order to signal the IEAS that certain functions are to be enabled or disabled. For example, applying the magnet twice within a 2 second window of time could be used as a switch to manually turn the IEAD 30 ON or OFF.

The Stimulation Control Circuit 46 used within the IEAD 30 contains the appropriate data processing circuitry to enable the Control Circuit 46 to generate the desired stimulation pulses. More particularly, the Control Circuit 46 generates the control signals needed that will, when applied to the Output Stage circuit 40, direct the Output Stage circuit 40 to generate the low intensity, low frequency and low duty cycle stimulation pulses used by the IEAD 30 as it follows the selected stimulation regime. In one embodiment, the Control circuit 46 may comprise a simple state machine realized using logic gates formed in an ASIC. In other embodiments, it may comprise a more sophisticated processing circuit realized, e.g., using a microprocessor circuit chip.

In the External Controller 20, the Power Source 22 provides operating power for operation of the External Controller 20. This operating power also includes the power that is transferred to the power source 38 of the IEAD 30 whenever the implanted power source 38 needs to be replenished or recharged. Because the External Controller 20 is an external device, the power source 22 may simply comprise a replaceable battery. Alternatively, it can comprise a rechargeable battery.

The External Controller 20 generates a power (or carrier) signal that is coupled to the IEAD 30 when needed. This power signal is typically an RF power signal (an AC signal having a high frequency, such as 40-80 MHz). An oscillator 27 is provided within the External Controller 20 to provide a basic clock signal for operation of the circuits within the External Controller 20, as well as to provide, either directly or after dividing down the frequency, the AC signal for the power or carrier signal.

The power signal is modulated by data in the modulator circuit 28. Any suitable modulation scheme may be used, e.g., amplitude modulation, frequency modulation, or other modulation schemes known in the art. The modulated power signal is then applied to the transmitting antenna or coil 24. The external coil 24 couples the power-modulated signal to the implanted coil 42, where the power portion of the signal is used to replenish or recharge the implanted power source 38 and the data portion of the signal is used by the Stimulation Control circuit 46 to define the control parameters that define the stimulation regime.

The memory circuit 25 within the External Controller 20 stores needed parameter data and other program data associated with the available stimulation regimes that may be selected by the user. In some embodiments, only a limited number of stimulation regimes are made available for the patient to use. Other embodiments may allow the user or other medical personnel to define one or more stimulation regimes that is/are tailored to a specific patient.

Figure 24:
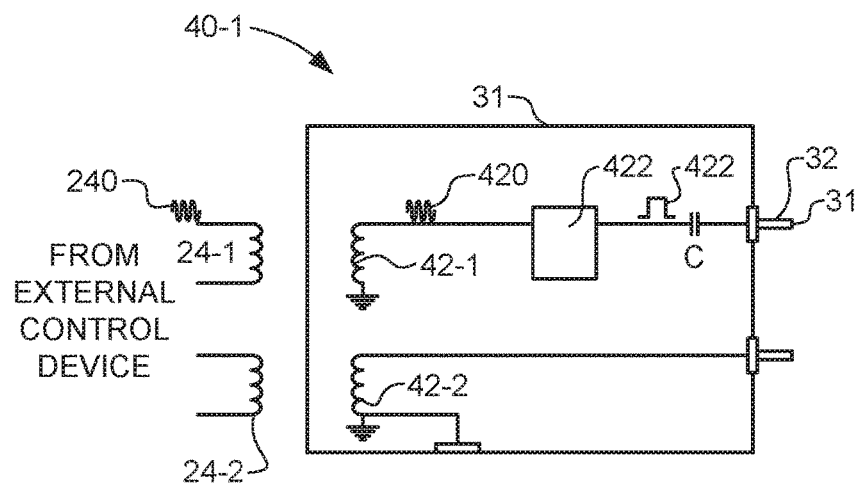

Turning next to FIG. 24, there is shown a functional diagram of an Output Stage 40-1 that may be used within the IEAD 30 for Embodiment III (See FIG. 18 and accompanying text for a description of Embodiment III). The Output Stage 40-1 is basically a pass-through circuit, wherein the entire IEAD 30 comprises nothing more than an electrode 32 connected to a coil 42-1, all of which is carried within an IEAD housing 31. In some embodiments, some simple passive filtering circuitry 424 may also be used to filter and shape the signal being passed from the coil 42-1 to the electrode(s) 32. Such a simple IEAD housing 31 allows the mechanical functions of the IEAD 30 (size, implant location, effectiveness of EA stimulation, etc.) to be implanted and fully tested without initially incurring the additional expenses associated with a fully functional IEAD 30.

As indicated in the previous paragraph, the function of the simplified IEAD 30 shown in FIG. 24 is to pass the signal received at the antenna coil 42-1 on to the electrode(s) 32. More particularly, a signal burst 240, when applied to a coil 24-1 in the External Controller 20, is electromagnetically (e.g., inductively) coupled to the coil 42-1 within the Output Stage 40-1 of the IEAD 30, where it appears as signal burst 420. The signal burst 420 received by the implanted coil 42-1 may have a different intensity than does the signal burst 240 as a function of the coupling efficiency between the two coils 24-1 and 42-1, the number of turns in each coil, and the impedance matching that occurs between the circuits of the External Controller 20 and the combined load attached to the Output Circuit 40-1, which combined load includes the implanted coil 42-1, the electrode 32 and the body tissue in contact with the electrode 32. This different intensity may still be sufficiently controlled by the External Controller so that the energy contained within the signal burst 420, defined in large part by the envelope of the signal burst 240, is sufficient to stimulate the tissue at the desired electroacupuncture site, or acupoint, thereby producing, over time, the desired therapeutic effect.

In some embodiments, passive filtering circuitry 424 may also be used within the Output Stage 401 to reconfigure or reshape the energy of the signal burst 240 into a suitable stimulation pulse 422. This stimulation pulse 422 is then applied to the electrode 32 through a coupling capacitor C.

As mentioned previously, the Output Stage circuit 40-1 shown in FIG. 24 is ideally suited for diagnostic and data gathering purposes. Nonetheless, such embodiment can also be effectively used by a patient who does not object to wearing an External Controller 20 on his or her wrist or leg when the stimulation sessions associated with use of the EA System 10 are employed.

Figures 25A, 25B:
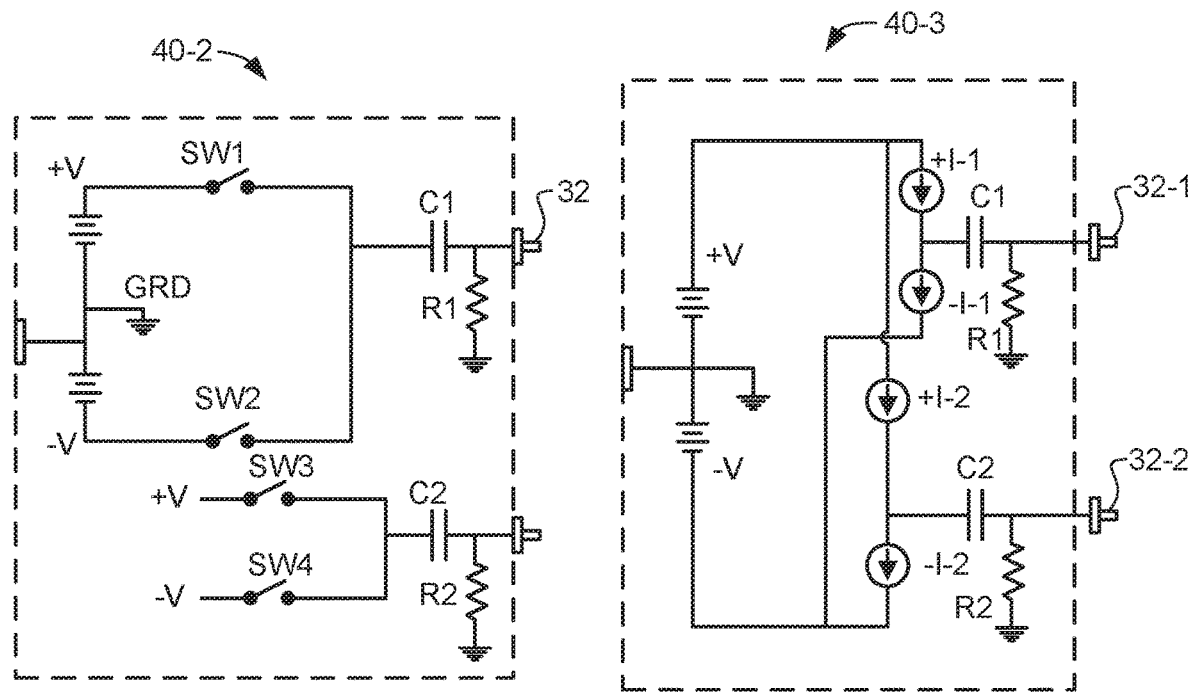
FIG. 25A is an electrical functional block diagram of a voltage stimulation output stage that may be used within the IEAD (right side of FIG. 23).
FIG. 25B is an electrical functional block diagram of a current stimulation output stage that may be used within the IEAD (right side of FIG. 23) instead of the voltage stimulation output state of FIG. 25A.

FIG. 25A functionally shows a representative Output Stage 40-2 that may be used when voltage stimulation is applied through the electrode(s) 32 to the desired acupoint. As seen in FIG. 25A, a positive voltage source, +V, and a negative voltage source, −V, are selectively and sequentially applied to an electrode 32, through switches SW1 and SW2. A coupling capacitor is preferably employed to prevent dc current from flowing through the electrode 32. If more than one electrode 32 is employed, a single pair of voltage sources may be selectively connected to each electrode using a suitable multiplexer circuit (not shown in FIG. 6A), as is known in the art.

FIG. 25B functionally shows a representative Output Stage circuit 40-3 that may be used when current stimulation is applied through the electrode(s) 32 to the desired acupoint. As seen in FIG. 6B, a positive current source, +I, and a negative current source, −I, are selectively applied to an electrode 32. In some embodiments, the current sources comprise independent programmable current sources that can readily be programmed to source, or sink, a precise current magnitude, as is known in the art. Advantageously, use of independent programmable current sources in this fashion allows, when multiple electrodes 32 are used, precise sharing of the currents in order to steer the electric fields emanating from the electrodes in a desired manner. For example, if three electrodes 32 were employed, a first of which sources 200 microamps (□a) of current, and thus functions as an anode, and a second and third of which each sink 100 □a, each thus functioning as cathodes, the resulting electric fields would make it appear that a virtual electrode existed at some point along a mid-point line between the second and third electrodes. Such steering of a virtual electrode would thus allow the effectiveness of the EA stimulation to be adjusted or tuned, which effectiveness is largely a function of the proximity between the acupoint site and the electrode. Advantageously, this adjustment, or tuning, can occur even after the IEAD 30 is implanted with a fixed physical location of the electrodes relative to the desired acupoint site.

Figure 26:
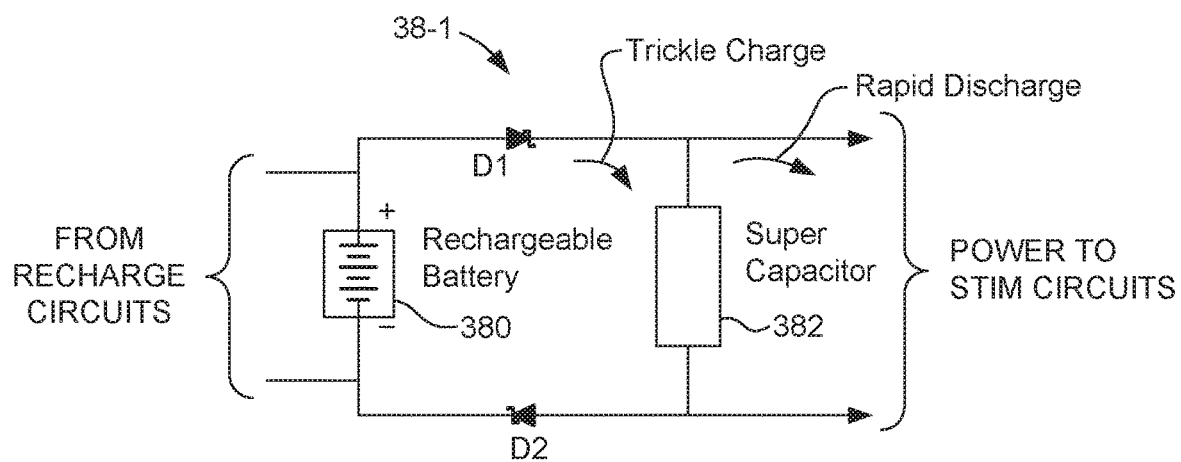

FIG. 26 illustrates a power source configuration 38-1 that may be used in some embodiments within the IEAD 30 for the implanted power source 38. The power source configuration 38-1 shown in FIG. 26 employs both a rechargeable battery 380 and a supercapacitor 382, connected in parallel. The rechargeable battery 380 is charged in conventional manner using power received from the recharge circuits. For most embodiments, this would be the power received through implanted coil 42 and the Receiver circuit 44 (see FIG. 23). The power stored in the battery 380 may thereafter be used to trickle charge the supercapacitor at times when the IEAD 30 is not stimulating body tissue. Then, when there is a demand for a pulse of stimulation current, the energy required for such pulse may be pulled from the super capacitor in a relatively rapid discharge mode of operation. Diodes D1 and D2 are used to isolate the supercapacitor 382 from the battery 380 when the supercapacitor is undergoing a rapid discharge.

Figure 27:
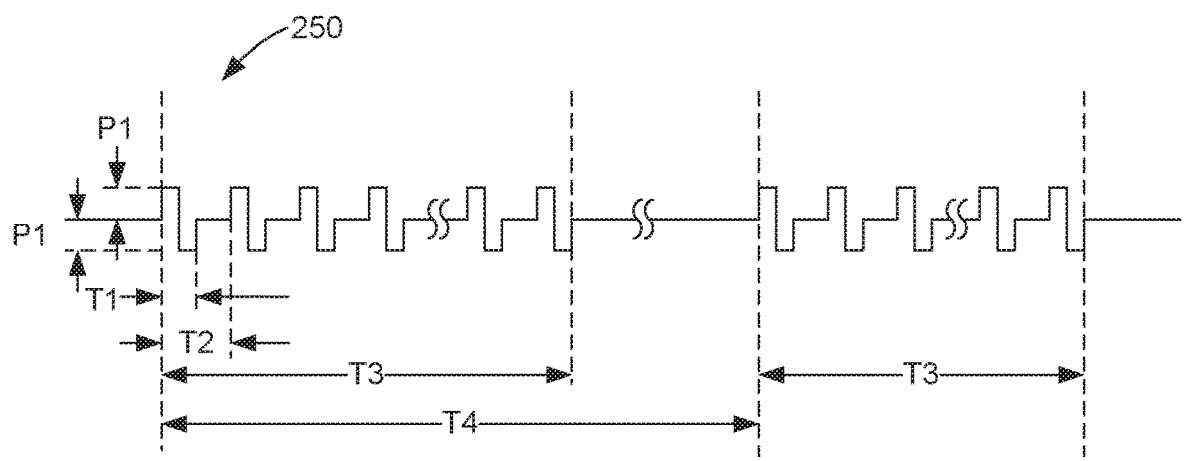
Figure 28:
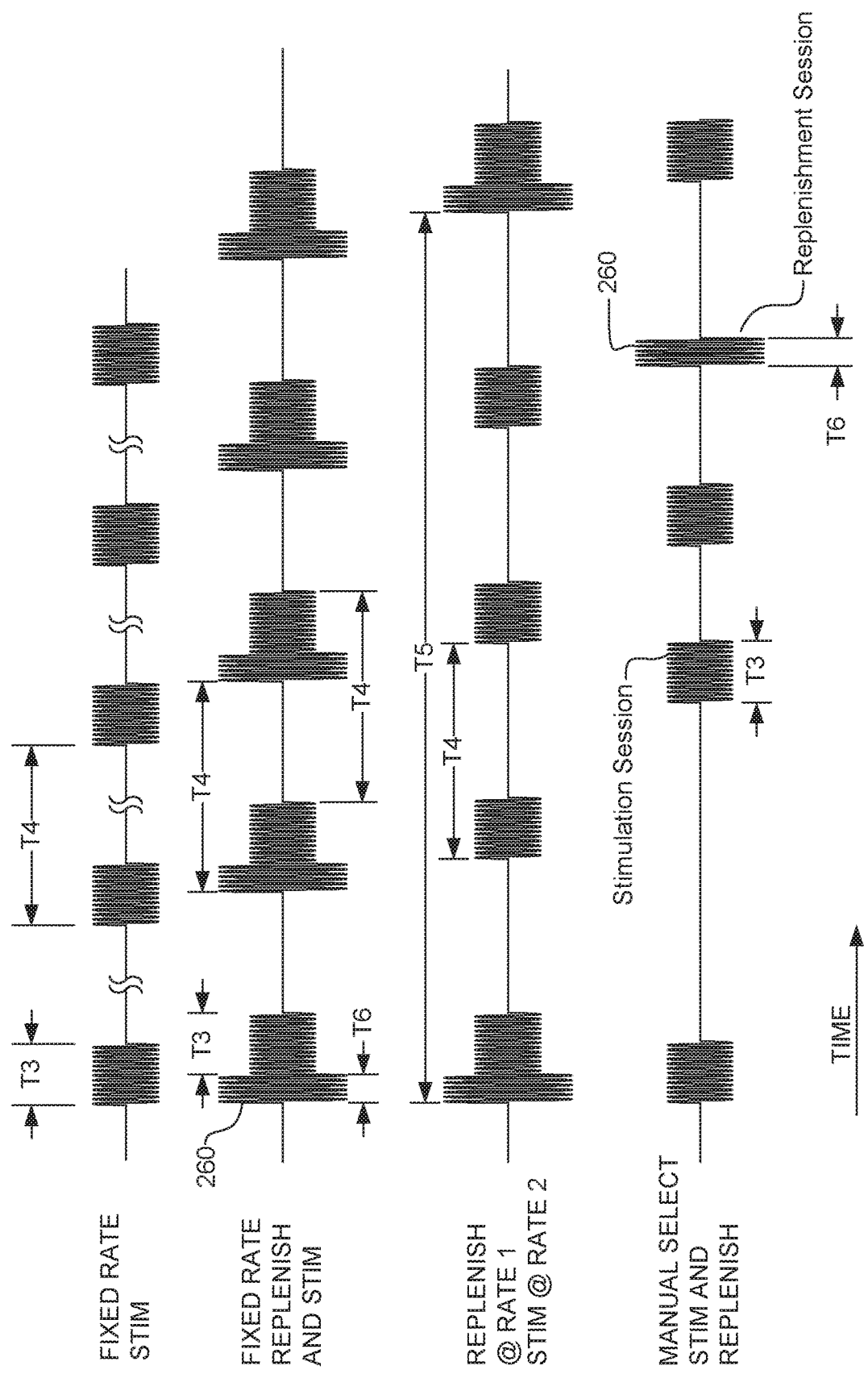

Next, with respect to FIGS. 27 and 28, timing diagrams are shown to illustrate a typical stimulation regime that may be employed by the EA System 10. First, as seen in FIG. 27, the electroacupuncture (EA) stimulation pulses preferably comprise a series of biphasic stimulation pulses of equal and opposite polarity for a defined time period T1 seconds. Thus, as seen at the left edge of FIG. 27, a biphasic stimulation pulse 250 comprises a pulse having a positive phase of amplitude +P1 followed by a negative phase having an amplitude of −P1. (Alternatively, the biphasic stimulation pulse could comprise a pulse having a negative phase of amplitude −P1 followed by a positive phase of amplitude +P1.) Each phase has a duration of T1/2 seconds, or the entire biphasic pulse has a total duration of T1/2+T1/2=T1 seconds. (This assumes the positive phase duration is equal to the negative phase duration, which is usually the case for a biphasic stimulation pulse.) The rate at which the biphasic pulses occur is defined by the time period T2 seconds. FIG. 27 makes it appear that T2 is approximately twice as long as T1. However, this is not necessarily the case. In many stimulation regimes, T2 may be many times longer than T1. For example, the time T1 may be only 20 milliseconds (ms), with each phase being 10 ms, but the time T2 may be one second, or 1000 ms, or two seconds (2000 ms). The time periods T1 (pulse width) and T2 (pulse rate) are thus important parameters that define a preferred stimulation regime. The ratio of T1/T2 defines the duty cycle of the stimulation pulses when the stimulation pulses are being applied.

Still referring to FIG. 27, the next parameter shown is the stimulation session period, or T3. This is the time over which stimulation pulses of width T1 are applied at a rate T2. The session length T3, for example, may be 15, 30, 45 or 60 minutes, or any other suitable value as selected by medical personnel for delivery to a specific patient.

The stimulation session, in turn, is also applied at a set rate, as determined by the time period T4. Typical times for T4 include 12, 24 or 48 hours, or longer, such as one week or two weeks. Thus, for example, if T4 is 24 hrs. T3 is 30 minutes, T2 is 1 second, and T1 is 20 ms, then biphasic stimulation pulses having a width of 20 ms are applied once each second for a session time of 30 minutes. The session, in turn, is applied once every 24 hours, or once each day.

Figure 15A:
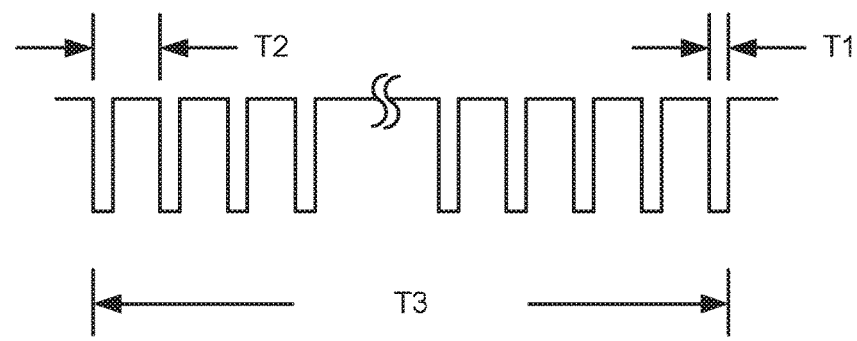
FIG. 15A shows a timing waveform diagram of representative EA stimulation pulses generated by the IEAD device during a stimulation session.

It should be noted that bi-phasic stimulation pulses as shown in FIG. 27 are not the only type of stimulation pulses that may be used. In Section II, below, another type of stimulation pulse (a negative-going pulse) is used with the specific example described there. A negative-going pulse is shown in FIG. 15A.

Next, as seen in FIG. 28, several variations of possible stimulation patterns are illustrated. In the top line of FIG. 28, a fixed rate stimulation sequence is illustrated where a stimulation session, having a duration of T3 seconds, is applied at a rate defined by time period T4. If T3 is 30 minutes, and T4 is 24 hours, then the fixed stimulation rate is one stimulation session lasting 30 minutes applied once each day.

The second line of FIG. 28 shows a stimulation pattern that uses a fixed stimulation rate and a fixed replenishing rate, which rates are the same, occurring every T4 seconds. A replenishing signal is a signal from which energy is extracted for charging or replenishing the implanted power source 38. Frequently, the replenishing signal may itself be modulated with data, so that whenever replenishing occurs, control data may also be transmitted. This control data can be new data, as when a stimulation regime is to be followed, or it can just be the same data as used previously, and it is used just to refresh or re-store the existing control data.

A replenishing signal is illustrated in FIG. 28 as pulses 260, which are drawn having a higher amplitude than the stimulation session pulses, and which have a duration of T6 seconds. It is noted that the time scale in FIG. 28 is not drawn to scale. Thus, whereas as illustrated in FIG. 28 the stimulation session time T3 appears to be twice as long as the replenishment time T6, such is not necessarily the case.

The third line in FIG. 28 shows an example of a replenishment signal being generated every T5 hrs, and a stimulation session occurring every T4 hours. As shown in FIG. 28, T4 is significantly less than T5. For example, T5 may be 168 hours (1 week), whereas T4 may be 24 hours, or once a day.

The last line in FIG. 28 illustrates a manual selection of the occurrence of a stimulation session and of a replenishment session. Hence, no rate is associated with either of these events. They simply occur whenever they are selected to occur. Selection can be made through use of the External Controller 20, or in the case of a stimulation session (where no external recharging power is needed), through use of the reed switch 48). One type of manually-triggered stimulation is illustrated below in the flow diagram of FIG. 30.

Figure 29:
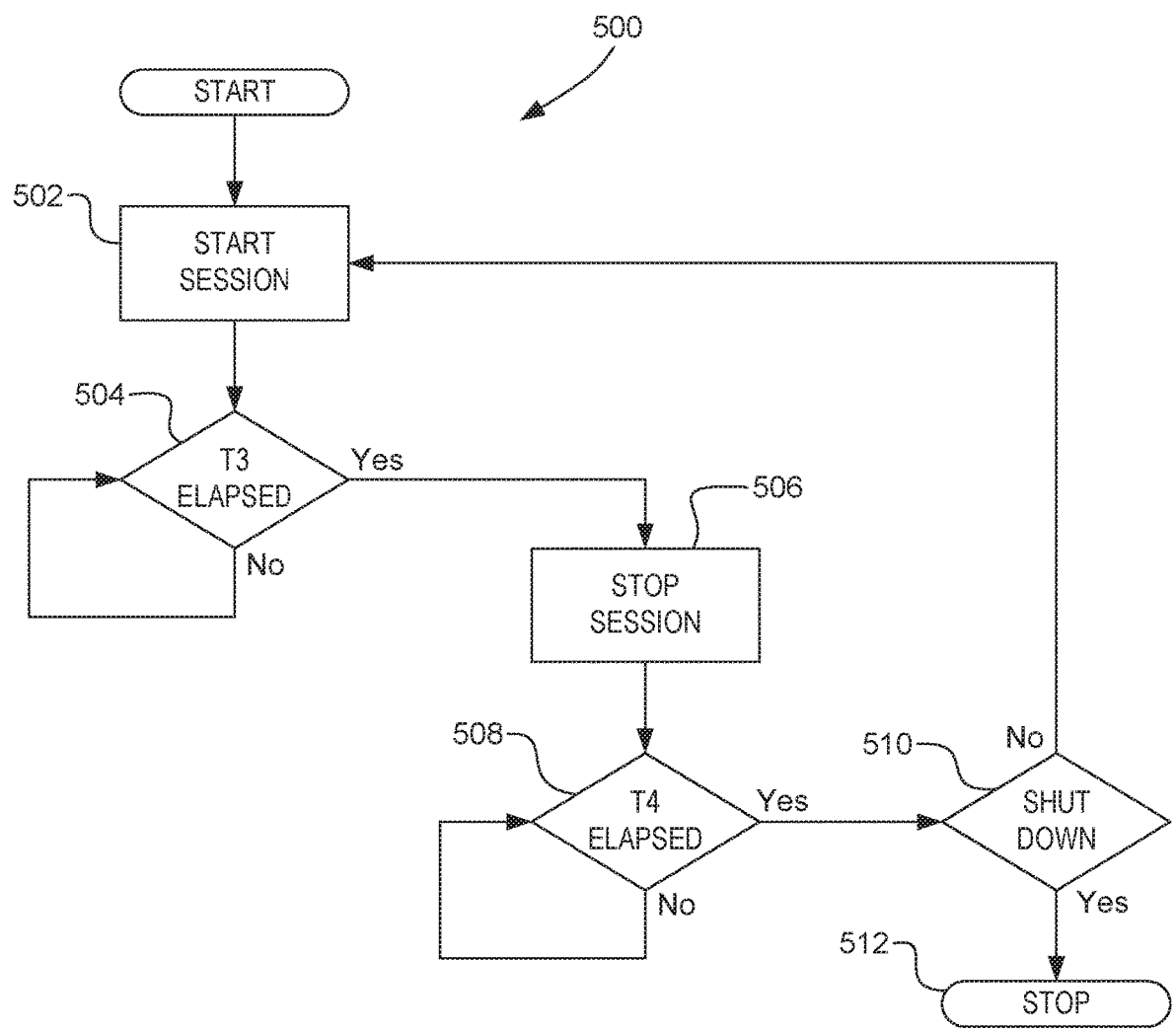

Turning next to FIG. 29, a flow chart is shown that illustrates a method 500 for automatically applying continuous stimulation sessions in accordance with a prescribed stimulation regimen. Such method 500 applies stimulation sessions having a fixed duration of T3 minutes every T4 minutes. As seen in FIG. 29, such method is carried out by starting a stimulation session (block 502). During the stimulation session, the elapsed time is monitored and a determination is made as to whether the time period T3 has elapsed (block 504). If not (NO branch of block 504), the time monitoring continues. Once the time period T3 has elapsed (YES branch of block 504), the stimulation session is stopped (block 506). However, even with the stimulation session stopped, time continues to be monitored (block 508). When the time T4 has elapsed (YES branch of block 508) then a determination is made as to whether a Shut Down mode should be entered (block 510). If so (YES branch of block 510), then the application of stimulation sessions is stopped (block 512). If not (NO branch of block 510), then a new stimulation session of T3 minutes begins (block 502), and the process continues. The timing waveform diagram corresponding to the flow diagram of FIG. 29 is the top waveform in FIG. 28.

A variation of the method 500 depicted in FIG. 29 is to alternate the time periods of the stimulation session duration, T3, between two different values. That is, T3 is set to toggle between a first value $T3_1$ for the stimulation session duration and a second value $T3_2$ for the stimulation session, with the value $T3_1$ being used every other stimulation session. Thus, a time line of the method of treating cardiovascular disease follows a sequence $T3_1$-T4-$T3_2$-T4-$T3_1$-T4-$T3_2$-T4- . . . and so on, where T4 is the time period between stimulation sessions.

If such a method is followed of toggling between two values of T3, representative values for $T3_1$ and $T3_2$ could be to set $T3_1$ to a value that ranges between 10 minutes and 40 minutes, and to set $T3_2$ to a value that ranges between 30 minutes and 60 minutes.

Similarly, a further variation of this method of treating cardiovascular disease would be to toggle the value of T4, the time between stimulation sessions, between two values. That is, in accordance with this method, the time T4 would be set to toggle between a first value $T4_1$ and a second value $T4_2$, with the value $T4_1$ being used after every other stimulation session. Thus, a time line of this method of treating cardiovascular disease would follow a sequence T3-$T4_1$-T3-$T4_2$-T3-$T4_1$-T3-$T4_2$-T3-$T4_1$ . . . and so on, where T3 is the duration of the stimulation sessions.

If such method is followed, representative values for $T4_1$ and $T4_2$ could be to set $T4_1$ to a value that ranges between 720 minutes [½ day] and 10,080 minutes [1 week], and to set $T4_2$ to a value that ranges between 1,440 minutes [1 day] and 20,160 minutes [2 weeks].

Additional variations of these methods of toggling between different values of T3 and T4 are also possible. For example, multiple values of T3-$T3_1$, $T3_2$, $T3_3$, $T3_4$, $T3_5$ . . . $T3_n$—could be set, and then the values could be used in sequence, or randomly during successive stimulation sequences. Multiple values of T4 could also be employed, and the various values of T3 and T4 could be combined together in the sequences followed.

If such methods are used to adjust the values of T3 and T4, care must be exercised to not exceed the maximum duty cycle associated with the preferred stimulation regimens. That is, the invention requires that the ratio of T3/T4 be no greater than 0.05. Thus, if either, or both, T3 and T4 are varied, limits should be placed on the ranges the parameters can assume in order to preserve the desired duty cycle. For example, the range of values within which T3 may be selected is typically between 10 minutes and 60 minutes. The ranges of values within which T4 may be selected is normally between about 12 hours and 2 weeks. However, as the value of T4 decreases, and the value of T3 increases, a point is reached where the maximum duty cycle could be exceeded. Thus, to prevent the maximum duty cycle from exceeding 0.05, the range of values for T3 and T4 may be specified by setting the time T3, the duration of the stimulation sessions, to be at least 10 minutes but no longer than a maximum value, T3(max). The value of T3(max) is adjusted, as needed, to maintain the duty cycle, the ratio of T3/T4, at a value no greater than 0.05. Thus, T3(max) is equal to 60 minutes if T4, the time period between stimulation sessions is between 1,200 minutes [20 hours] and 20,160 minutes [14 days]. However, T3(max) should be set to a value set by the equation T3(max)=0.05*T4 when T4 is between 720 minutes [½ day] and 1,200 minutes [20 hours].

Figure 30:
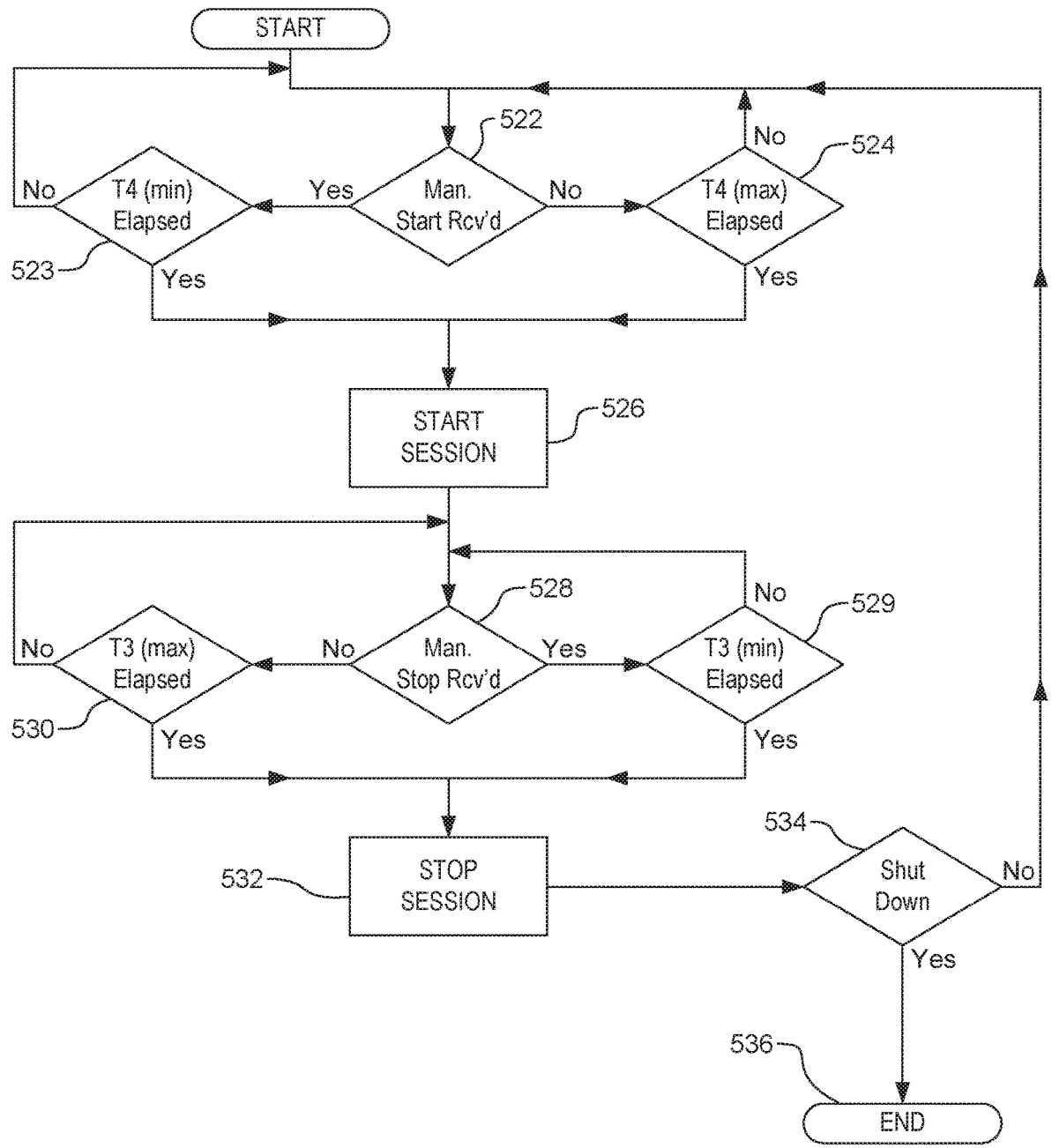

Next, with reference to FIG. 30, there is depicted a flow chart for a method 520 for manually triggering the application of stimulation sessions. When manual stimulation sessions are triggered, some basic parameters must still be observed. That is, there must be a minimum duration of a stimulation session T3(min), as well as a maximum duration of a stimulation session T3(max). Similarly, there needs to be a minimum time period T4(min) that separates one stimulation session from another, and a maximum time period T4(max) allowed between stimulation sessions before the next stimulation session is automatically started. Representative values for these parameters are, for example, T3(min)=10 minutes, T3(max)=60 minutes, T4(min)=12 hours, and T4(max)=2 weeks.

With the basic operating parameters described above defined, the method 520 shown in FIG. 29 proceeds by first determining whether a manual start command (or trigger signal) has been received (block 522). If not (NO branch of block 522), then a determination is made as to whether the time T4(max) has elapsed. If it has (YES branch of block 524), then a stimulation session is started (block 526). If T4(max) has not elapsed (NO branch of block 524), then the IEAD 30 just keeps waiting for a manual trigger signal to occur (block 522).

If a manual trigger signal is received (YES branch of block 22), then a determination is made as to whether T4(min) has elapsed (block 523). Only if T4(min) has elapsed (Yes branch of block 523) is a stimulation session started (block 526). Thus, two consecutive stimulation sessions cannot occur unless at least the time T4(min) has elapsed since the last stimulation session.

During a stimulation session, the circuitry carrying out method 520 also monitors whether a manual stop signal has been received (block 528). If so (YES branch of block 528), then a determination is made as to whether the time T3(min) has elapsed. If not (NO branch of block 529), then the session continues because the minimum session time has not elapsed. If T3(min) has elapsed (YES branch of block 529), then the session is stopped (block 532). If a manual stop signal is not received (NO branch of block 528), and if T3(max) has not yet elapsed (NO branch of block 530), then nothing happens (i.e., the session continues) until T3(max) has elapsed (YES branch of block 530), at which time the stimulation session is terminated (block 532).

Still with reference to FIG. 30, once the session is stopped (block 532), a determination is made whether the EA stimulation should shut down (block 534). If so (YES branch of block 534) the stimulation terminates (block 536). If not, then the circuitry goes into a waiting mode where it monitors whether a manual start command is received, or the time T4(max) elapses, whichever occurs first (blocks 522, 524), and the next stimulation session is started (block 526). And, the process continues.

Thus, it is seen that the method 520 shown in FIG. 30 allows a stimulation session to be manually started at any time a manual start command is received, providing that at least the time T4(min) has elapsed since the last session. Similarly, the method allows a stimulation session to be manually stopped at any time during the stimulation session, providing that at least the time T3(min) has elapsed since the session started. Absent the occurrence of receiving a manual start command, the next session starts automatically after T4(max) elapses. Similarly, during a stimulation session, absent a stop command, the session will stop automatically after the time T3(max) has elapsed.

Figure 31:
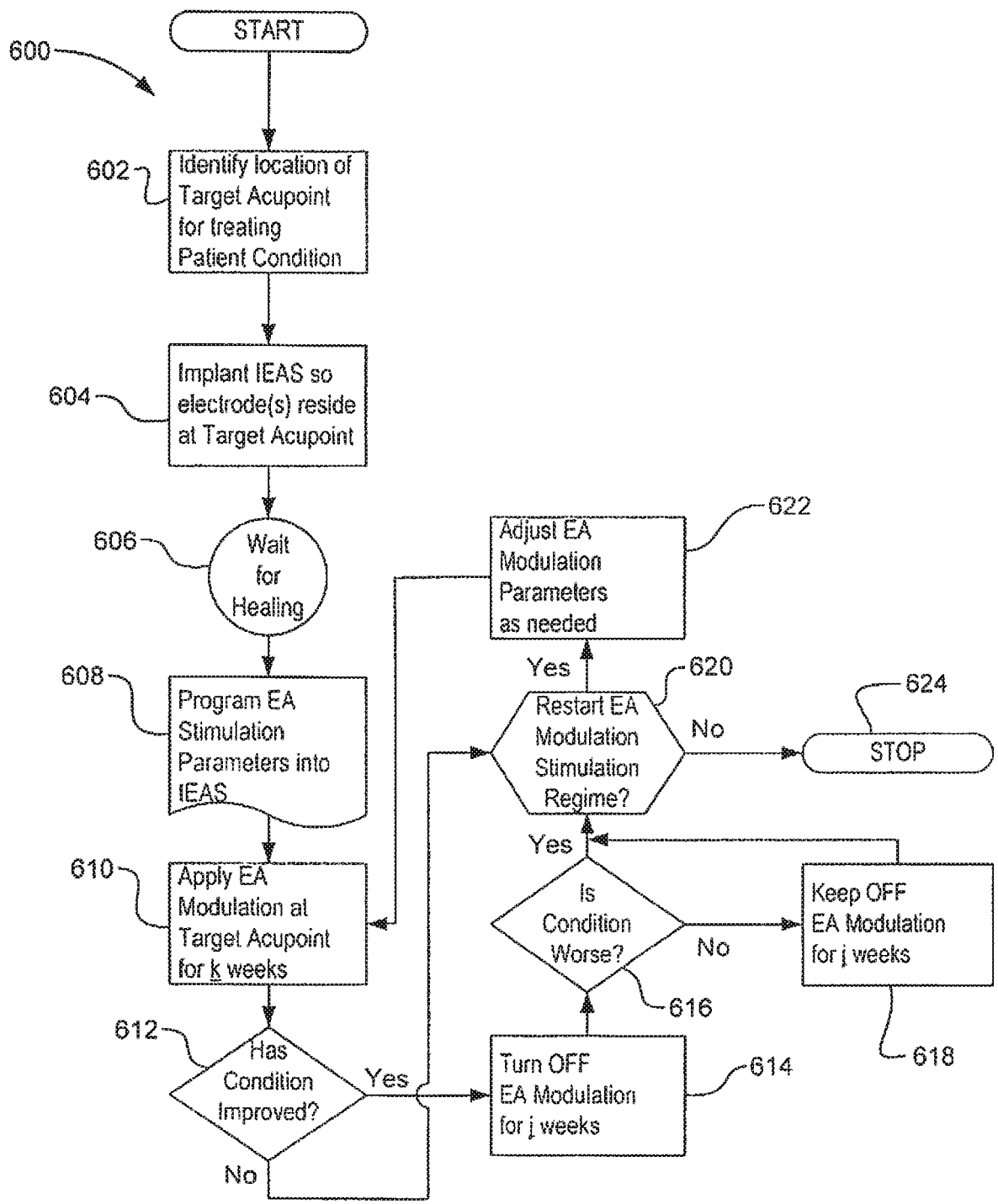

Next, with reference to FIG. 31, a flow chart is shown that depicts one method 600 of using an EA System 10 of the type described herein, or equivalents thereof, to treat cardiovascular disease. It is emphasized that the method shown in FIG. 31 is just one of many methods that may be used, and includes steps or actions taken that may not always be needed nor desired. (Note that each step in the flow chart shown in FIG. 31 is represented by a rectangular (or other shaped) block having a reference number assigned to it. Once the action or other activity indicated in a step, or block, of the method is completed, then the method flows to the next step, or block, in the flow chart. Decision steps are represented by a diamond (4-sided) or hexagonal (6-sided) shape, also having a reference number assigned to it.) For example, the method shown in FIG. 31 includes three decision steps or blocks, 612, 616 and 620, where, depending on the question being asked, one of two paths or branches must be followed. In a simplified version or embodiment of the method, however, these three decision blocks may be eliminated. In such simplified method, the method reduces to following the steps shown in blocks 602, 604, 606, 608, 610, 614, 620 and 622, which blocks are described below.

For the method that uses the three decision blocks, as seen in FIG. 31, the method outlined in the flow diagram of FIG. 31 assumes that the condition, illness or other physiological deficiency (hereafter "Condition") being treated by the EA system 10 has been identified. Then, the method begins at block 602, which requires identifying the location of the appropriate acupoint(s) for treating the Condition through the application of appropriate EA Modulation. Recall that, as used herein, "EA modulation" is the application of electrical stimulation pulses, at low intensities, frequencies and duty cycles, to at least one of the acupuncture sites that has been identified as affecting a particular illness, deficiency or condition. For treating cardiovascular disease, the acupoints include PC6, ST36, BL14 (also referred to as UB14), EX-HN1 (located approximately one centimeter from GV20), HT7, HT5, LI11, LU2 and LU7. Other possible acupoints also exist, as described previously. So, for purposes of completing the step described at block 602, one of the possible acupoints that could be used is selected as the target acupoint.

Once the location of the target acupoint to be modulated has been identified, the next step (block 604) is to implant the IEAS 30 so that its electrodes are firmly anchored and located so as to be near or on the target acupoint. Then, after waiting a sufficient time for healing to occur associated with the implant surgery (block 606), which is usually just a week or two, the next step is to program the IEAD 30 with the parameters of the selected stimulation regime that is to be followed by the IEAD 30 as it applies EA modulation to the target acupoint (block 608). The parameters that define the selected stimulation regime include the time periods T1, T2, T3, T4, T5 and T6 (described in connection with the description of FIGS. 27 and 28), the intensity P1 of the stimulation pulses (also described previously in connection with FIG. 27), and the number of weeks, k, that EA modulation is to be applied before monitoring the Condition to see if improvement has occurred, as well as the number of weeks, j, that EA modulation should be turned off before restarting the same or a new EA Modulation regime.

Once implanted and programmed, EA Modulation begins and continues for a period of k weeks (block 610). After k weeks, the patient's Condition, in this case cardiovascular disease, is checked to see if it has improved (decision block 612). If YES, the EA Modulation is turned OFF for a waiting period of j weeks (block 614). After waiting j weeks, while keeping the EA Modulation deactivated, the Condition is again checked (decision block 616) to see if the condition has returned to its previous high blood pressure state, or to see if the improvement made has lessened or deteriorated (decision block 616). If NOT, that is, if the Condition still remains at acceptable levels, then a decision may be made by medical personnel in consultation with the patient as to whether the EA Modulation regime should be repeated in order to further help the patient's body maintain the Condition at desired levels (decision block 620).

If a decision is made to repeat the EA Modulation (YES branch of decision block 620), then the EA Modulation parameters are adjusted as needed (block 622) and the EA Modulation begins again at the target acupoint, following the programmed stimulation regime (block 610).

If a decision is made NOT to repeat the EA Modulation (NO branch of decision block 620), then that means the treatment for the Condition is over and the process stops (block 624). In such instance, the patient may elect to have the IEAD 30 removed surgically, which is a very simple procedure.

Backtracking for a moment to decision block 612, where a decision was made as to whether the Condition had improved after the EA Modulation had been applied for a period of k weeks, if the determination made is that the Condition had not improved (NO branch of decision block 612), then again, medical personnel in consultation with the patient may make a decision as to whether the EA Modulation regime should be repeated again (block 620).

Further backtracking to decision block 616, where a decision was made as to whether, after the j weeks of applying no additional EA Modulation, the Condition had returned to its previous high blood pressure state, or the improvement had lessened (YES branch of decision block 616), then again medical personnel in consultation with the patient may make a decision as to whether the EA Modulation regime should be repeated again (block 620).

In a simplified version of the method depicted in FIG. 31, only the steps identified at blocks 602, 604, 606, 608, 610, 614, 620 and 622 are followed. This method thus reduces to identifying the target acupoint (block 602), implanting the IEAS at the target acupoint (block 604), waiting for the surgery to heal (block 606), programming EA simulation parameters into the IEAS (block 608) (which programming could actually be done before implanting the IEAS, if desired), applying EA modulation to the target acupoint for k weeks (block 610), turning off the EA modulation for j weeks (block 614), adjusting or tweaking the EA stimulation parameters, if needed (block 622), and repeating the cycle over again starting with block 610.

II. Specific Example

With the foregoing as a foundation for the general principles and concepts of the present invention, a specific example of the invention will next be described in connection with a description of FIGS. 1-16. Such specific example teaches one manner in which the general principles and concepts described above may be applied to one specific electroacupuncture (EA) device, or IEAD. Although one specific example is being described, there are many variations of it that are generally referred to in the description of the specific example as "embodiments". Also, it should be noted that because the description of the specific example is presented in conjunction with a different set of drawings, FIGS. 1-16, than were used to describe the general principles and concepts of the invention, FIGS. 17-31, there will be some differences in the reference numerals used in connection with one set of drawings relative to the reference numerals used in connection with the other set of drawings to describe the same or similar elements. However, such different reference numerals should not be a source of confusion because the context of how and where the references numerals are presented will clearly identify what part or element is being referenced.

The EA device of this specific example is an implantable, coin-shaped, self-contained, symmetrical, leadless electroacupuncture (EA) device having at least two electrode contacts mounted on the surface of its housing. In one preferred embodiment, the electrodes include a central cathode electrode on a bottom side of the housing, and an annular anode electrode that surrounds the cathode. In another preferred embodiment, the anode annular electrode is a ring electrode placed around the perimeter edge of the coin-shaped housing.

The EA device is leadless. This means there are no leads or electrodes at the distal end of leads (common with most implantable electrical stimulators) that have to be positioned and anchored at a desired stimulation site. Also, because there are no leads, no tunneling through body tissue is required in order to provide a path for the leads to return and be connected to a tissue stimulator (also common with most electrical stimulators).

The EA device is adapted to be implanted through a very small incision, e.g., less than 2-3 cm in length, directly adjacent to a selected acupuncture site ("acupoint") known to moderate or effect a cardiovascular condition of a patient.

The EA device is easy to implant. Also, it is symmetrical. This means that there is no way that it can be implanted incorrectly (unless the physician puts it in up-side-down, which would be difficult to do given the markings on its case). All that need be done is to cut the incision, and slide the device in place through the incision. Once the implant pocket has been prepared, it is as easy as sliding a coin into a slot. Such implantation can usually be completed in less than 10 minutes in an outpatient setting, or in a doctor's office. Only minor, local anesthesia need be used. No major or significant complications are envisioned for the implant procedure. The EA device can also be easily and quickly explanted, if needed.

The EA device is self-contained. It includes a primary battery to provide its operating power. It includes all of the circuitry it needs, in addition to the battery, to allow it to perform its intended function for several years. Once implanted, the patient will not even know it is there, except for a slight tingling that may be felt when the device is delivering stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can easily do so using, e.g., an external magnet.

The EA device can operate for several years because it is designed to be very efficient. Stimulation pulses applied by the EA device at a selected acupoint through its electrodes formed on its case are applied at a very low duty cycle in accordance with a specified stimulation regimen. The stimulation regimen applies EA stimulation during a stimulation session that lasts at least 10 minutes, typically 30 minutes, and rarely longer than 60 minutes. These stimulation sessions, however, occur at a very low duty cycle. In one preferred treatment regimen, for example, a stimulation session having a duration of 30 minutes is applied to the patient just once a week. The stimulation regimen, and the selected acupoint at which the stimulation is applied, are designed and selected to provide efficient and effective EA stimulation for the treatment of the patient's cardiovascular disease.

The EA device is, compared to most implantable medical devices, relatively easy to manufacture and uses few components. This not only enhances the reliability of the device, but helps keep the manufacturing costs low, which in turn allows the device to be more affordable to the patient. One key feature included in the mechanical design of the EA device is the use of a radial feed-through assembly to connect the electrical circuitry inside of its housing to one of the electrodes on the outside of the housing. The design of this radial feed-through pin assembly greatly simplifies the manufacturing process. The process places the temperature sensitive hermetic bonds used in the assembly—the bond between a pin and an insulator and the bond between the insulator and the case wall—away from the perimeter of the housing as the housing is hermetically sealed at the perimeter with a high temperature laser welding process, thus preserving the integrity of the hermetic bonds that are part of the feed-through assembly.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

Another key feature included in the design of the EA device is the use of a commercially-available battery as its primary power source. Small, thin, disc-shaped batteries, also known as "coin cells," are quite common and readily available for use with most modern electronic devices. Such batteries come in many sizes, and use various configurations and materials. However, insofar as applicants are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible, and so that dips in the battery output voltage (caused by any sudden surge in instantaneous battery current) do not occur that could compromise the performance of the device. Furthermore, the energy requirements of other active implantable therapies are far greater than can be provided by such coin cells without frequent replacement.

The EA device of this specific example advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Moreover, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture the EA device and to provide it to patients at an affordable cost.

II. A. Definitions

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−(0.05× 23 mm=1.15 mm).

"Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

II. B. Mechanical Design

Turing first to FIG. 1, there is shown a perspective view of one preferred embodiment of an implantable electroacupuncture device (IEAD) 100 made in accordance with the teachings disclosed herein. The IEAD 100 may also sometimes be referred to as an implantable electroacupuncture stimulator (IEAS). As seen in FIG. 1, the IEAD 100 has the appearance of a disc or coin, having a top side 102, a bottom side 106 and an edge side 104.

As used herein, the "top" side of the IEAD 100 is the side that is positioned closest to the skin of the patient when the IEAD is implanted. The "bottom" side is the side of the IEAD that is farthest away from the skin when the IEAD is implanted. The "edge" of the IEAD is the side that connects or joins the top side to the bottom side. In FIG. 1, the IEAD 100 is oriented to show the bottom side 106 and a portion of the edge side 104.

Many of the features associated with the mechanical design of the IEAD 100 shown in FIG. 1 are the subject of a prior U.S. Provisional Patent Application, entitled "Radial Feed-Through Packaging for An Implantable Electroacupuncture Device", Application No. 61/676,275, filed 26 Jul. 2012, which application is incorporated here by reference.

It should be noted here that throughout this application, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a top plate 122 is welded to the bottom case 124 to form the hermetically-sealed housing of the IEAD. The cathode electrode 110 is attached to the outside of the bottom case 124, and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
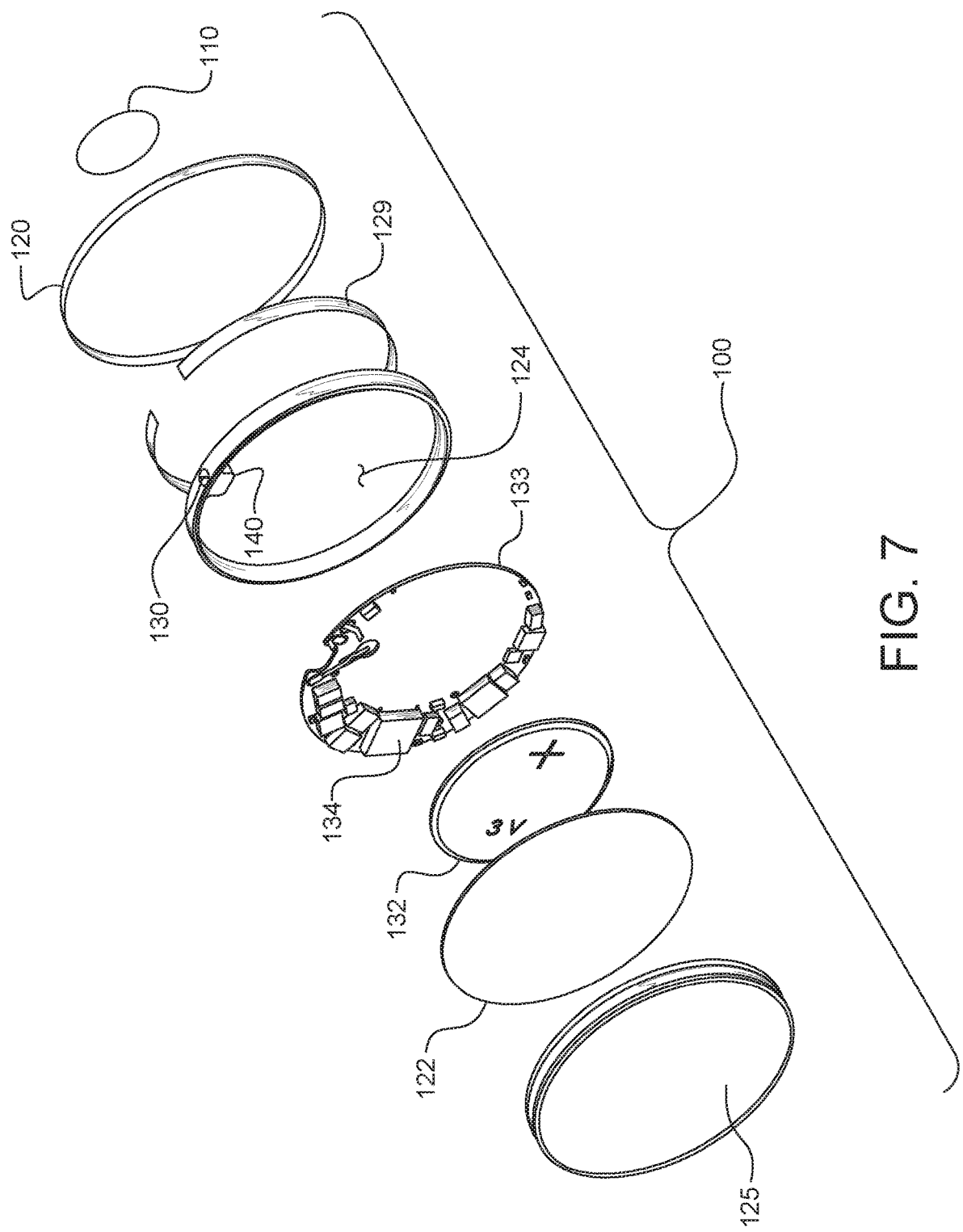

The embodiment of the IEAD 100 shown in FIG. 1 utilizes two electrodes, a cathode electrode 110 that is centrally positioned on the bottom side 106 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the bottom 106 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100 is facing down, i.e., facing deeper into the tissue, and that the IEAD is over the desired acupoint, or other tissue location, that is intended to receive the electroacupuncture (EA) stimulation. The orientation of the IEAD 100 is otherwise not important.

Figure 1A:
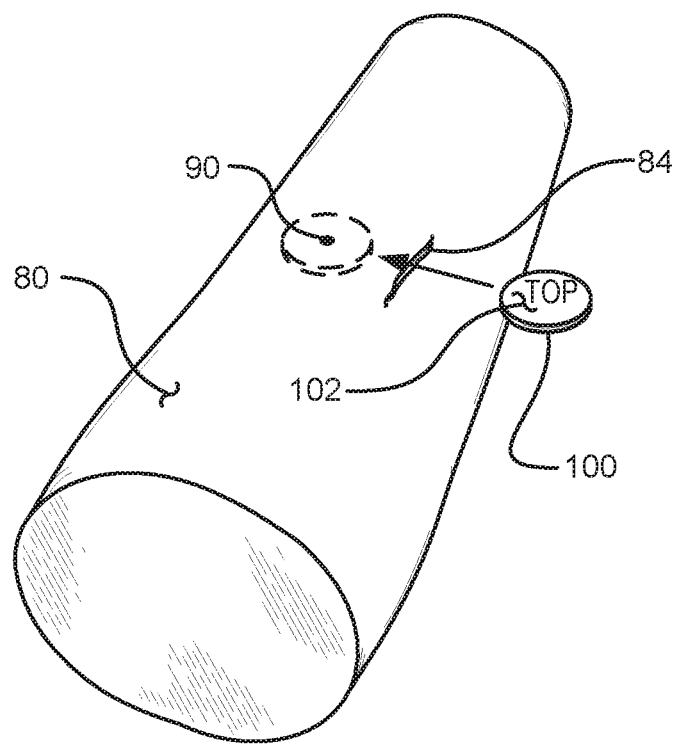
FIG. 1A shows a view of a patient's limb (arm or leg) where an acupoint has been identified, and illustrates the manner used to implant an IEAD at the selected acupoint.

Implantation of the IEAD is illustrated in FIG. 1A. Shown in FIG. 1A is a limb 80 of the patient wherein an acupoint 90 has been identified that is to receive acupuncture treatment (in this case electroacupuncture treatment). An incision 82 is made into the limb 80 a short distance, e.g., 10-15 mm, away from the acupoint 90. A slot 84 (parallel to the arm) is formed at the incision by lifting the skin closest to the acupoint up at the incision. As necessary, the surgeon may form a pocket under the skin at the acupoint location. The IEAD 100, with its top side 102 being closest to the skin, is then slid through the slot 84 into the pocket so that the center of the IEAD is located under the acupoint 90. This implantation process is as easy as inserting a coin into a slot. With the IEAD 100 in place, the incision is sewn or otherwise closed, leaving the IEAD 100 under the skin 80 at the location of the acupoint 90 where electroacupuncture (EA) stimulation is desired.

Figure 1B:
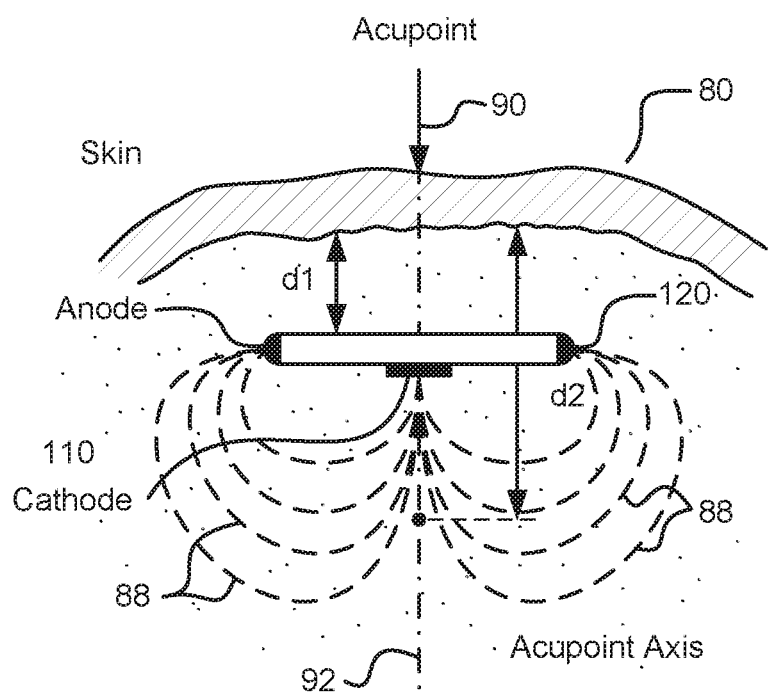
FIG. 1B shows a sectional view of an IEAD implanted at a selected acupoint, and illustrates the electric field gradient lines created when an electroacupuncture (EA) pulse is applied to the tissue through the central electrode and ring electrode attached to the bottom surface and perimeter edge, respectively, of the IEAD housing.

It should be noted that while FIG. 1B illustrates the acupoint 90 as being on the surface of the skin, the actual location where acupuncture treatment (whether it be administered through a needle, or through electroacupuncture (EA) stimulation) is most effective for purposes of the present invention is at a distance d2 below the skin surface along an axis line 92 extending orthogonally into the skin from the location on the skin where the acupoint 90 is indicated as being positioned. The distance d2 varies depending upon where the acupoint is located on the body. The depth d2 where EA stimulation is most effective for purposes of the particular acupoint chosen (to treat a cardiovascular disease) appears to be between about 6 to 10 mm below the acupoint 90 on the skin surface when the acupoint 90 is located in the forearm (e.g., acupoints PC6, HT5, LI11); and may be much deeper, e.g., 1 to 2 cm, if the location of an acupoint 90 is located in the leg (e.g., acupoint ST36).

FIG. 1B shows a sectional view of the IEAD 100 implanted so as to be centrally located under the skin at the selected acupoint 90, and over the acupoint axis line 92. Although the depth of implantation will vary depending upon the acupoint chosen and the condition to be tested, here the IEAD 100 is implanted at a depth d1 of approximately 2-4 mm under the skin. The top side 102 of the IEAD is nearest to the skin 80 of the patient. The bottom side 106 of the IEAD, which is the side on which the central cathode electrode 110 resides, is farthest from the skin. Because the cathode electrode 110 is centered on the bottom of the IEAD, and because the IEAD 100 is implanted so as to be centered under the location on the skin where the acupoint 90 is located, the cathode 110 is also centered over the acupoint axis line 92.

FIG. 1B further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1B, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the acupoint location indicated on the skin.

FIG. 2 shows a plan view of the "cathode" side (or bottom side) of the IEAD 100. As seen in FIG. 2, the cathode electrode 110 appears as a circular electrode, centered on the cathode side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "skin" side (the top side) of the IEAD 100. As will be evident from subsequent figure descriptions, e.g., FIGS. 5A and 5B, the skin side of the IEAD 100 comprises a top plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the top plate 122 is welded, or otherwise bonded, to the bottom case 124 in order to form the hermetically-sealed IEAD housing 100. (Note, in FIG. 3A, the "top" plate 122 is actually shown on the left side of the "bottom" case 124, which is shown on the right side. This is because the orientation of the drawing in FIG. 3A shows the IEAD 100 standing on its edge.)

FIG. 4 shows a perspective view of the IEAD case 124, including the feed-through pin 130, before the electronic components are placed therein, and before being sealed with the "skin side" cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
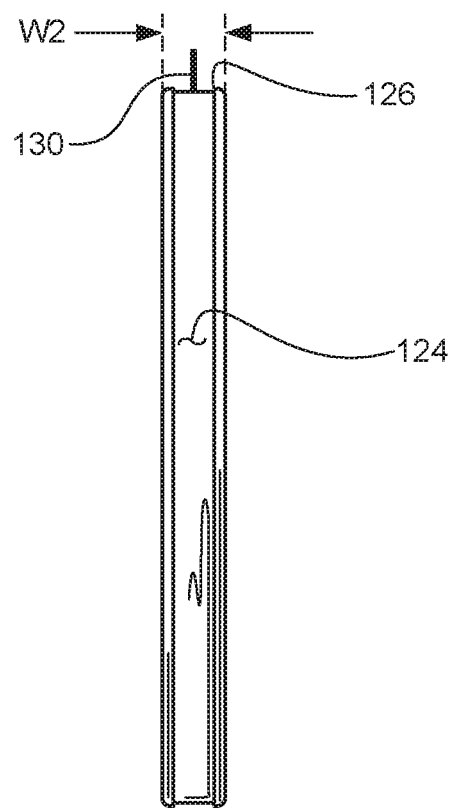
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. A silicone insulator layer 129 (see FIG. 7) is placed between the backside of the ring anode electrode 120 and the perimeter edge of the case 124 where the ring anode electrode 120 is placed around the edge of the case 124.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95%. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1 \times 10^{-9}$ STD cc/sec at 1 atm pressure. Other tests are performed to verify the case-to-pin resistance (which should be at least $15 \times 10^6$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in many of the provisional patent applications referenced above.

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a pc board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An overmolding process is used to accomplish this, although overmolding using silicone LSR 70 (curing temperature of 120° C.) with an injection molding process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well-known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the bottom or on the top surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Some particularly attractive alternate case shapes, and electrode placement on the surfaces of those case shapes, are illustrated in Appendix E. Any of these alternate shapes, or others, would still permit the basic principles of the invention to be used to provide a robust, compact, thin, case to house the electronic circuitry and power source used by the invention; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be easily implanted in a pocket over the tissue area where the selected acupoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Figure 7A:
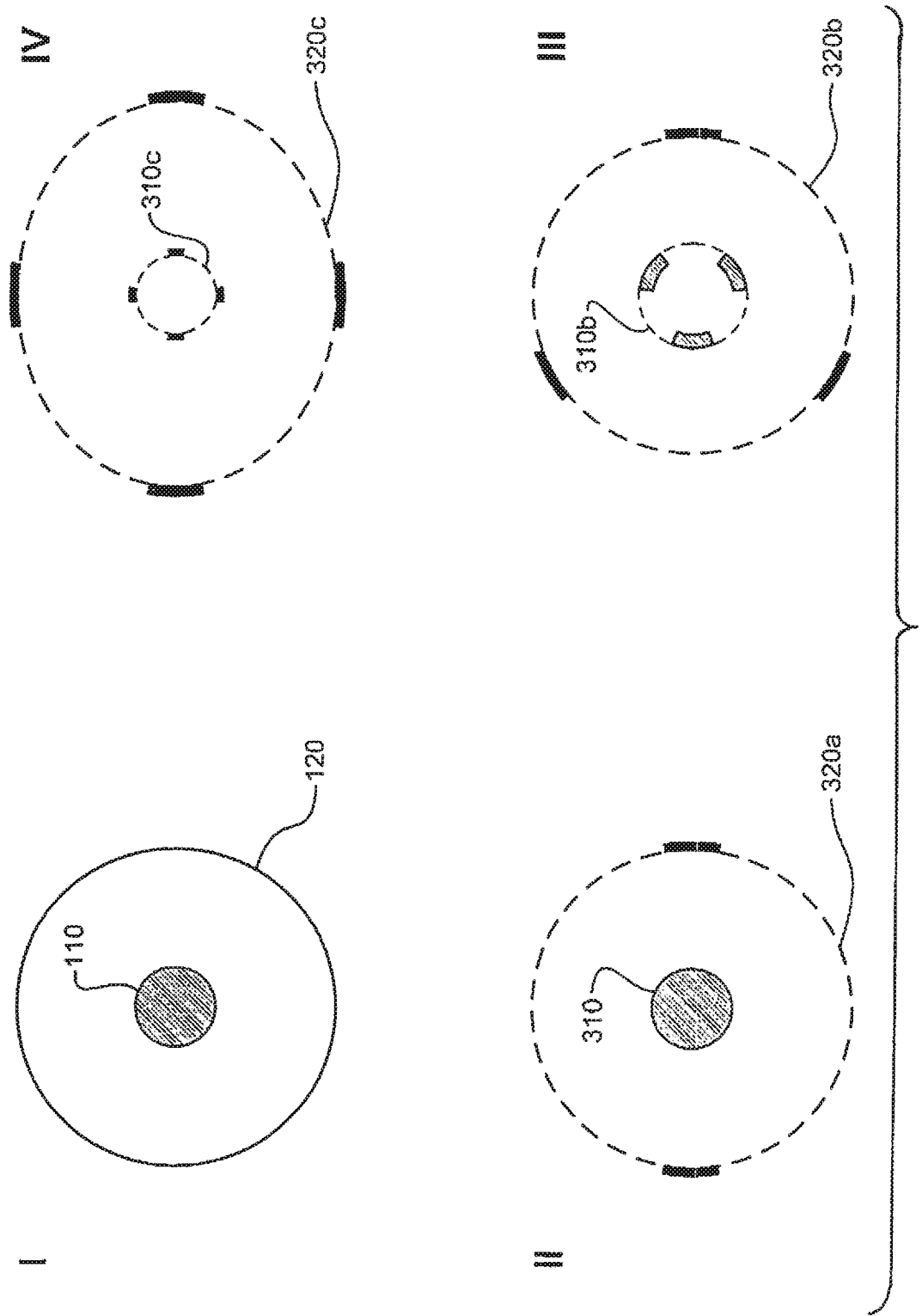
FIG. 7A schematically illustrates a few alternative electrode configurations that may be used with the invention.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a bottom surface of the housing, one of a first polarity, and a second of a second polarity, could still, when oriented properly with respect to a selected acupoint tissue location, provide some desired therapeutic results FIG. 7A schematically illustrates a few alternative electrode configurations that may be used with the invention. The electrode configuration schematically shown in the upper left corner of FIG. 7A, identified as "I", schematically illustrates one central electrode 110 surrounded by a single ring electrode 120. This is one of the preferred electrode configurations that has been described previously in connection, e.g., with the description of FIGS. 1, 1A, 1B and 7, and is presented in FIG. 7A for reference and comparative purposes.

In the lower left corner of FIG. 7A, identified as "II", an electrode/array configuration is schematically illustrated that has a central electrode 310 of a first polarity surrounded by an electrode array 320a of two electrodes of a second polarity. When the two electrodes (of the same polarity) in the electrode array 320a are properly aligned with the body tissue being stimulated, e.g., aligned with the longitudinal axis of the limb 80 (see FIG. 1A) wherein the IEAD is implanted, then such electrode configuration can stimulate the body tissue at or near the desired acupoint(s) with the same, or almost the same, efficacy as can the electrode configuration I (upper right corner of FIG. 7A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 7A, identified as "III", en electrode configuration is schematically illustrated that has a central electrode/array 310b of three electrode segments of a first polarity surrounded by an electrode array 320b of three electrode segments of a second polarity. As shown in FIG. 7A-III, the three electrode segments of the electrode array 320b are symmetrically positioned within the array 320b, meaning that they are positioned more or less equidistant from each other. However, a symmetrical positioning of the electrode segments within the array is not necessary to stimulate the body tissue at the desired acupoint(s) with some efficacy.

In the upper right corner of FIG. 7A, identified as "IV", an electrode/array configuration is schematically illustrated that has a central electrode array 310c of a first polarity surrounded by an electrode array 320c of four electrode segments of a second polarity. The four electrode segments of the electrode array 320c are arranged symmetrically in a round or oval-shaped array. The four electrode segments of the electrode array 310b are likewise arranged symmetrically in a round or oval-shaped array. Again, however, while preferred for many configurations, the use of a symmetrical electrode/array, whether as a central electrode array 310 or as a surrounding electrode/array 320, is not required in all configurations.

The electrode configurations I, II, III and IV shown schematically in FIG. 7A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, . . . n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

It should be noted that the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are described in Appendix A and Appendix B.

II. C. Electrical Design

Next, with reference to FIGS. 8A-14, the electrical design and operation of the circuits employed within the IEAD 100 will be described. More details associated with the design of the electrical circuits described herein may be found in the following previously-filed U.S. Provisional Patent Applications, which applications are incorporated herein by reference: (1) Appl. No. 61/626,339, filed Sep. 23, 2011, entitled Implantable Electroacupuncture Device and Method for Treating Cardiovascular Disease; (2) Appl. No. 61/609,875, filed Mar. 12, 2012, entitled Boost Converter Output Control For Implantable Electroacupuncture Device; (3) Appl. No. 61/672,257, filed Jul. 16, 2012, entitled Boost Converter Circuit Surge Control For Implantable Electroacupuncture Device Using Digital Pulsed Shutdown; (4) Appl. No. 61/672,661, filed Jul. 17, 2012, entitled Smooth Ramp-Up Stimulus Amplitude Control For Implantable Electroacupuncture Device; and (5) Appl. No. 61/674,691, filed Jul. 23, 2012, entitled Pulse Charge Delivery Control In An Implantable Electroacupuncture Device.

Figure 8A:
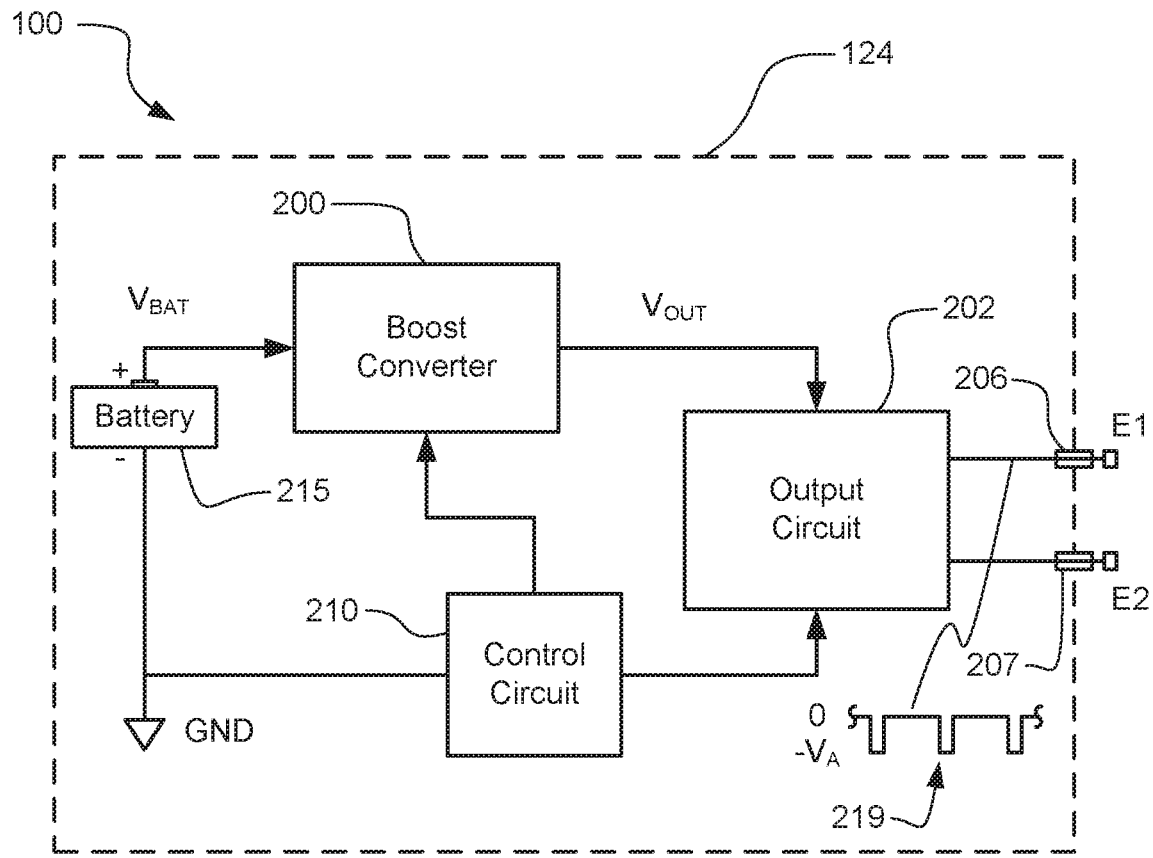
FIG. 8A illustrates a functional block diagram of the electronic circuits used within an IEAD of the type described herein.

FIG. 8A shows a functional block diagram of an implantable electroacupuncture device (IEAD) 100 made in accordance with the teachings disclosed herein. As seen in FIG. 8A, the IEAD 100 uses an implantable battery 215 having a battery voltage $V_{BAT}$. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

As explained more fully below in connection with the description of FIGS. 15A and 15B, the prescribed stimulation regimen comprises a continuous stream of stimulation pulses having a fixed amplitude, e.g., $V_A$ volts, a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week.

In one preferred embodiment, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and low duty cycles in accordance with specified stimulation regimens through electrodes that form an integral part of the housing of the stimulator. A tiny battery inside of the coin-sized stimulator provides enough energy for the stimulator to carry out its specified stimulation regimen over a period of several years. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
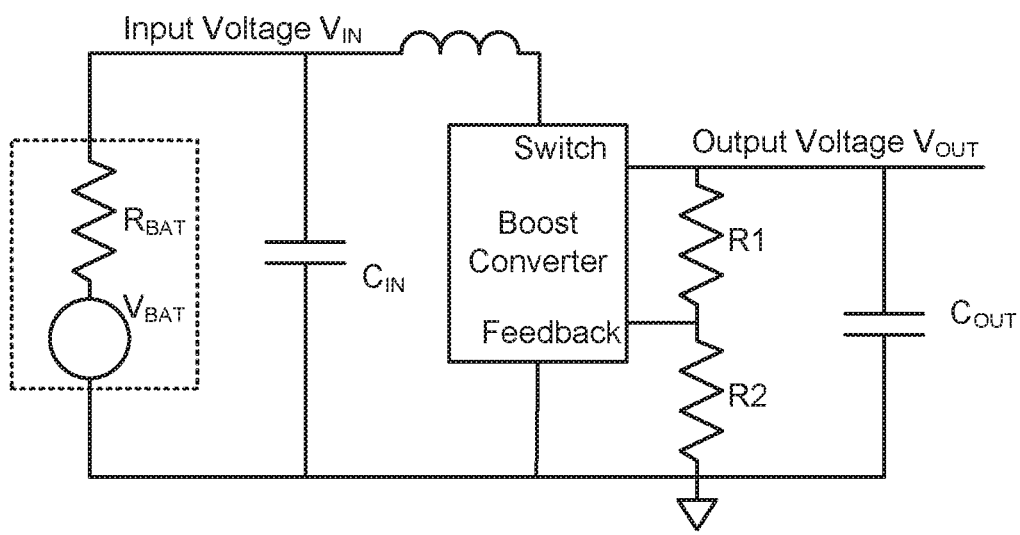
FIG. 8B shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 8A, the battery is modeled as a voltage source with a simple series resistance. With reference to the circuit shown in FIG. 8A, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
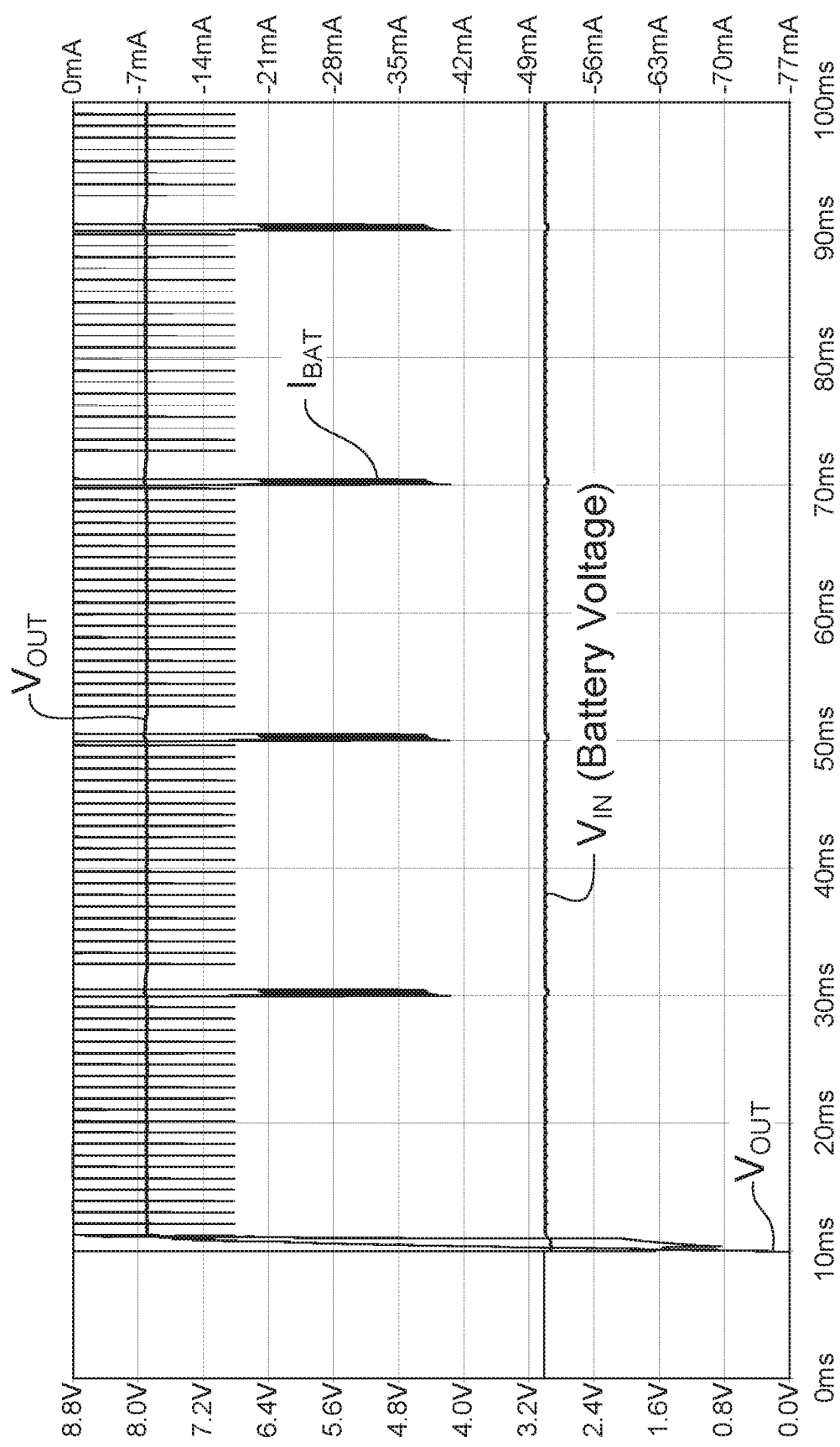
FIG. 9A illustrates a typical voltage and current waveform for the circuit of FIG. 8 when the battery impedance $R_{BAT}$ is small.

Referring to the waveform in FIG. 9A, at boost converter startup (10 ms), there is 70 mA of current drawn from the battery with only −70 mV of drop in the input voltage $V_{IN}$. Similarly, the instantaneous output current demand for electro-acupuncture pulses draws up to 40 mA from the battery with an input voltage drop of −40 mV.

Figure 9B:
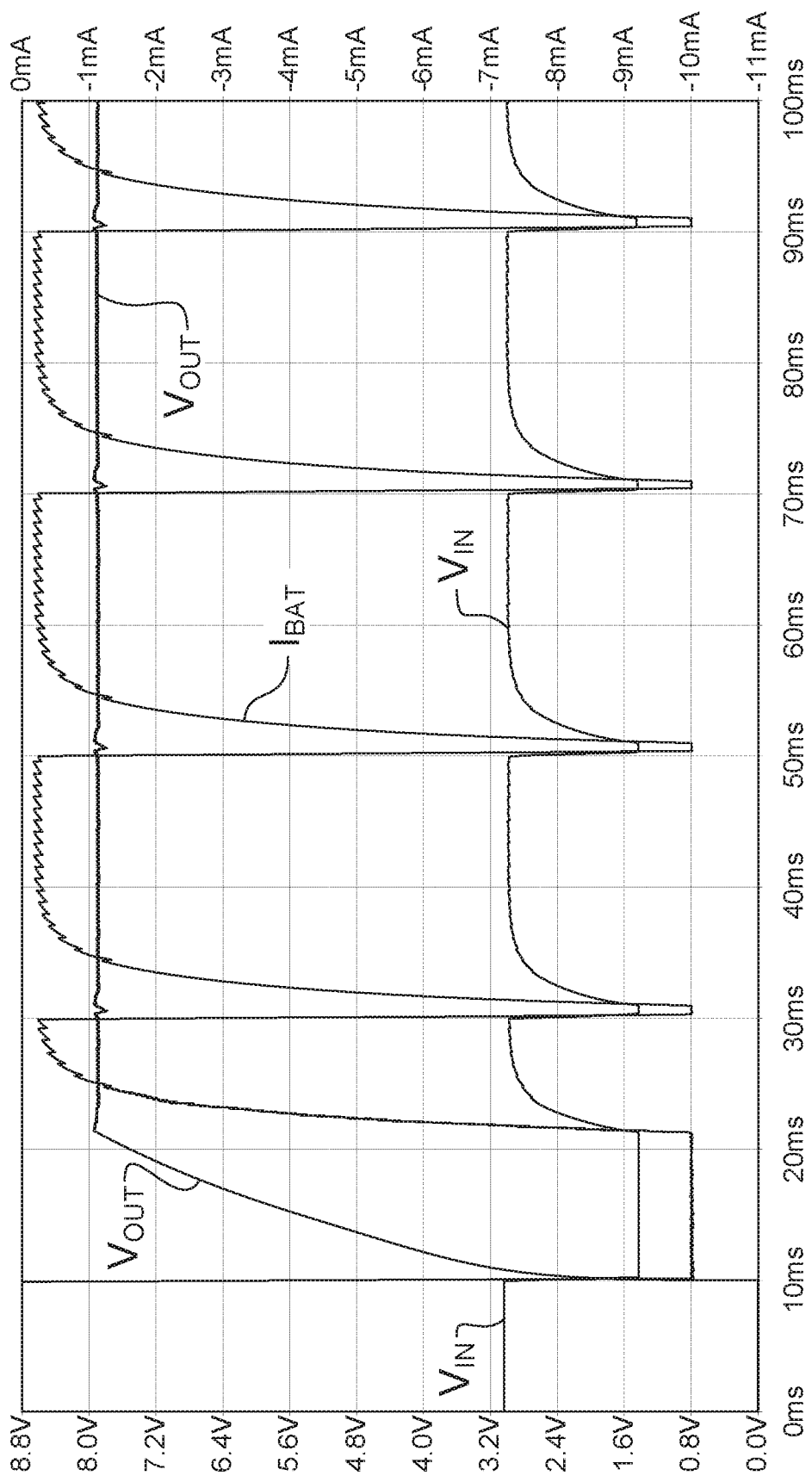
FIG. 9B shows the voltage and current waveform for the circuit of FIG. 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electroacupuncture stimulus pulses. The resulting drops in output voltage $V_{OUT}$ are just not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when EA stimulation pulses are generated.

Figure 10:
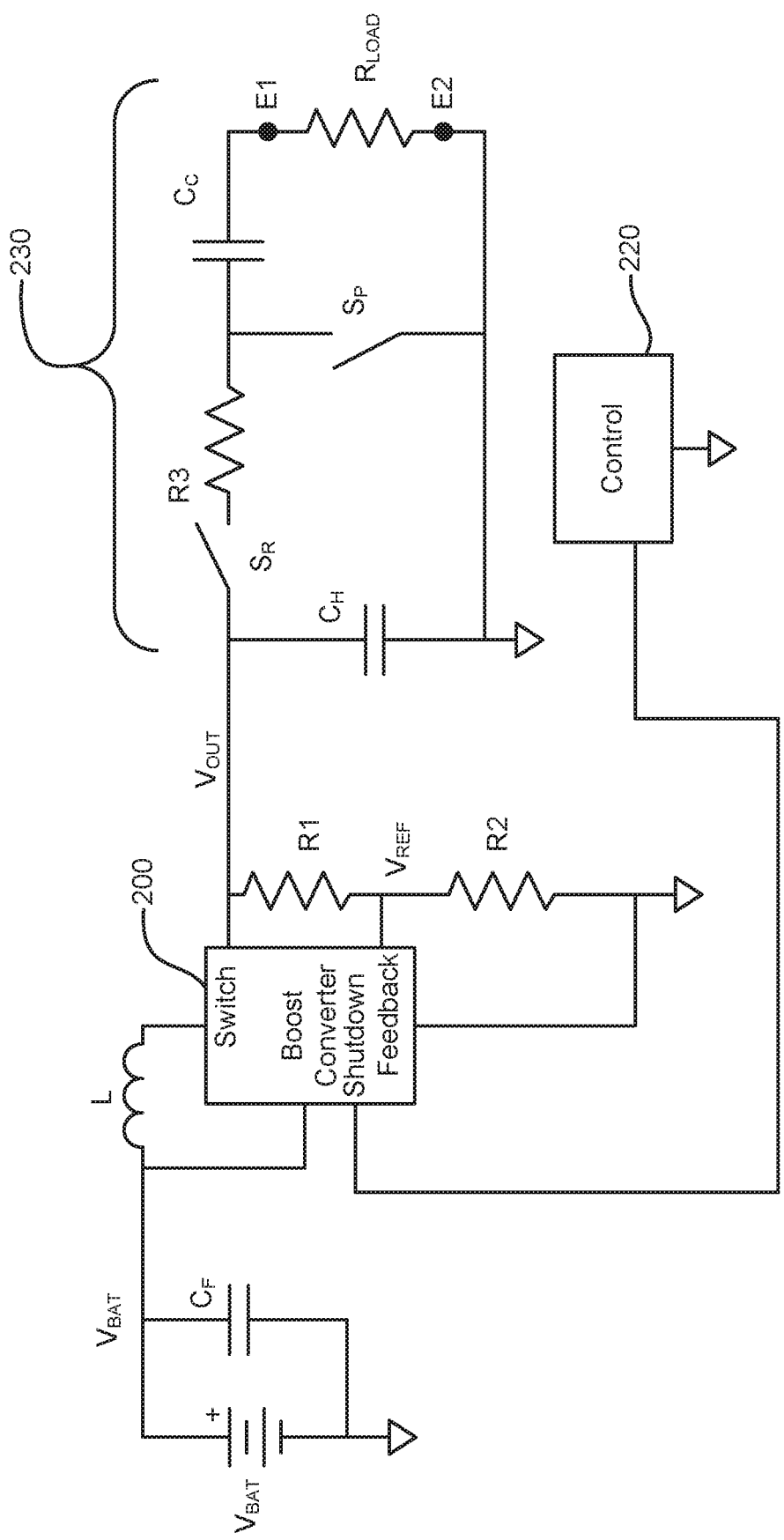

To provide this needed current management, the IEAD 100 disclosed herein employs electronic circuitry as shown in FIG. 10, or equivalents thereof. Similar to what is shown in FIG. 8B, the circuitry of FIG. 10 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220

(which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

Figure 11:
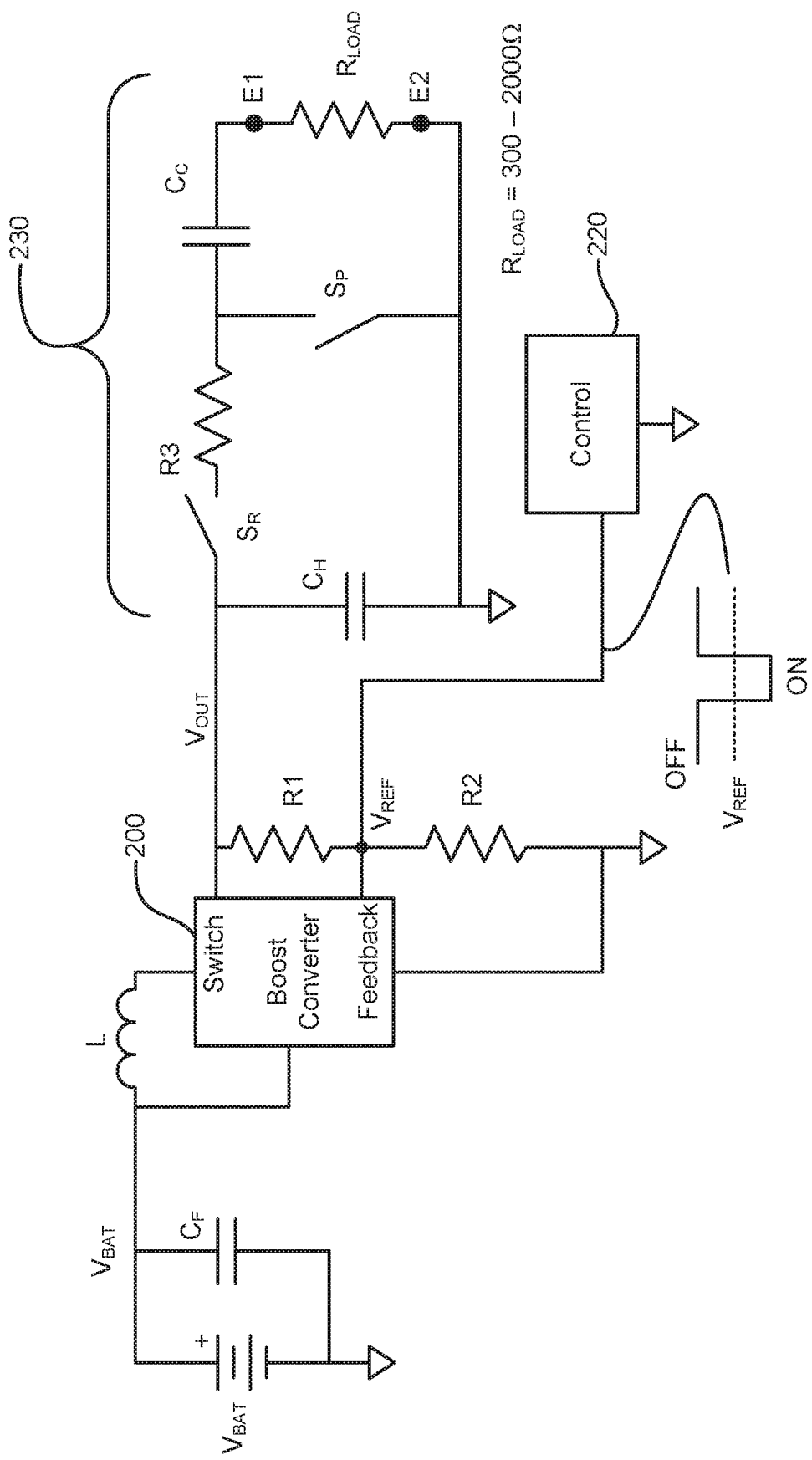

An alternate embodiment of the electronic circuitry that may be used within the IDEA 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning the boost converter circuit ON.

Figure 12:
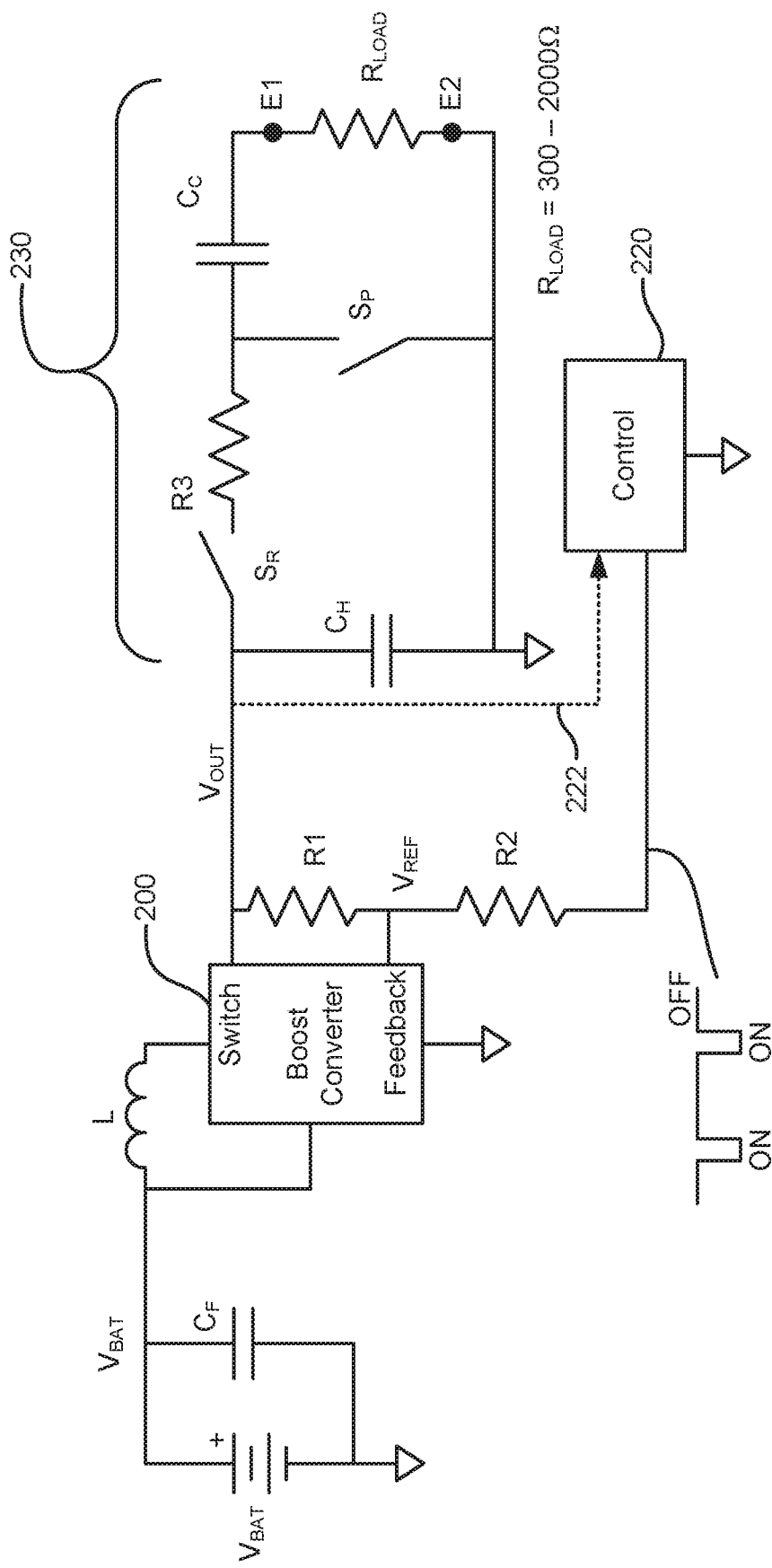

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
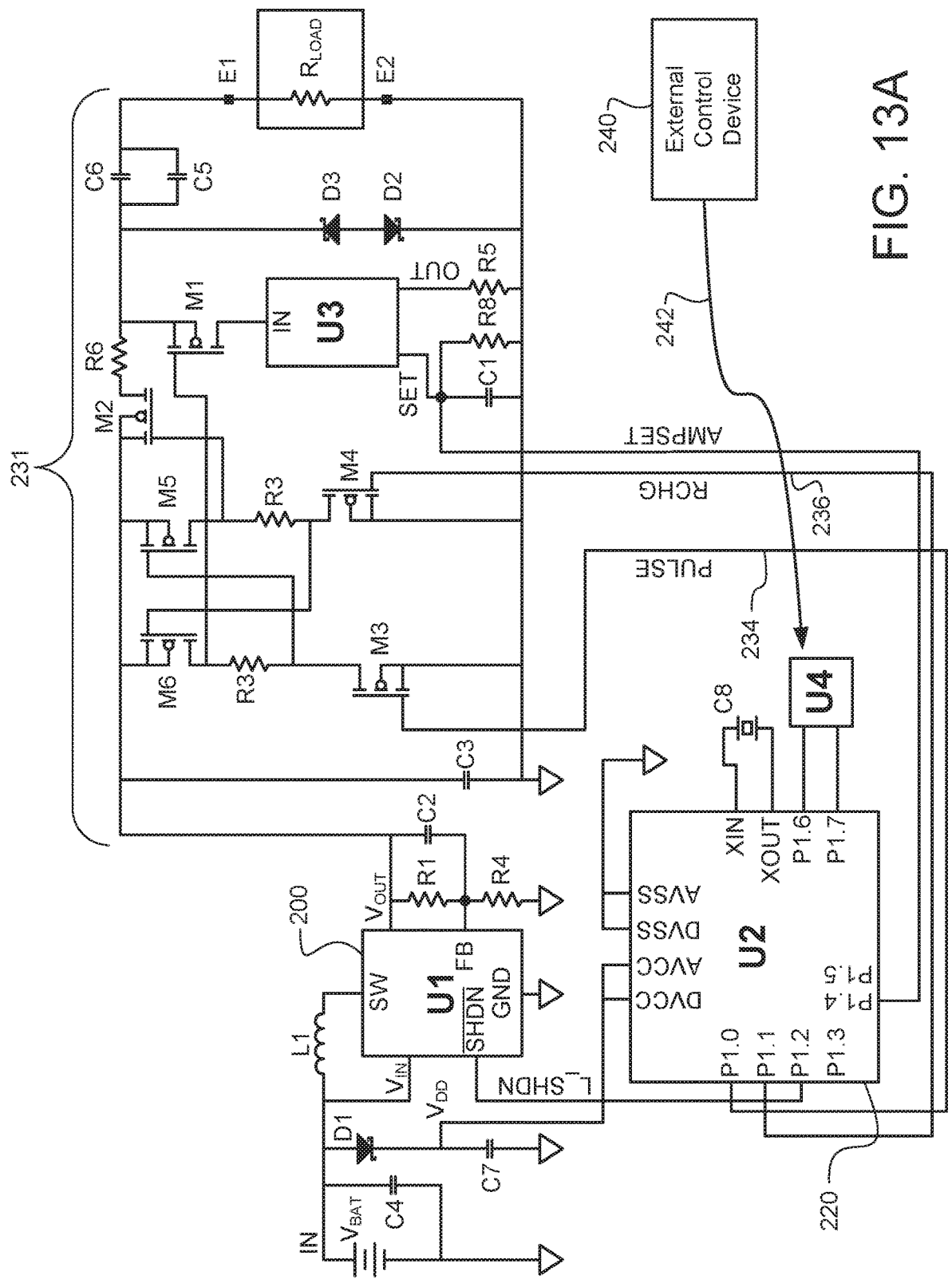
FIG. 13A shows one preferred schematic configuration for an implantable electroacupuncture device (IEAD) that utilizes the boost converter configuration shown in FIG. 10.

One preferred embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. A preferred IC for this purpose is a MSP430G24521 micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straightforward manner.

The micro-controller U2 primarily performs the function of generating the digital signal that shuts down the boost converter to prevent too much instantaneous current from being drawn from the battery $V_{BAT}$. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

It is also important that the circuitry used in the IEAD 100, e.g., the circuitry shown in FIGS. 10, 11, 12, 13A, or equivalents thereof, have some means for controlling the stimulation current that flows through the load, $R_{LOAD}$, which load may be characterized as the patient's tissue impedance at and around the acupoint being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 13A by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
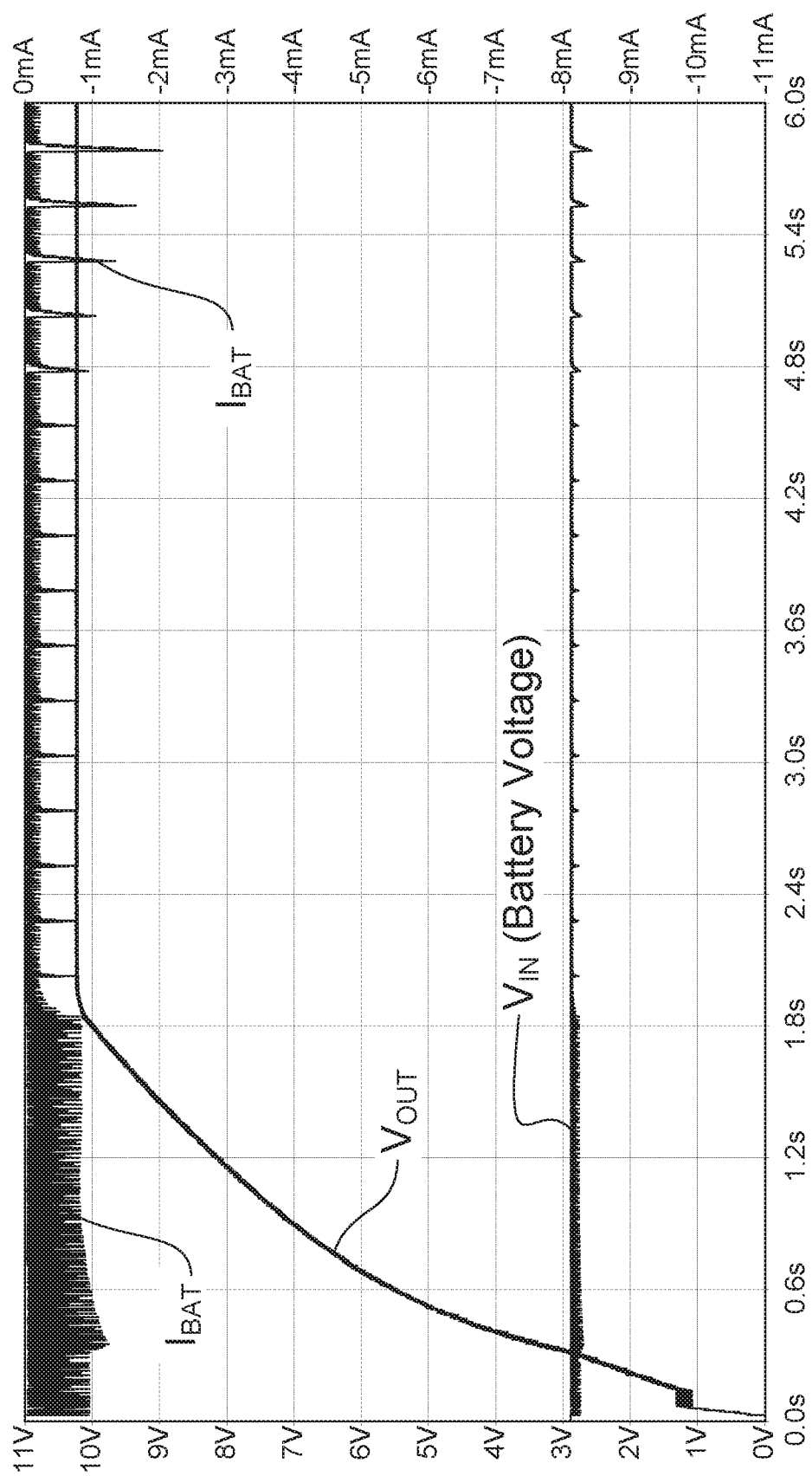
FIG. 13B shows current and voltage waveforms associated with the operation of the circuit shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13A have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
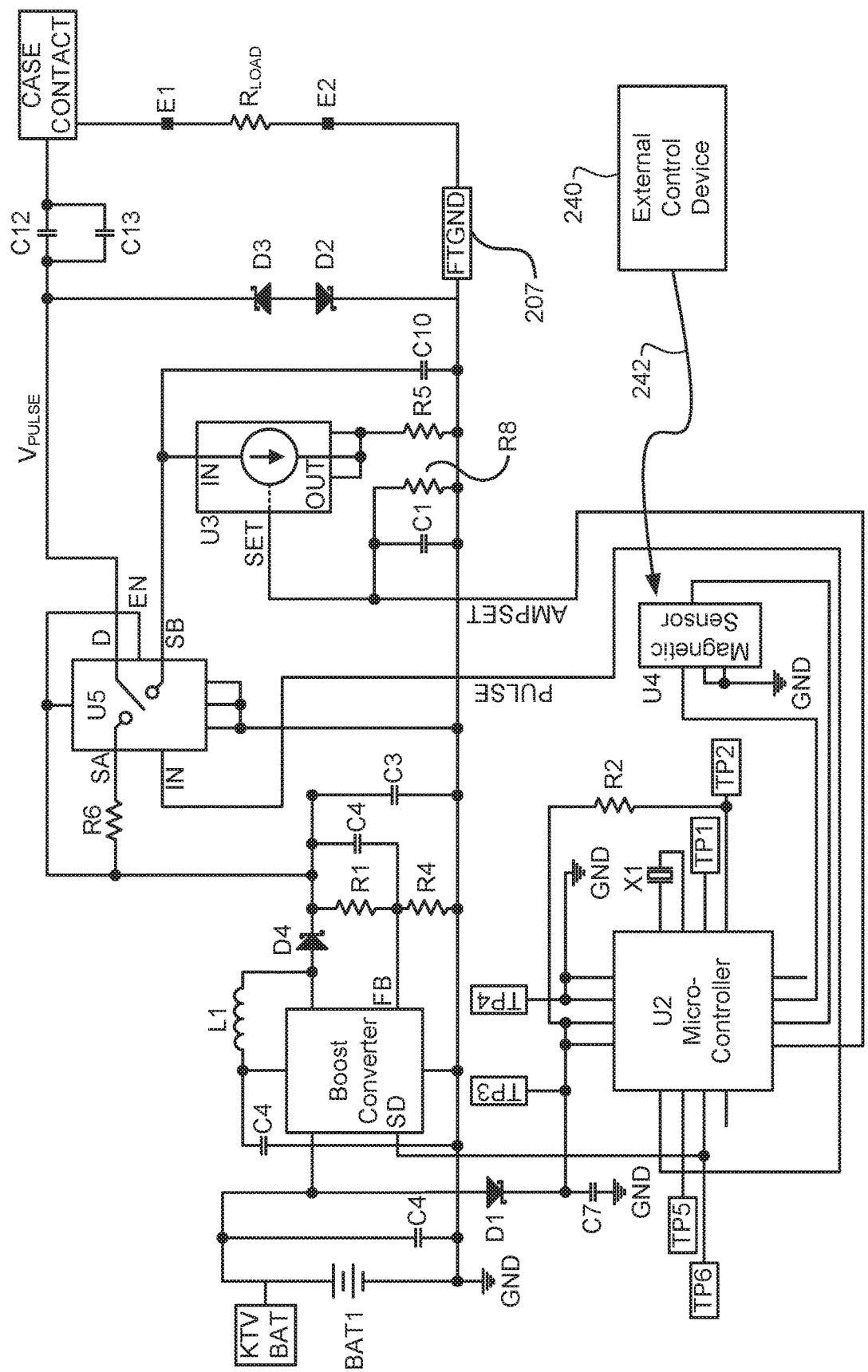

Another preferred embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of an external Schottky diode D4 at the output terminal LX of the boost convertor U1 and the inclusion of a fifth integrated circuit (IC) U5 that essentially performs the same function as the switches M1-M6 shown in FIG. 13A.

The Schottky diode D5 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (electromagnetic sensor) are basically the same as the IC's U1, U2, U3 and U4 described previously in connection with FIG. 13A.

The IC U5 shown in FIG. 14 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

From the above description, it is seen that an implantable IEAD 100 is provided that uses a digital control signal to duty-cycle limit the instantaneous current drawn from the battery by a boost converter. Three different exemplary configurations (FIGS. 10, 11 and 12) are taught for achieving this desired result, and two exemplary circuit designs that may be used to realize this result have been disclosed (FIGS. 13A and 14). One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, Delta-sigma modulation.

II. D. Use and Operation

With the implantable electroacupuncture device (IDEA) 100 in hand, the IDEA 100 may be used most effectively to treat cardiovascular disease by first pre-setting stimulation parameters that the device will use during a stimulation session. FIG. 15A shows a timing waveform diagram illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is defined by the time period T3. The amplitude of the stimulus pulses is defined by the amplitude A1. This amplitude may be expressed in either voltage or current.

Figure 15B:
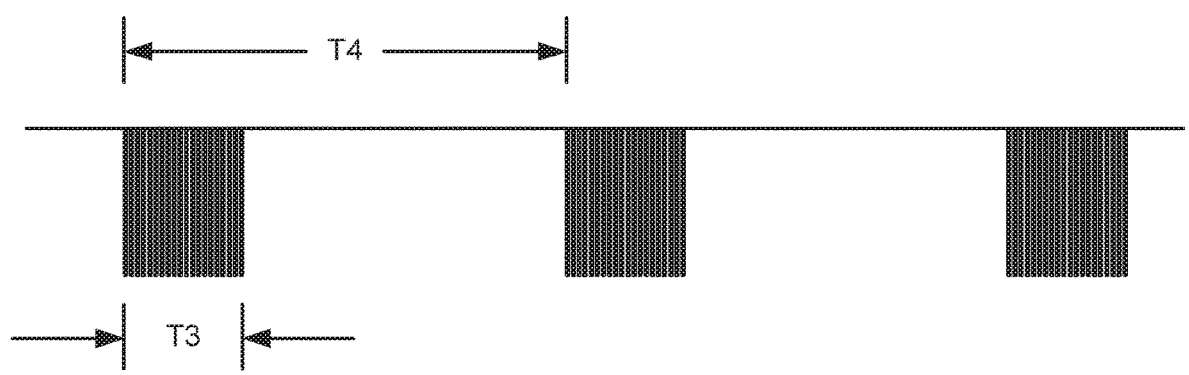
FIG. 15B shows a timing waveform diagram of multiple stimulation sessions, and illustrates the waveforms on a more condensed time scale.

Turning next to FIG. 15B, a timing waveform diagram is shown that illustrates the manner in which the stimulation sessions are administered in accordance with a preferred stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. T4 thus is the period of the stimulation session frequency, and the stimulation session frequency is equal to 1/T4.

One preferred set of parameters to use to define a stimulation regimen are

T1=0.5 milliseconds
T2=500 milliseconds
T3=30 minutes
T4=7 days (10,080 minutes)
A1=6 volts (across 1 kOhm)

It is to be emphasized that the values shown above for the stimulation regimen are representative of only one preferred stimulation regimen that could be used. Other stimulation regimens that could be used, and the ranges of values that could be used for each of these parameters, are as defined in the claims.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery life to be extended, which in turn allows the IEAD housing to be very small, which makes the IEAD ideally suited for being used without leads, thereby making it relatively easy to implant the device at the desired acupuncture site, but it also limits the frequency and duration of stimulation sessions. Limiting the frequency and duration of the stimulation sessions is a key aspect of applicants' invention because it recognizes that some treatments, such as treating cardiovascular disease, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce the sustained therapeutic effect. Thus, applicants have based their treatment regimens on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit 220, the IEAD 100 needs to be implanted. Implantation is a simple procedure, and is described above in connection with the description of FIGS. 1A and 1B.

For treating heart failure, coronary artery disease, myocardial ischemia or angina, the specified acupoint at which the EA stimulation pulses should be applied in accordance with a selected stimulation regimen is at least one of the following acupoints: PC6, ST36, BL14 (also referred to as UB14), EX-HN1 (located approximately one centimeter from GV20), HT7, HT5, LI11, LU2 and LU7.

Figure 16:
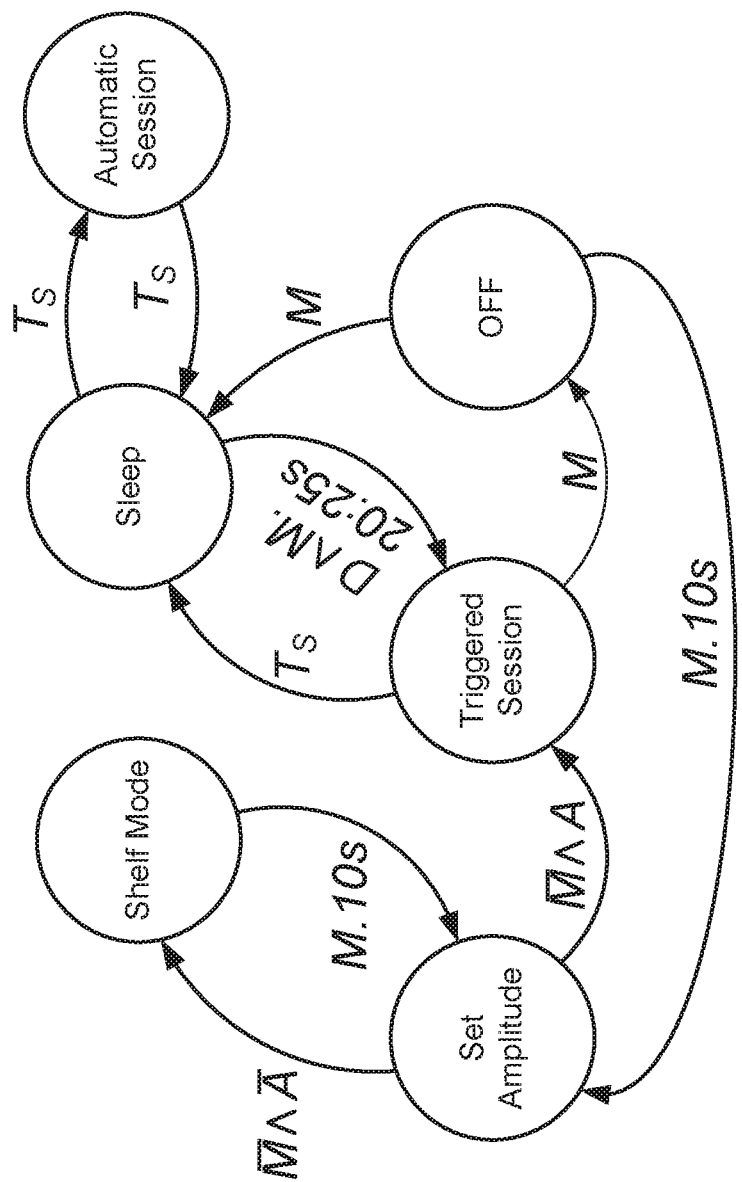

After implantation, the IEAD must be turned ON, and otherwise controlled, so that the desired stimulation regimen may be carried out. In one preferred embodiment, control of the IEAD after implantation, as well as anytime after the housing of the IEAD has been hermetically sealed, is performed as shown in the state diagram of FIG. 16. Each circle shown in FIG. 16 represents a "state" that the micro-controller U2 (in FIG. 13A or 14) may operate in under the conditions specified. As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10 s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M} \wedge A$), the device continues into the "Triggered Session" so the patient receives the initial therapy. If the magnet is removed during "Set Amplitude" while the amplitude is zero ($\overline{M} \wedge \overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M.10 s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20:25 s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in Appendix C, attached hereto, and incorporated by reference herein.

Relationship with Applicant's Other Inventions

Readers of this patent application who have also read Applicant's copending patent application(s) and issued patent(s) relating to the treatment of hypertension using a small, implantable EA device of the type described herein, will recognize that the treatment described there for hypertension treatment, including one of the acupoints, PC6, where the stimulation pulses are applied, is essentially the same as that described herein for the treatment of the four conditions of cardiovascular disease (heart failure, CAD, myocardial ischemia and angina) that are the focus of this patent application. Why is this? Are the inventions the same invention? The answer is that while the apparatus (the small implantable EA device) is essentially the same, and the stimulation regimen and point of application are essentially the same (or at least potentially may be the same depending upon the particular acupoint selected and the particular stimulation regimen parameters selected), the inventions target different conditions, and hence are different. Just like a wrench, for example, is a tool that may be used, sometimes alone but most often in combination with other tools, for a wide variety of applications, the EA device described herein, and its manner of use, may be used, sometimes alone but most often in combination with other tools, for a wide variety of beneficial applications, one of which is treating various conditions associated with cardiovascular disease, and another of which is treating hypertension.

The close relationship between the two inventions (hypertension treatment and cardiovascular disease treatment)

makes sense. In addition to heart failure, the sympathetic nervous system (SNS) is increased in the other conditions Applicant treats with this invention—in coronary artery disease, angina, and myocardial ischemia. Raised sympathetic nervous activity is the common denominator. And while a patient with one of these aforementioned conditions may or may not be hypertensive, the mechanism of action brought about by the device and methods disclosed in Applicant's hypertension treatment patent application involves the reduction of sympathetic activity. That is, the effect on blood pressure, Applicant submits, from the use of their EA device at acupoint PC6 (Neiguan), is secondary and results from the inhibiting effect on the SNS.

For example, in experimental models, it has been demonstrated that low frequency electroacupuncture (EA) stimulation at acupoint PC6 (Neiguan) effectively stimulates somatic afferents to provide input to regions such as the rVLM that regulates sympathetic outflow. See, Zhou W Y, Tjen-A-Looi S C, Longhurst J C, "Brain stem mechanisms underlying acupuncture modality-related modulation of cardiovascular responses in rats," *J Appl Physiol* 2005, 99:851-860; Zhou W, Fu L W, Tjen-A-Looi S C, et al., "Afferent mechanisms underlying stimulation of modality-related modulation of acupuncture-related cardiovascular responses," *J Appl Physiol* 2005,98:872-880. Furthermore, in experiments measuring the effect of stimulating acupoint PC6 (Neiguan) on blood pressure, the extent of blood pressure depression is dependent on the extent of convergent input to premotor sympathetic neurons in the rVLM. Tjen-A-Looi S C, Li P, Longhurst J C. "Medullary substrate and differential cardiovascular responses during stimulation of specific acupoints," *Am J Physiol Regul Integr Comp Physiol* 2004, 287:R852-R862. Thus, the effect on blood pressure seems to follow the effect on sympathetic activity.

Since Applicant believes the stimulation regimen and target at PC6 (Neiguan) disclosed in its hypertension treatment patent application represents at least one optimal system for reducing sympathetic activity, it has chosen to apply the same system to the conditions disclosed herein for which raised sympathetic activation is problematic. In fact, while much of the acupuncture studies performed at acupoint PC6 (Neiguan) were done to treat hypertension, the mechanism by which Applicant believes hypertension is improved—the reduction of sympathetic activity—may be more central to the treatment of heart failure. That is, hypertension may not always be driven sympathetically, whereas the hallmark of heart failure is heightened sympathetic drive. Thus, it is important that Applicant targets the SNS in the treatment of heart failure, in particular, by the application of its EA device at acupoint PC6 (Neiguan).

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense and are not intended to be exhaustive or to limit the invention to any precise form disclosed. Many modifications and variations are possible in light of the above teaching. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. A method of treating cardiovascular disease in a patient, comprising:
   generating, by an implantable stimulator configured to be implanted beneath a skin surface of the patient, stimulation sessions at a duty cycle that is less than 0.05, wherein
   the duty cycle is a ratio of T3 to T4,
   each stimulation session included in the stimulation sessions has a duration of T3 minutes and occurs at a rate of once every T4 minutes, and
   the implantable stimulator is powered by a primary battery located within the implantable stimulator and having an internal impedance greater than 5 ohms; and
   applying, by the implantable stimulator in accordance with the duty cycle, the stimulation sessions to a tissue location associated with the cardiovascular disease.

2. The method of claim 1, wherein the tissue location comprises a median nerve of the patient.

3. The method of claim 1, wherein the implantable stimulator is configured to be implanted at an acupoint PC6.

4. The method of claim 1, wherein T3 is at least 10 minutes and less than 40 minutes, and wherein T4 is at least 1440 minutes.

5. The method of claim 1, further comprising:
   receiving, by the implantable stimulator from a device external to the implantable stimulator, a control command that sets the times T3 and T4 to appropriate values configured to treat the cardiovascular disease;
   wherein the generating of the stimulation sessions is performed in accordance with the control command.

6. The method of claim 5, wherein the receiving of the control command comprises detecting, with an electromagnetic field sensor included in the implantable stimulator, a magnetic field generated by the device external to the implantable stimulator.

7. The method of claim 1, wherein the primary battery located within the implantable stimulator has a capacity of less than 60 milliamp-hours (mAh).

8. The method of claim 1, wherein the primary battery located within the implantable stimulator is a coin-cell battery.

9. The method of claim 1, wherein the applying of the stimulation sessions to the tissue location comprises applying the stimulation sessions to the tissue location by way of an electrode array.

10. The method of claim 9, wherein the electrode array comprises a central electrode of a first polarity centrally located on a first surface of a housing of the implantable stimulator and an annular electrode of a second polarity and that is spaced apart from the central electrode.

11. The method of claim 10, wherein the annular electrode is located on the first surface of the housing.

12. The method of claim 10, wherein the annular electrode comprises a ring electrode located around a perimeter edge of the housing.

13. The method of claim 9, wherein the electrode array comprises a plurality of electrodes located on a lead that is attached to the implantable stimulator.

14. An implantable stimulator for treating cardiovascular disease in a patient, comprising:
   a housing configured to be implanted beneath a skin surface of the patient, pulse generation circuitry located within the housing, wherein the pulse generation circuitry is configured to generate stimulation sessions at a duty cycle that is less than 0.05, and
apply, in accordance with the duty cycle, the stimulation sessions a tissue location associated with the cardiovascular disease; and
a primary battery located within the housing and having an internal impedance greater than 5 ohms, the primary battery configured to provide operating power to the pulse generation circuitry;
wherein
the duty cycle is a ratio of T3 to T4, and
each stimulation session included in the stimulation sessions has a duration of T3 minutes and occurs at a rate of once every T4 minutes.

15. The implantable stimulator of claim 14, wherein the tissue location comprises a median nerve of the patient.

16. The implantable stimulator of claim 14, wherein the primary battery located within the implantable stimulator has a capacity of less than 60 milliamp-hours (mAh).

17. The implantable stimulator of claim 14, wherein the primary battery located within the implantable stimulator is a coin-cell battery.

18. The implantable stimulator of claim 14, further comprising an electrode array, wherein the implantable stimulator is configured to apply the stimulation sessions to the tissue location comprises by way of the electrode array.

19. The implantable stimulator of claim 18, wherein the electrode array comprises:
a central electrode of a first polarity centrally located on a surface of the housing; and
an annular electrode of a second polarity and that is spaced apart from the central electrode.

20. A system for treating cardiovascular disease in a patient, comprising:
means for generating, within an implantable stimulator configured to be implanted beneath a skin surface of the patient, stimulation sessions at a duty cycle that is less than 0.05, wherein
the duty cycle is a ratio of T3 to T4,
each stimulation session included in the stimulation sessions has a duration of T3 minutes and occurs at a rate of once every T4 minutes, and
the implantable stimulator is powered by a primary battery located within the implantable stimulator and having an internal impedance greater than 5 ohms; and
means for applying, in accordance with the duty cycle, the stimulation sessions to a tissue location associated with the cardiovascular disease.

* * * * *